US008623382B2

(12) United States Patent
Sidhu et al.

(10) Patent No.: US 8,623,382 B2
(45) Date of Patent: Jan. 7, 2014

(54) IMMUNOGENIC COMPOSITIONS FOR INDUCING AN IMMUNE RESPONSE TO HIV

(75) Inventors: Maninder K. Sidhu, New City, NY (US); John H. Eldridge, Somers, NY (US); Michael Egan, Washingtonville, NY (US); Zimra Israel, New York, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 13/008,694

(22) Filed: Jan. 18, 2011

(65) Prior Publication Data

US 2012/0003265 A1  Jan. 5, 2012

Related U.S. Application Data

(62) Division of application No. 11/629,610, filed as application No. PCT/US2005/021168 on Jun. 15, 2005, now abandoned.

(60) Provisional application No. 60/662,275, filed on Mar. 16, 2005, provisional application No. 60/624,983, filed on Nov. 3, 2004, provisional application No. 60/580,438, filed on Jun. 17, 2004.

(51) Int. Cl.
*A61K 39/21* (2006.01)
*A61K 39/12* (2006.01)

(52) U.S. Cl.
USPC ..................................... 424/208.1; 424/199.1

(58) Field of Classification Search
USPC .......................... 404/208.1; 424/199.1; 604/20
See application file for complete search history.

(56) References Cited

U.S. PATENT DOCUMENTS

| | | | |
|---|---|---|---|
| 5,547,862 A | 8/1996 | Meador et al. | |
| 5,583,038 A | 12/1996 | Stover | |
| 5,688,637 A | 11/1997 | Moncany et al. | |
| 5,773,602 A | 6/1998 | Alizon et al. | |
| 5,786,177 A | 7/1998 | Moncany et al. | |
| 5,817,637 A | 10/1998 | Weiner et al. | |
| 5,843,638 A | 12/1998 | Montagnier et al. | |
| 5,869,631 A | 2/1999 | Alizon et al. | |
| 6,060,273 A | 5/2000 | Dirks et al. | |
| 6,165,715 A * | 12/2000 | Collins et al. ............... | 435/6.16 |
| 6,187,759 B1 | 2/2001 | Tarpey et al. | |
| 6,395,891 B1 | 5/2002 | Karn et al. | |
| 6,399,294 B1 | 6/2002 | Charneau et al. | |
| 6,428,952 B1 | 8/2002 | Montagnier et al. | |
| 6,472,171 B1 | 10/2002 | Toman et al. | |
| 6,589,783 B2 | 7/2003 | Novy et al. | |
| 6,627,395 B1 | 9/2003 | Montagnier et al. | |
| 6,995,008 B1 | 2/2006 | Liu et al. | |
| 7,993,651 B2 | 8/2011 | Hanke et al. | |
| 2004/0033487 A1* | 2/2004 | Nabel et al. ......................... | 435/5 |
| 2006/0018881 A1 | 1/2006 | Liu et al. | |
| 2006/0275897 A1* | 12/2006 | Nabel et al. ............... | 435/320.1 |

FOREIGN PATENT DOCUMENTS

| | | |
|---|---|---|
| EP | 0 658 198 B1 | 1/1999 |
| EP | 1015596 B1 | 8/2006 |
| WO | WO 92/05264 | 4/1992 |
| WO | WO/92/05264 * | 4/1992 |
| WO | WO 94/16737 A1 | 8/1994 |
| WO | WO/95/24485 * | 9/1995 |
| WO | WO 95/24485 | 9/1995 |
| WO | WO 97/20463 | 6/1997 |
| WO | WO 97/28818 A1 | 8/1997 |
| WO | WO 98/17799 | 4/1998 |
| WO | WO 99/04026 A2 | 1/1999 |
| WO | WO 99/30733 A1 | 6/1999 |
| WO | WO9927958 * | 6/1999 |
| WO | WO 99/43839 | 9/1999 |
| WO | WO 01/47955 A2 | 7/2001 |
| WO | WO 01/79518 A2 | 10/2001 |
| WO | WO/02/06303 * | 1/2002 |
| WO | WO/03/035910 * | 1/2003 |
| WO | WO 03/035910 | 5/2003 |
| WO | 03/048366 A1 | 6/2003 |
| WO | 2004/035006 A2 | 4/2004 |
| WO | WO 2004/093906 A1 | 11/2004 |
| WO | WO 2005/068634 A1 | 7/2005 |

OTHER PUBLICATIONS

Goins et al Journal of Virology, 1994, 2239-2252).*
Bures, et al. AIDS Res Hum Retroviruses 2000 16:2019-35.*
Megede et al Journal of Virology, 2003, 6197-5207).*
Attal, J; et al.; Journal of Biotechnology 77:179-189 (2000).
Conroy, RM; et al.; Gene Therapy 3:67-74 (1996).
Davies, JF II; et al.; Science 252:88-95 (1991).
Goins, WF; et al.; Journal of Virology 68(4):2239-2252 (1994).
Goins, WF; et al.; Journal of Virology 73(1):519-532 (1999).
Gurunathan, S; et al.; Current Opinion in Immunology 12:442-447 (2000).
He, Z; et al.; Virology 270:146-161 (2000).
Herrera, AM; et al.; Biochemical and Biophysical Research Communications 279:548-551 (2000).
Iwasaki, A; et al.; The Journal of Immunology 158:4591-4601 (1997).
Kaps, I; et al.; Gene 278:115-124 (2001).
Larder; BA; et al.; Nature 327:716-717 (1987).
Larder, BA; et al.; Proc. Natl. Acad. Sci. 86:4803-4807 (1989).
Leavitt, AD; et al.; The Journal of Biological Chemistry 268(3):2113-2119 (1993).
Lin, Y; et al.; Biochemistry 40:12959-12966 (2001).
Loeb, DD; et al.; Nature 340:397-400 (1989).
Lueking, A; et al.; Methods in Molecular Biology, vol. 25, *E coli* Gene Expression Protocols.
zur Megede, J; et al.; Journal of Virology 77(11):6197-6207 (2003).
Mullinax, RL; et al.; Methods in Molecular Biology, vol. 25, *E coli* Gene Expression Protocols.
Overell, RW; et al.; Molecular and Cellular Biology 8(4):1803-1808 (1988).

(Continued)

*Primary Examiner* — Anoop Singh
(74) *Attorney, Agent, or Firm* — Victoria S. Molenda

(57) ABSTRACT

The invention relates to immunogenic compositions for inducing an immune response to HIV comprising combinations of two, three, or four plasmids, where each plasmid is expressing a defined antigen, which may be a single antigen or a fusion of two or three antigens.

3 Claims, 12 Drawing Sheets

(56) References Cited

OTHER PUBLICATIONS

Pachuk, CJ; et al.; Biochimica et Biophysica Acta, 1468(1-2):20-30 (2000).

Rininsland, FH; et al.; Journal of Immunological Methods 240:143-155 (2000).

Schatz, O; et al.; FEBS Letters 257(2):311-314 (1989).

Soares, K; et al.; Journal of Virology 70(8):5384-5394 (1996).

Sutter, G. and HAAS, J.; AIDS 15(5) S139-S145 (2001).

Wasylyk, B; et al.; Nucleic Acids Research 12(14):5589-5608 (1984).

Weyer, U. and Possee, RD; Journal of General Virology 72:2967-2974 (1991).

Wiskerchen, M. and Muesing, MA; Journal of Virology 69(1):376-386 (1995).

Wolfe, D; et al.; Molecular Therapy 3(1):61-69 (2001).

Wu, X; et al.; Journal of Virology 70(6):3378-3384 (1996).

Xu, Z; et al.; Gene 272:149-156 (2001).

Yu, X; et al.; Molecular Therapy 7(6):827-838 (2003).

Dinchuk et al, "Generation of Transgenic Mice Carrying HIV Tat and Nef Genes", Poster Th.A.291 (1990).

Egan et al, "Rational design of a plasmid DNA vaccine capable of eliciting cell-mediated immune responses to multiple HIV antigens in mice", Vaccine 24(21):4510-4523 (2006).

Giri et al, "DNA Vaccines against Human Immunodeficiency Virus Type 1 in the Past Decade", Clinical Microbiology Reviews, 17(2):370-389 (2004).

Meima et al, "Role of Enzymes of Homologous Recombination in Illegitimate Plasmid Recombination in *Bacillus subtilis*", Journal of Bacteriology, 179(4):1219-1229.

Murphy et al, "Effects of the tat and nef Gene Products of Human Immunodeficiency Virus Type 1 (HIV-1) on Transcription Controlled by the HIV-1 Long Terminal Repeat and on Cell Growth in Macrophages", Journal of Virology, 67(12):6956-6964 (1993).

Murphy et al, "The HIV-1 regulatory protein Nef has a specific function in viral expression in a murine macrophage cell line", Journal of Leukocyte Biology, 56:294-303 (1994).

Nabel, "HIV vaccine strategies", Vaccine, 20:1945-1947 (2002).

\* cited by examiner

| Lane | Plasmid Combinations Transfected |
|---|---|
| 1 | 205 (gag/pol) + 101(env) + 104(ntv) |
| 2 | 201(gag,pol) + 202(env, ntv) |
| 3 | 203( gag/pol/ntv, env) |
| 4 | 303(gag/pol, env, ntv) |
| 5 | 101(env) + 102(gag) + 103(pol) + 104(ntv) |
| 6 | 001 (control) |

SEQUENCE LISTING

```
<160> NUMBER OF SEQ ID NOS: 6

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 6
<212> TYPE: DNA
<213> ORGANISM: Human immunodeficiency virus type 1

<400> SEQUENCE: 2 tttttt                                                                    6

<210> SEQ ID NO 3
<211> LENGTH: 6
<212> TYPE: DNA
<213> ORGANISM: Human immunodeficiency virus type 1
<220> FEATURE:
<221> NAME/KEY: misc_difference
<222> LOCATION: (1)..(1)
<223> OTHER INFORMATION: mutation to allow read through
<220> FEATURE:
<221> NAME/KEY: misc_difference
<222> LOCATION: (4)..(4)
<223> OTHER INFORMATION: mutation to allow read through
<220> FEATURE:
<221> NAME/KEY: misc_difference
<222> LOCATION: (6)..(6)
<223> OTHER INFORMATION: mutation to allow read through

<400> SEQUENCE: 3 cttctg                                                                    6
```

```
<210> SEQ ID NO 4
<211> LENGTH: 4
<212> TYPE: PRT
<213> ORGANISM: Human immunodeficiency virus type 1

<400> SEQUENCE: 4

Lys Gly Arg Pro
1

<210> SEQ ID NO 5
<211> LENGTH: 10
<212> TYPE: PRT
<213> ORGANISM: Human immunodeficiency virus type 1

<400> SEQUENCE: 5

Asp Arg Gln Gly Thr Val Ser Phe Asn Phe
1               5                   10

<210> SEQ ID NO 6
<211> LENGTH: 4
<212> TYPE: PRT
<213> ORGANISM: Human immunodeficiency virus type 1

<400> SEQUENCE: 6

Pro Gln Ile Thr
1
```

IMMUNOGENIC COMPOSITIONS FOR INDUCING AN IMMUNE RESPONSE TO HIV

This application is a divisional of U.S. application Ser. No. 11/629,610, filed Dec. 14, 2006 (abandoned), which is a national stage application under 35 U.S.C. §371 of International Application PCT/US2005/021168, filed Jun. 15, 2005, which claims the benefit of U.S. Provisional Application Nos. 60/662,275, filed Mar. 16, 2005, 60/624,983, filed Nov. 3, 2004, and 60/580,438, filed Jun. 17, 2004, the contents of each of which applications are herein incorporated by reference in their entirety.

FIELD OF THE INVENTION

This invention relates to plasmids, immunogenic compositions and methods to improve prophylactic and therapeutic immune responses to antigens.

BACKGROUND OF THE INVENTION

Immunization using plasmid DNA-based immunogenic compositions is a powerful tool that is useful for developing approaches to prevent or treat infectious diseases or in the treatment of ongoing disease processes. Plasmid DNA immunization has been extensively tested in animal models where it has been found to be effective in inducing both cellular and humoral immune responses against a wide variety of infectious agents and tumor antigens. See Donnelly J J, et al., *Ann. Rev. Immunol.*; 15: 617-48 (1997); Iwasaki A, et al., *J Immunol* 158 (10): 4591-601 (1997); Wayne, C. L. and Bennett M., *Crit. Rev. Immunol.*, 18: 449-484 (1998).

An important advantage of plasmid DNA immunization is that genes can be cloned, modified and positioned into a potential plasmid DNA expression vector in such a way as to allow for relevant post-transcriptional modifications, expression levels, appropriate intracellular trafficking and antigen presentation. Plasmid DNA vectors useful for DNA immunization are similar to those employed for delivery of reporter or therapeutic genes. Plasmid DNA-based immunization uses the subject's cellular machinery to generate the foreign protein and stimulates the subject's immune system to mount an immune response to the protein antigen. Such plasmid DNA vectors generally contain eukaryotic transcriptional regulatory elements that are strong viral promoter/enhancer elements to direct high levels of gene expression in a wide host cell range and a polyadenylation sequence to ensure appropriate termination of the expressed mRNA. While, viral regulatory elements are advantageous for use in plasmid DNA vectors, the use of unmodified viral vectors to express the relevant genes may raise safety and technical issues not encountered with plasmid DNA.

Current plasmid DNA designs, however, limit the expression of multiple genes from one vector backbone in a single target cell. Therefore, to transfer and express multiple genes, co-transfection of the target cells with separate plasmids is required. When cells must be co-transfected with multiple plasmids, it is difficult to achieve optimal expression of all encoded genes, especially when the plasmid is being used in vivo. Previous attempts to overcome these limitations and express two or more genes include the use of the following: viral vectors, multiple alternatively spliced transcripts from proviral DNA, fusion of genes, bicistronic vectors containing IRES sequences (Internal ribosome entry site) from viruses and dual expression plasmids. See Conry R. M. et al., *Gene Therapy.* 3(1):67-74, (1996); Chen T T. et al., *Journal of Immunology.* 153(10):4775-87, (1994); Ayyavoo V. et al., *AIDS.* 14(1):1-9, (2000); Amara R. R. et al., *Vaccine.* 20(15): 1949-55, (2002); Singh G, et al., Vaccine 20: 1400-1411 (2002).

None of the existing plasmid designs have solved the problem of providing a DNA plasmid suitable for expressing more than two independent open reading frames in human immunogenic compositions. In the case of bicistronic vectors, in many instances, only the first gene transcribed upstream of the IRES is expressed strongly from either a plasmid or a retroviral vector. See Sugimoto Y., et al., *Hum. Gen. Ther.* 6: 905-915 (1995); Mizoguchi H, et al., Mol. Ther. 1:376-382 (2000). Dual expression cassettes on the other hand have performed better. For example, it was found that co-delivery of cDNA for B7-1 and human carcinoembryonic antigen (CEA) with a single plasmid having two independent cassettes resulted in far superior immune responses, when compared to separate plasmids. See Conry R. M. et al., *Gene Therapy.* 3(1):67-74, (1996). However, in this case the two independent cassettes involved both consisted of homologous HCMV promoter and bovine growth hormone (BGH) polyadenylation sequences. The presence of homologous sequences within a plasmid renders that plasmid unsuitable for use in DNA immunogenic compositions, because the presence of homologous sequences within the plasmid backbone increases the possibility of recombination between the repeated sequences and results in vector instability.

Another constraint one confronts when designing a plasmid DNA vector for use in a human immunogenic composition involves size and organization of the plasmid. As transcriptional units are added to a plasmid, interference between transcriptional units can arise, for example in the form of steric hindrance. The cell's RNA transcription complex must be able to bind to the multiple sites on a polytranscriptional unit plasmid, uncoil the DNA and effectively transcribe the genes. Simply making the plasmid bigger is not necessarily the best solution for several reasons including plasmid instability, difficulty in plasmid manufacture and, most importantly, dosing considerations. To design an improved plasmid DNA multiple transcriptional unit vector, one must consider placement of genes, spacing and direction of transcription of open reading frames, level of expression, ease of manufacture, safety and the ultimate dose of the vector necessary to immunize the subject.

Therefore, there remains a need for innovative plasmid DNA, non-viral vector designs for use in expressing multiple proteins from complex pathogens like HIV, where a broad immune response to many proteins is required. In addition, a need exists for polyvalent DNA-based immunogenic compositions that can direct expression of high levels of multiple HIV genes within a single cell.

SUMMARY OF THE INVENTION

In one embodiment, the present invention provides a DNA plasmid comprising: (a) a first transcriptional unit comprising a nucleotide sequence that encodes a first polypeptide operably linked to regulatory elements including a first promoter and a first polyadenylation signal; (b) a second transcriptional unit comprising a nucleotide sequence that encodes a second polypeptide operably linked to regulatory elements including a second promoter and a second polyadenylation signal; (c) a third transcriptional unit comprising a nucleotide sequence that encodes a third polypeptide operably linked to regulatory elements including a third promoter and a third polyadenylation signal; wherein said first, said second and said third promoters are each derived from different transcriptional units; and wherein said first, said second and said third polyadenylation signals are each derived from different transcriptional units. In another embodiment of the invention, the first, second and third polypeptides are expressed in a eukaryotic cell.

In another embodiment, the present invention provides an immunogenic composition for inducing an immune response to selected antigens in a vertebrate host, the immunogenic composition comprising: (a) a DNA plasmid comprising a (i) a first transcriptional unit comprising a nucleotide sequence that encodes a first polypeptide operably linked to regulatory elements including a first promoter and a first polyadenylation signal; (ii) a second transcriptional unit comprising a nucleotide sequence that encodes a second polypeptide operably linked to regulatory elements including a second promoter and a second polyadenylation signal; (iii) a third transcriptional unit comprising a nucleotide sequence that encodes a third polypeptide operably linked to regulatory elements including a third promoter and a third polyadenylation signal; wherein the first, second and third promoters are each derived from different transcriptional units; wherein said first, second and third polyadenylation signals are each derived from different transcriptional units; and (b) at least one of a pharmaceutically acceptable diluent, adjuvant, carrier or transfection facilitating agent. In a particular embodiment of the invention, the transfection facilitating agent is bupivacaine. In another embodiment of the invention, the first, second and third polypeptides are expressed in a eukaryotic cell.

In certain embodiments of the invention, the immunogenic composition is administered to a mammal using in vivo electroporation. In a particular embodiment, electroporation involves electrically stimulating the muscle with an electrical current having a field strength in the range of from about 25 V/cm to about 800 V/cm.

In still another embodiment, the present invention provides a method of immunizing a vertebrate host against selected antigens comprising administering to the vertebrate host an immunogenic composition comprising: (a) a DNA plasmid comprising a (i) a first transcriptional unit comprising a nucleotide sequence that encodes a first polypeptide operably linked to regulatory elements including a first promoter and a first polyadenylation signal; (ii) a second transcriptional unit comprising a nucleotide sequence that encodes a second polypeptide operably linked to regulatory elements including a second promoter and a second polyadenylation signal; (iii) a third transcriptional unit comprising a nucleotide sequence that encodes a third polypeptide operably linked to regulatory elements including a third promoter and a third polyadenylation signal; wherein said first, second and third promoters are each derived from different transcriptional units; wherein the first, second and third polyadenylation signals are each derived from different transcriptional units; and (b) at least one of a pharmaceutically acceptable diluent, adjuvant, carrier or transfection facilitating agent. In another embodiment of the invention, the first, second and third polypeptides are expressed in a eukaryotic cell.

In another embodiment of the invention, the selected antigens are derived from the group consisting of a bacterium, a virus, an allergen and a tumor. In a particular embodiment, the selected antigens are viral antigens derived from a virus selected from the group consisting of Human immunodeficiency virus, Simian immunodeficiency virus, Respiratory syncytial virus, Parainfluenza virus type 1, Parainfluenza virus type 2, Parainfluenza virus type 3, Influenza virus, Herpes simplex virus, Human cytomegalovirus, Hepatitis A virus, Hepatitis B virus, Hepatitis C virus, Human papillomavirus, Poliovirus, rotavirus and coronavirus (SARS).

In still another embodiment of the invention, the selected antigens are bacterial antigens derived from a bacterium selected from the group consisting of *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Alloiococcus otiditis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare complex, Proteus mirabilis, Proteus vulgaris, Staphylococcus aureus, Staphylococcus epidermidis, Clostridium tetani, Leptospira interrogans, Borrelia burgdorferi, Pasteurella haemolytica, Pasteurella multocida, Actinobacillus pleuropneumoniae* and *Mycoplasma gallisepticum*.

In one embodiment of the invention, the vertebrate host is selected from the group consisting of mammals, birds and fish. In a certain embodiment of the invention, the vertebrate host is a mammal selected from the group consisting human, bovine, ovine, porcine, equine, canine and feline species.

In one embodiment of the invention, the first, second and third promoters are active in eukaryotic cells. In other embodiments of the invention, the first, second and third promoters are selected from the group consisting of human cytomegalovirus (HCMV) immediate early promoter, the simian cytomegalovirus (SCMV) promoter, the murine cytomegalovirus (MCMV) promoter, the herpes simplex virus (HSV) latency-associated promoter-1 (LAP1), Simian virus 40 promoter, human elongation factor 1 alpha promoter, and the human muscle cell specific desmin promoter.

In certain embodiments of the invention, the first, second and third polyadenylation signals are selected from the group consisting of rabbit beta-globin poly(A) signal, synthetic polyA, HSV Thymidine kinase poly A, Human alpha globin poly A, SV40 poly A, human beta globin poly A, polyomavirus poly A, and Bovine growth hormone poly A.

In a particular embodiment of the invention, the first transcriptional unit expresses a gag-pol fusion protein from a fusion of the gag and pol genes of HIV. In one embodiment of the invention, the fusion of the gag and pol genes of HIV or gag-pol gene is derived from the HXB2 isolate of HIV.

In a certain embodiment of the invention, the second transcriptional unit expresses an envelope protein from the envelope gene of HIV. In a particular embodiment of the invention, the envelope gene is derived from a primary isolate 6101 of HIV.

In a specific embodiment of the invention, the third transcriptional unit expresses a nef, tat, and vif (NTV) fusion protein from a fusion of the nef, tat, and vif (ntv) genes of HIV. In a particular embodiment of the invention, the fusion of the nef, tat, and vif genes of HIV or ntv gene is derived from the NL4-3 isolate of HIV.

In a specific embodiment of the invention, in a three transcriptional unit plasmid, the direction of transcription for the first transcriptional unit is in the opposite direction from the direction of transcription of the second transcriptional unit. In another embodiment of the invention, the direction of transcription for first transcriptional unit is in the opposite direction from the direction of transcription of the third transcriptional unit.

In a certain embodiment of the invention, the invention provides a three transcriptional unit plasmid, which further comprises a nucleotide sequence that encodes a selectable marker operably linked to regulatory elements including a promoter and a polyadenylation signal. In one embodiment, the selectable marker is selected from the group consisting of kanamycin resistance gene, ampicillin resistance gene, tetracycline resistance gene, hygromycin resistance gene and chloroamphenicol resistance gene. In another embodiment, the location of the selectable marker is selected from the group consisting of spacer region 1, spacer region 2 and spacer region 3. In a specific embodiment, the location of the selectable marker is spacer region 2.

In another embodiment of the invention, the invention provides a three transcriptional unit plasmid, which further comprises a bacterial origin of replication. In another embodiment, the location of the origin of replication is selected from the group consisting of spacer region 1, spacer region 2 and spacer region 3. In a specific embodiment, the location of the selectable marker is spacer region 3. In a particular embodiment, the origin of replication is the pUC origin of replication.

In one embodiment of the invention, the invention provides a three transcriptional unit plasmid, wherein the plasmid is less than about 15 kilobase pairs in total size. In another embodiment of the invention, spacer region 1 is less than about 400 base pairs, spacer region 2 is less than about 1100 base pairs and spacer region 3 is less than about 1100 base pairs.

In one embodiment, the invention provides an immunogenic composition for inducing an immune response to human immunodeficiency virus (HIV) in a vertebrate host, said immunogenic composition comprising: (a) a first DNA plasmid comprising a single transcriptional unit comprising a nucleotide sequence that encodes an HIV gag-pol fusion polypeptide, wherein said single transcriptional unit is operably linked to regulatory elements including a promoter and a polyadenylation signal; (b) a second DNA plasmid comprising (i) a first transcriptional unit comprising a nucleotide sequence that encodes an HIV nef-tat-vif fusion polypeptide operably linked to regulatory elements including a first promoter and a first polyadenylation signal; (ii) a second transcriptional unit comprising a nucleotide sequence that encodes an HIV envelope polypeptide operably linked to regulatory elements including a second promoter and a second polyadenylation signal; wherein said first and second promoters are each derived from different transcriptional units; and wherein said first and second polyadenylation signals are each derived from different transcriptional units; and wherein the direction of transcription for said first transcriptional unit is in the opposite direction from the direction of transcription of said second transcriptional unit; or wherein the direction of transcription for said first transcriptional unit is in the same direction from the direction of transcription of said second transcriptional unit and said first and second transcriptional units are separated by a spacer region of at least one kilobase pairs; and (c) at least one of a pharmaceutically acceptable diluent, carrier or transfection facilitating agent. In a particular embodiment of the invention, the transfection facilitating agent is bupivacaine. In a particular embodiment, the promoter on the first plasmid is the human cytomegalovirus (HCMV) immediate early promoter, the polyadenylation signal on the first plasmid is the Bovine growth hormone poly A polyadenylation signal and the first DNA plasmid encodes an HIV gag-pol fusion polypeptide, wherein the fusion of the gag and pol genes of HIV or gag-pol gene is derived from the HXB2 isolate of HIV. In a certain embodiment, the first promoter on the second plasmid is the human cytomegalovirus (HCMV) immediate early promoter and the first polyadenylation signal on the second plasmid is the SV40 poly A polyadenylation signal and the polypeptide is a nef, tat, and vif (NTV) fusion protein expressed from a fusion of the nef, tat, and vif (ntv) genes derived from the NL4-3 isolate of HIV. In a particular embodiment, the second promoter on the second plasmid is the simian cytomegalovirus (SCMV) promoter, the second polyadenylation signal on the second plasmid is the Bovine growth hormone (BGH) polyadenylation signal encoded envelope polypeptide is derived from the primary isolate 6101 of HIV.

In still a further embodiment, the invention provides a method of immunizing a vertebrate host against selected antigens comprising administering to said vertebrate host an immunogenic composition comprising: (a) a first DNA plasmid comprising a single transcriptional unit comprising a nucleotide sequence that encodes an HIV gag-pol fusion polypeptide, wherein said single transcriptional unit is operably linked to regulatory elements including a promoter and a polyadenylation signal; (b) a second DNA plasmid comprising (i) a first transcriptional unit comprising a nucleotide sequence that encodes an HIV nef-tat-vif fusion polypeptide operably linked to regulatory elements including a first promoter and a first polyadenylation signal; (ii) a second transcriptional unit comprising a nucleotide sequence that encodes an HIV envelope polypeptide operably linked to regulatory elements including a second promoter and a second polyadenylation signal; wherein said first and second promoters are each derived from different transcriptional units; and wherein said first and second polyadenylation signals are each derived from different transcriptional units; and wherein the direction of transcription for said first transcriptional unit is in the opposite direction from the direction of transcription of said second transcriptional unit; or wherein the direction of transcription for said first transcriptional unit is in the same direction from the direction of transcription of said second transcriptional unit and said first and second transcriptional units are separated by a spacer region of at least one kilobase pairs; and (c) at least one of a pharmaceutically acceptable diluent, carrier or transfection facilitating agent. In a particular embodiment of the invention, the transfection facilitating agent is bupivacaine. In a particular embodiment, the promoter on the first plasmid is the human cytomegalovirus (HCMV) immediate early promoter, the polyadenylation signal on the first plasmid is the Bovine growth hormone poly A polyadenylation signal and the first DNA plasmid encodes an HIV gag-pol fusion polypeptide, wherein the fusion of the gag and pol genes of HIV or gag-pol gene is derived from the HXB2 isolate of HIV. In a certain embodiment, the first promoter on the second plasmid is the human cytomegalovirus (HCMV) immediate early promoter and the first polyadenylation signal on the second plasmid is the SV40 poly A polyadenylation signal and the polypeptide is a nef, tat, and vif (NTV) fusion protein expressed from a fusion of the nef, tat, and vif (ntv) genes derived from the NL4-3 isolate of HIV. In a particular embodiment, the second promoter on the second plasmid is the simian cytomegalovirus (SCMV) promoter, the second polyadenylation signal on the second plasmid is the Bovine growth hormone (BGH) polyadenylation signal encoded envelope polypeptide is derived from the primary isolate 6101 of HIV. In one embodiment, the immunogenic composition is administered to a mammal using in vivo electroporation. In a particular embodiment, the electroporation involves electrically stimulating the muscle with an electrical current having a field strength in the range of from about 25 V/cm to about 800 V/cm. In one embodiment, the transfection facilitating agent is bupivacaine.

In one embodiment, the invention provides an immunogenic composition for inducing an immune response to human immunodeficiency virus (HIV) in a vertebrate host, the immunogenic composition comprising: (a) a first DNA plasmid comprising a single transcriptional unit comprising a nucleotide sequence that encodes an HIV gag polypeptide, wherein said single transcriptional unit is operably linked to regulatory elements including a promoter and a polyadenylation signal; (b) a second DNA plasmid comprising a single transcriptional unit comprising a nucleotide sequence that encodes an HIV pol polypeptide, wherein said single transcriptional unit is operably linked to regulatory elements including a promoter and a polyadenylation signal; (c) a third DNA plasmid comprising (i) a first transcriptional unit comprising a nucleotide sequence that encodes an HIV nef-tat-vif fusion polypeptide operably linked to regulatory elements including a first promoter and a first polyadenylation signal; (ii) a second transcriptional unit comprising a nucleotide sequence that encodes an HIV envelope polypeptide operably linked to regulatory elements including a second promoter and a second polyadenylation signal; wherein said first and second promoters are each derived from different transcriptional units; and wherein said first and second polyadenylation signals are each derived from different transcriptional units; and wherein the direction of transcription for said first transcriptional unit is in the opposite direction from the direction of transcription of said second transcriptional unit; or wherein the direction of transcription for said first transcriptional unit is in the same direction from the direction of transcription of said second transcriptional unit and said first and second transcriptional units are separated by a spacer region of at least one kilobase pairs; and (d) a fourth DNA plasmid comprising a nucleotide sequence that encodes an adjuvant polypeptide, wherein said nucleotide sequence is operably linked to regulatory elements including a promoter and a polyadenylation signal; and (e) at least one of a pharmaceutically acceptable diluent, carrier or transfection facilitating agent.

In another embodiment, the invention provides a method of immunizing a vertebrate host against selected antigens comprising administering to said vertebrate host an immunogenic composition comprising: (a) a first DNA plasmid comprising a single transcriptional unit comprising a nucleotide sequence that encodes an HIV gag polypeptide, wherein said single transcriptional unit is operably linked to regulatory elements including a promoter and a polyadenylation signal; (b) a second DNA plasmid comprising a single transcriptional unit comprising a nucleotide sequence that encodes an HIV pol polypeptide, wherein said single transcriptional unit is operably linked to regulatory elements including a promoter and a polyadenylation signal; (c) a third DNA plasmid comprising (i) a first transcriptional unit comprising a nucleotide sequence that encodes an HIV nef-tat-vif fusion polypeptide operably linked to regulatory elements including a first promoter and a first polyadenylation signal; (ii) a second transcriptional unit comprising a nucleotide sequence that encodes an HIV envelope polypeptide operably linked to regulatory elements including a second promoter and a second polyadenylation signal; wherein said first and second promoters are each derived from different transcriptional units; and wherein said first and second polyadenylation signals are each derived from different transcriptional units; and wherein the direction of transcription for said first transcriptional unit is in the opposite direction from the direction of transcription of said second transcriptional unit; or wherein the direction of transcription for said first transcriptional unit is in the same direction from the direction of transcription of said second transcriptional unit and said first and second transcriptional units are separated by a spacer region of at least one kilobase pairs; and (d) a fourth DNA plasmid comprising a nucleotide sequence that encodes an adjuvant polypeptide, wherein said nucleotide sequence is operably linked to regulatory elements including a promoter and a polyadenylation signal; and (e) at least one of a pharmaceutically acceptable diluent, carrier or transfection facilitating agent. In a particular embodiment, the electroporation involves electrically stimulating the muscle with an electrical current having a field strength in the range of from about 25 V/cm to about 800 V/cm. In one embodiment, the transfection facilitating agent is bupivacaine.

In one embodiment the present invention provides an immunogenic composition for inducing an immune response to HIV in a vertebrate host, where the immunogenic composition comprises: a) a first DNA plasmid comprising a single transcriptional unit comprising a nucleotide sequence that encodes an HIV envelope polypeptide, wherein the single transcriptional unit is operably linked to regulatory elements including a promoter and a polyadenylation signal; (b) a second DNA plasmid comprising a single transcriptional unit comprising a nucleotide sequence that encodes an HIV gag-pol fusion polypeptide, wherein the single transcriptional unit is operably linked to regulatory elements including a promoter and a polyadenylation signal; (c) a third DNA plasmid comprising a single transcriptional unit comprising a nucleotide sequence that encodes an HIV nef-tat-vif fusion polypeptide, wherein the single transcriptional unit is operably linked to regulatory elements including a promoter and a polyadenylation signal; (d) a fourth DNA plasmid comprising a nucleotide sequence that encodes an adjuvant polypeptide, wherein the nucleotide sequence is operably linked to regulatory elements including a promoter and a polyadenylation signal; and (e) at least one of a pharmaceutically acceptable diluent, carrier or transfection facilitating agent. In a particular embodiment, the transfection facilitating agent is bupivacaine. In another embodiment, the immunogenic composition containing bupivacaine is administered in conjunction with electroporation. In a specific embodiment, the HIV envelope, gag-pol, nef-tat-vif and adjuvant polypeptides are expressed in a eukaryotic cell. In one embodiment, the first, second, third and fourth plasmids contain promoters that are active in eukaryotic cells.

In one embodiment the present invention provides a method of immunizing a vertebrate host against selected antigens comprising administering to the vertebrate host an immunogenic composition, wherein the immunogenic composition comprises: a) a first DNA plasmid comprising a single transcriptional unit comprising a nucleotide sequence that encodes an HIV envelope polypeptide, wherein the single transcriptional unit is operably linked to regulatory elements including a promoter and a polyadenylation signal; (b) a second DNA plasmid comprising a single transcriptional unit comprising a nucleotide sequence that encodes an HIV gag-pol fusion polypeptide, wherein the single transcriptional unit is operably linked to regulatory elements including a promoter and a polyadenylation signal; (c) a third DNA plasmid comprising a single transcriptional unit comprising a nucleotide sequence that encodes an HIV nef-tat-vif fusion polypeptide, wherein the single transcriptional unit is operably linked to regulatory elements including a promoter and a polyadenylation signal; (d) a fourth DNA plasmid comprising a nucleotide sequence that encodes an adjuvant polypeptide, wherein the nucleotide sequence is operably linked to regulatory elements including a promoter and a polyadenylation signal; and (e) at least one of a pharmaceutically acceptable diluent, carrier or transfection facilitating agent. In a particular embodiment, the transfection facilitating agent is bupivacaine. In another embodiment, the immunogenic composition containing bupivacaine is administered in conjunction with electroporation. In a specific embodiment, the HIV envelope, gag-pol, nef-tat-vif and adjuvant polypeptides are expressed in a eukaryotic cell. In one embodiment, the first, second, third and fourth plasmids contain promoters that are active in eukaryotic cells.

In certain embodiments of the invention, the first, second, third and fourth plasmids contain promoters that are selected from the group consisting of human cytomegalovirus (HCMV) immediate early promoter, the simian cytomegalovirus (SCMV) promoter, the murine cytomegalovirus (MCMV) promoter, the herpes simplex virus (HSV) latency-associated promoter-1 (LAP1), Simian virus 40 promoter, human elongation factor 1 alpha promoter, and the human muscle cell specific desmin promoter. In certain embodiments of the invention, the first, second, third and fourth plasmids contain polyadenylation signals that are selected from the group consisting of rabbit beta-globin poly(A) signal, synthetic polyA, HSV Thymidine kinase poly A, Human alpha globin poly A, SV40 poly A, human beta globin poly A, polyomavirus poly A, and Bovine growth hormone poly A.

In a particular embodiment, the present invention provides an immunogenic composition for inducing an immune response to HIV in a vertebrate host, where the immunogenic composition comprises four plasmids as described above, and where each plasmid further comprises a selectable marker selected from the group consisting of kanamycin resistance gene, ampicillin resistance gene, tetracycline resistance gene, hygromycin resistance gene and chloroamphenicol resistance gene. In another embodiment, each plasmid further comprises a bacterial origin of replication. In still another embodiment, the origin of replication is the pUC origin of replication.

The invention also provides an immunogenic composition, and wherein the fourth DNA plasmid comprises a primary transcriptional unit and a secondary transcriptional unit comprising two nucleotide sequences that encode two adjuvant polypeptides operably linked to regulatory elements. In one embodiment, the primary transcriptional unit comprises a nucleotide sequence that encodes an IL-12 p35 polypeptide operably linked to regulatory elements including a promoter and a polyadenylation signal. In another embodiment, the secondary transcriptional unit comprises a nucleotide sequence that encodes an IL-12 p40 polypeptide operably linked to regulatory elements including a promoter and a polyadenylation signal.

In another embodiment the present invention provides an immunogenic composition for inducing an immune response to HIV in a vertebrate host, where the immunogenic composition comprises: (a) a first DNA plasmid comprising a single transcriptional unit comprising a nucleotide sequence that encodes an HIV envelope polypeptide, wherein the single transcriptional unit is operably linked to regulatory elements including a promoter and a polyadenylation signal; (b) a second DNA plasmid comprising a single transcriptional unit comprising a nucleotide sequence that encodes an HIV gag polypeptide, wherein the single transcriptional unit is operably linked to regulatory elements including a promoter and a polyadenylation signal; (c) a third DNA plasmid comprising a single transcriptional unit comprising a nucleotide sequence that encodes an HIV pol polypeptide, wherein the single transcriptional unit is operably linked to regulatory elements including a promoter and a polyadenylation signal; (d) a fourth DNA plasmid comprising a single transcriptional unit comprising a nucleotide sequence that encodes an HIV nef-tat-vif fusion polypeptide, wherein said single transcriptional unit is operably linked to regulatory elements including a promoter and a polyadenylation signal; (e) a fifth DNA plasmid comprising a nucleotide sequence that encodes an adjuvant polypeptide, wherein said nucleotide sequence is operably linked to regulatory elements including a promoter and a polyadenylation signal; and (f) at least one of a pharmaceutically acceptable diluent, carrier or transfection facilitating agent. In a specific embodiment, the transfection facilitating agent is bupivacaine. In another embodiment, the immunogenic composition containing bupivacaine is administered in conjunction with electroporation. In one embodiment, the HIV envelope, gag, pol, nef-tat-vif and adjuvant polypeptides are expressed in a eukaryotic cell.

In another embodiment the present invention provides a method of immunizing a vertebrate host against selected antigens comprising administering to said vertebrate host an immunogenic composition where the immunogenic composition comprises: (a) a first DNA plasmid comprising a single transcriptional unit comprising a nucleotide sequence that encodes an HIV envelope polypeptide, wherein the single transcriptional unit is operably linked to regulatory elements including a promoter and a polyadenylation signal; (b) a second DNA plasmid comprising a single transcriptional unit comprising a nucleotide sequence that encodes an HIV gag polypeptide, wherein the single transcriptional unit is operably linked to regulatory elements including a promoter and a polyadenylation signal; (c) a third DNA plasmid comprising a single transcriptional unit comprising a nucleotide sequence that encodes an HIV pol polypeptide, wherein the single transcriptional unit is operably linked to regulatory elements including a promoter and a polyadenylation signal; (d) a fourth DNA plasmid comprising a single transcriptional unit comprising a nucleotide sequence that encodes an HIV nef-tat-vif fusion polypeptide, wherein said single transcriptional unit is operably linked to regulatory elements including a promoter and a polyadenylation signal; (e) a fifth DNA plasmid comprising a nucleotide sequence that encodes an adjuvant polypeptide, wherein said nucleotide sequence is operably linked to regulatory elements including a promoter and a polyadenylation signal; and (f) at least one of a pharmaceutically acceptable diluent, carrier or transfection facilitating agent. In a specific embodiment, the transfection facilitating agent is bupivacaine. In another embodiment, the immunogenic composition containing bupivacaine is administered in conjunction with electroporation.

In one embodiment of the invention the first, second, third, fourth and fifth plasmids contain promoters that are active in eukaryotic cells. In certain embodiments, the first, second, third, fourth and fifth plasmids contain promoters that are selected from the group consisting of human cytomegalovirus (HCMV) immediate early promoter, the simian cytomegalovirus (SCMV) promoter, the murine cytomegalovirus (MCMV) promoter, and the herpes simplex virus (HSV) latency-associated promoter-1 (LAP1), Simian virus 40 promoter, human elongation factor 1 alpha promoter, and the human muscle cell specific desmin promoter. In other embodiments of the invention, the first, second, third and fourth plasmids contain polyadenylation signals that are selected from the group consisting of rabbit beta-globin poly (A) signal, synthetic polyA, HSV Thymidine kinase poly A, Human alpha globin poly A, SV40 poly A, human beta globin poly A, polyomavirus poly A, and Bovine growth hormone poly A.

In a particular embodiment, the present invention provides an immunogenic composition for inducing an immune response to HIV in a vertebrate host, where the immunogenic composition comprises five plasmids as described above, and where each plasmid further comprises a selectable marker selected from the group consisting of kanamycin resistance gene, ampicillin resistance gene, tetracycline resistance gene, hygromycin resistance gene and chloroamphenicol resistance gene. In another embodiment, each plasmid further comprises a bacterial origin of replication and wherein the origin of replication is the pUC origin of replication.

The invention also provides an immunogenic composition, and wherein the fifth DNA plasmid comprises a primary transcriptional unit and a secondary transcriptional unit comprising two nucleotide sequences that encode two adjuvant polypeptides operably linked to regulatory elements. In one embodiment, the primary transcriptional unit comprises a nucleotide sequence that encodes an IL-12 p35 polypeptide operably linked to regulatory elements including a promoter and a polyadenylation signal. In another embodiment, the secondary transcriptional unit comprises a nucleotide sequence that encodes an IL-12 p40 polypeptide operably linked to regulatory elements including a promoter and a polyadenylation signal.

Other aspects and embodiment of the present invention are disclosed in the following detailed description.

BRIEF DESCRIPTION OF THE DRAWINGS

FIG. 1 shows a linear but more detailed schematic diagram of the same plasmid. The following abbreviations are used: SCMV: Simian cytomegalavirus promoter, HCMV: Human cytomegalovirus promoter, BGH-polyA: Bovine growth hormone poly adenylation signal, kan: Kanamycin marker gene for resistance, HSVlap1: Herpes simplex virus latency-associated promoter 1, SV40 polyA: Simian virus 40 poly adenylation signal SV40sd/sa: Simian virus 40 splice donor and acceptor, gag-pol: HIV gag-pol fusion, ntv: HIV nef-tat-vif fusion, env: HIV envelope.

| Lane | Plasmid Combinations Transfected |
| --- | --- |
| 1 | 301 (gag/pol) + 101 (env) + 104 (ntv) |
| 2 | 201 (gag, pol) + 202 (env, ntv) |
| 3 | 203 (gag/pol/ntv, env) |
| 4 | 303 (gag/pol, env, ntv) |
| 5 | 101 (env) + 102 (gag) + 103 (pol) + 104 (ntv) |
| 6 | 001 (control) |

Figure 7:
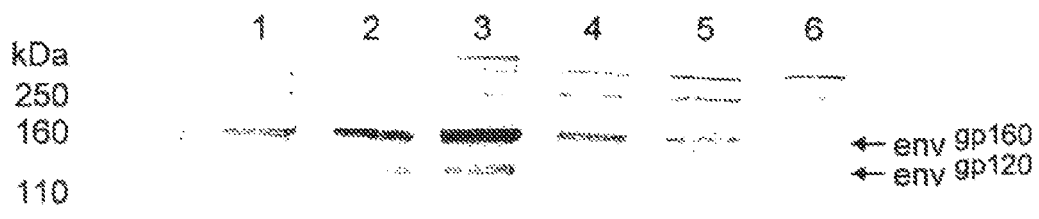

FIG. 7 shows HIV env expression in 293 cells. 293 cells were transfected with 1 µg of indicated plasmid DNA combination. Forty-eight hours after transfections, cell associated HIV proteins were visualized by Western blot. The promoters and open reading frames for a particular plasmid are shown below:

| Lane | Plasmid Combinations Transfected |
| --- | --- |
| 1 | 152 (gag/pol) + 101 (env) + 104 (ntv) |
| 2 | 201 (gag, pol) + 202 (env, ntv) |
| 3 | 203 (gag/pol/ntv, env) |
| 4 | 303 (gag/pol, env, env) |
| 5 | 101 (env) + 102 (gag) + 103 (pol) + 104 (ntv) |
| 6 | 001 (control) |

Figure 8:
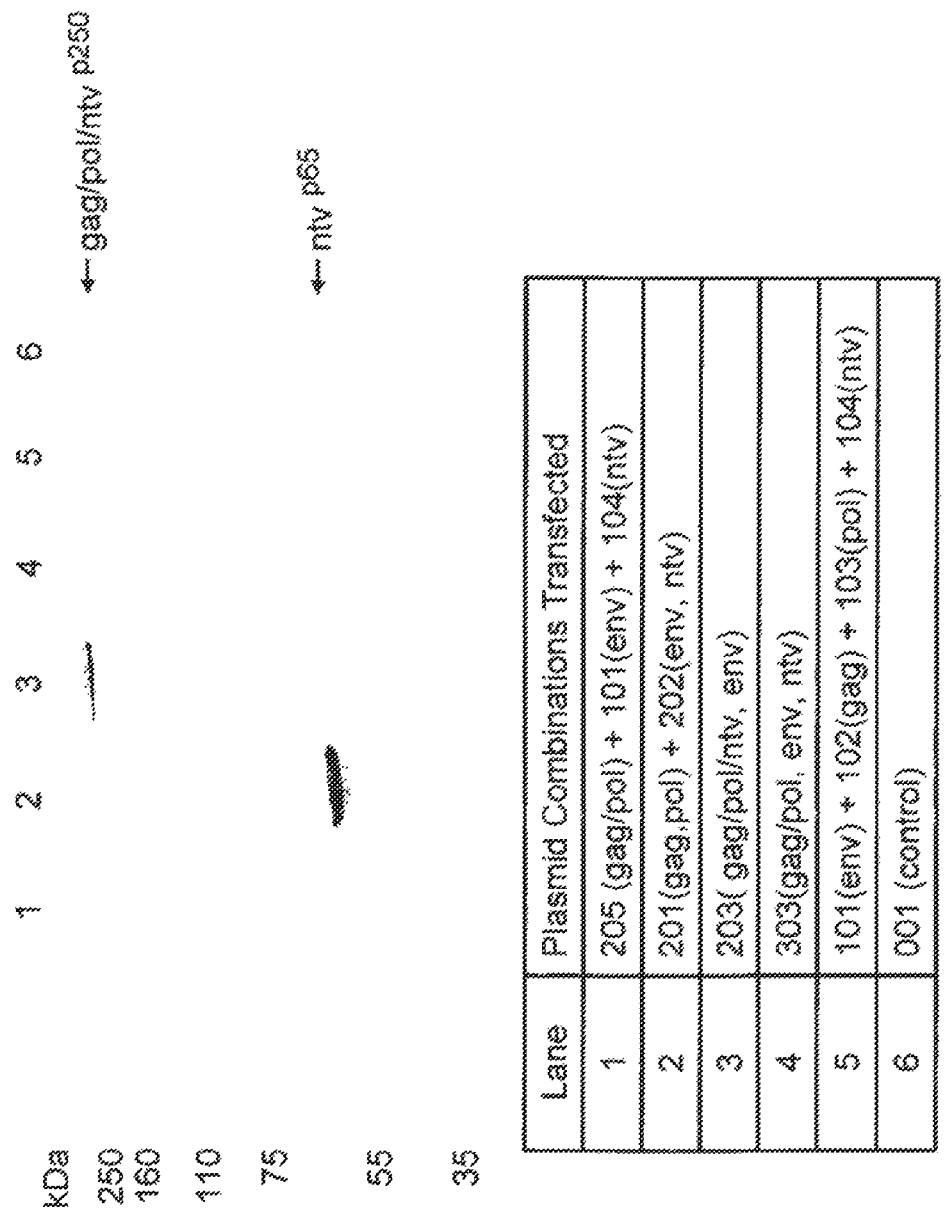

FIG. 8 shows HIV ntv expression in 293 cells. 293 cells were transfected with 1 µg of indicated plasmid DNA combination. Forty-eight hours after transfections, cell associated HIV proteins were visualized by Western blot. The promoters and open reading frames for a particular plasmid are shown below:

| Lane | Plasmid Combinations Transfected |
|---|---|
| 1 | 152 (gag/pol) + 101 (env) + 104 (ntv) |
| 2 | 201 (gag, pol) + 202 (env, ntv) |
| 3 | 203 (gag/pol/ntv, env) |
| 4 | 303 (gag/pol, env, env) |
| 5 | 101 (env) + 102 (gag) + 103 (pol) + 104 (ntv) |
| 6 | 001 (control) |

Figure 9:
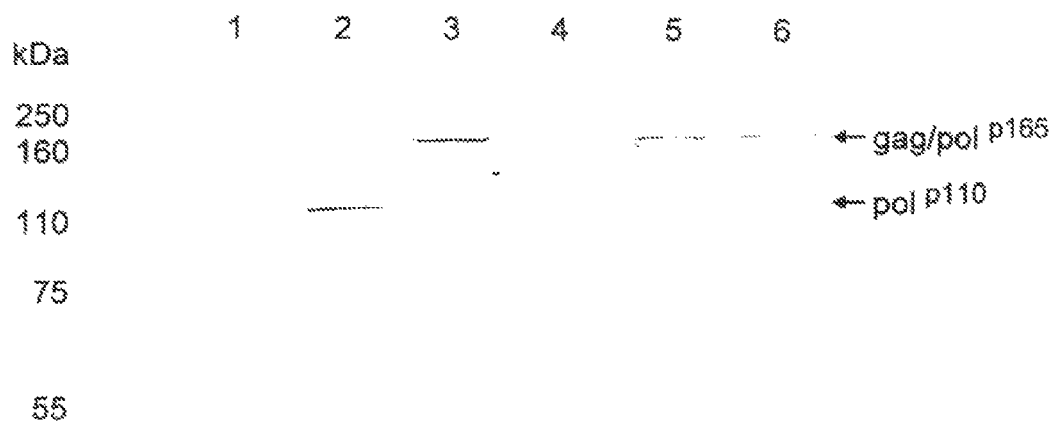

FIG. 9 shows HIV pol expression in 293 cells. 293 cells were transfected with the indicated plasmid DNA concentration and combination. Forty-eight hours after transfections, cell associated HIV proteins were visualized by Western blot. The promoters and open reading frames for a particular plasmid are shown below:

| Lane | Plasmid Combinations Transfected | Plasmid concentration Transfected (micrograms) |
|---|---|---|
| 1 | 001 (control) | 2 |
| 2 | 201 (gag, pol) + 202 (ntv, env) | 1 + 1 |
| 3 | 204 (gag/pol, env) + 104 (ntv) | 1 + 1 |
| 4 | 203 (gag/pol/ntv, env) | 2 |
| 5 | 302 (gag/pol, ntv) + 101 (env) | 1 + 1 |
| 6 | 303 ((gag/pol, env, ntv) | 2 |

Figure 10:
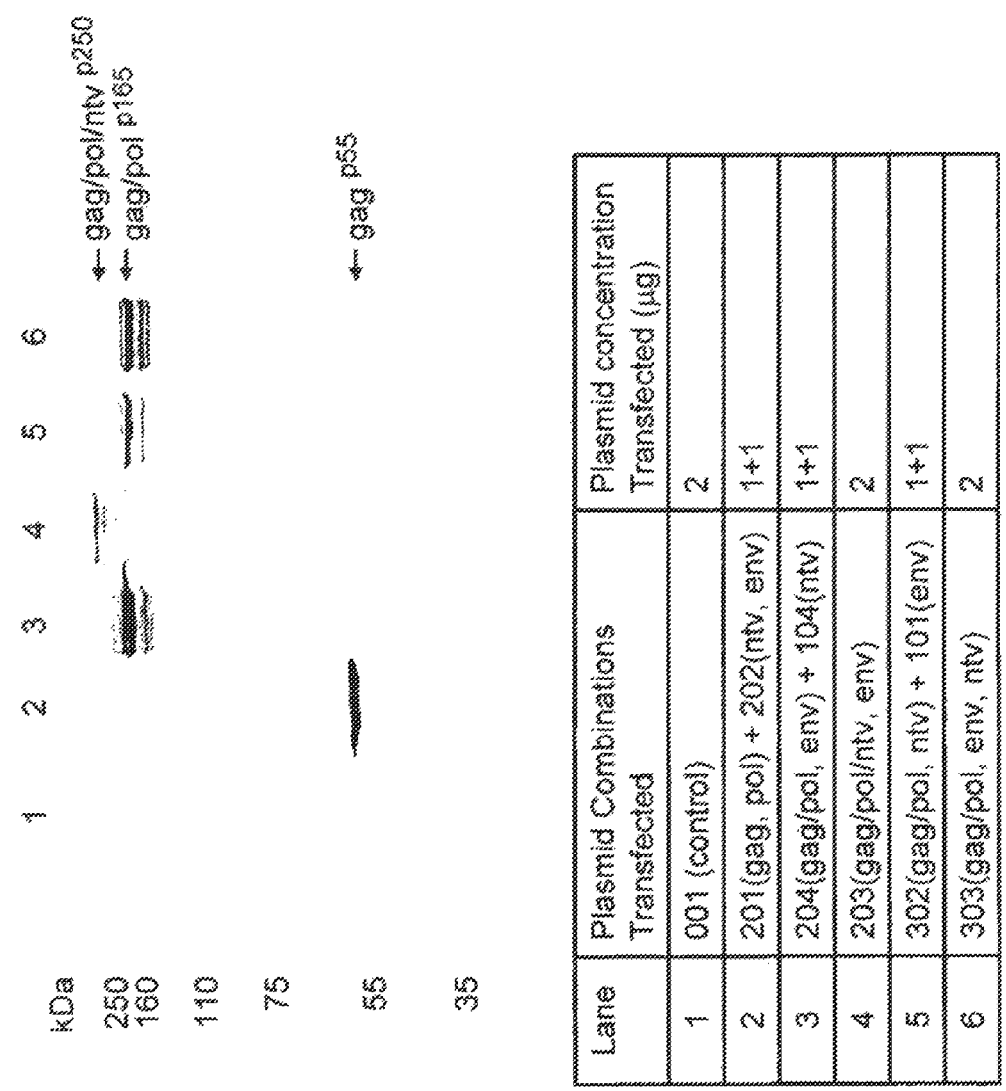

FIG. 10 shows HIV gag expression in 293 cells. 293 cells were transfected with the indicated plasmid DNA concentration and combination. Forty-eight hours after transfections, cell associated HIV proteins were visualized by Western blot. The promoters and open reading frames for a particular plasmid are shown below:

| Lane | Plasmid Combinations Transfected | Plasmid concentration Transfected (micrograms) |
|---|---|---|
| 1 | 001 (control) | 2 |
| 2 | 201(gag, pol) + 202(ntv, env) | 1 + 1 |
| 3 | 204(gag/pol, env) + 104(ntv) | 1 + 1 |
| 4 | 203(gag/pol/ntv, env) | 2 |
| 5 | 302(gag/pol, ntv) + 101(env) | 1 + 1 |
| 6 | 303((gag/pol, env, ntv) | 2 |

Figure 11:
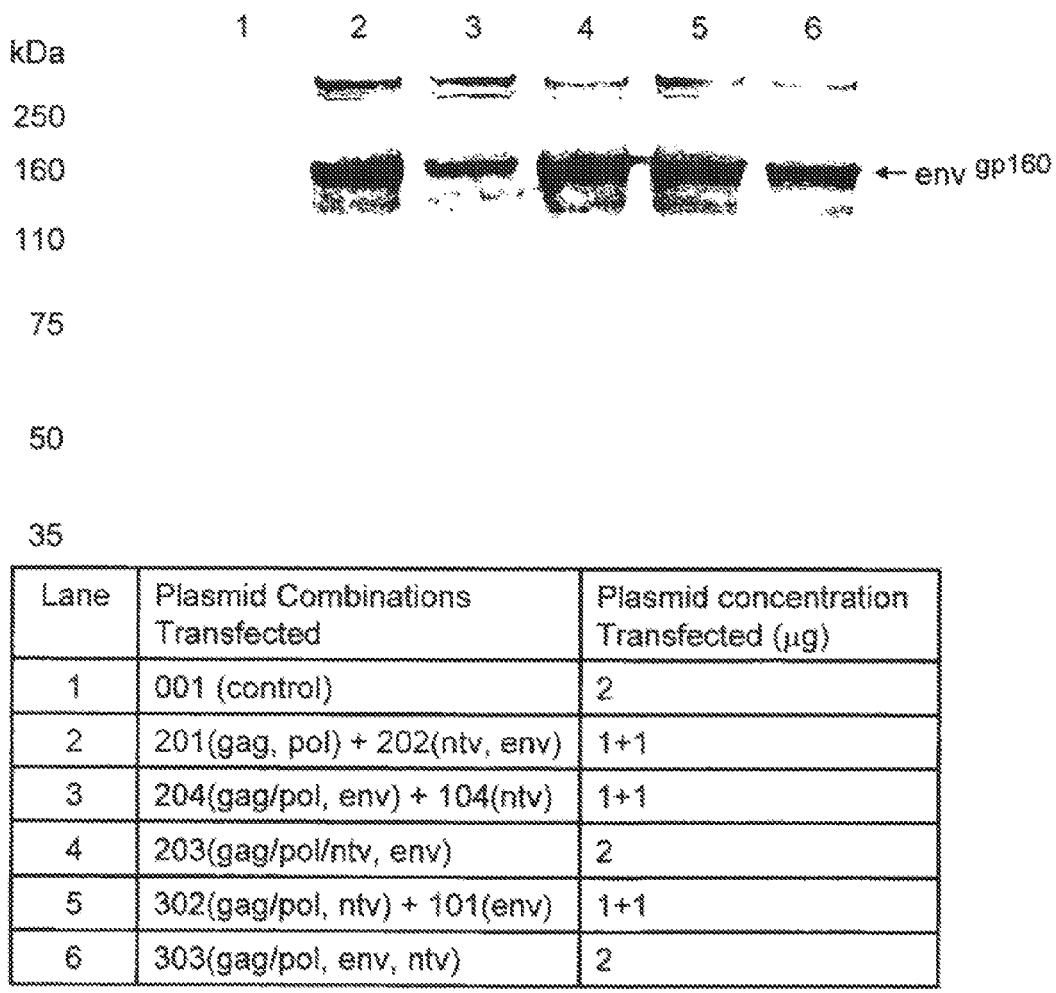

FIG. 11 shows HIV env Expression in 293 Cells. 293 cells were transfected with the indicated plasmid DNA concentration and combination. Forty-eight hours after transfections, cell associated HIV proteins were visualized by Western blot. The promoters and open reading frames for a particular plasmid are shown below:

| Lane | Plasmid Combinations Transfected | Plasmid concentration Transfected (micrograms) |
|---|---|---|
| 1 | 001 (control) | 2 |
| 2 | 201(gag, pol) + 202(ntv, env) | 1 + 1 |
| 3 | 204(gag/pol, env) + 104(ntv) | 1 + 1 |
| 4 | 203(gag/pol/ntv, env) | 2 |
| 5 | 302(gag/pol, ntv) + 101(env) | 1 + 1 |
| 6 | 303((gag/pol, env, ntv) | 2 |

Figure 12:
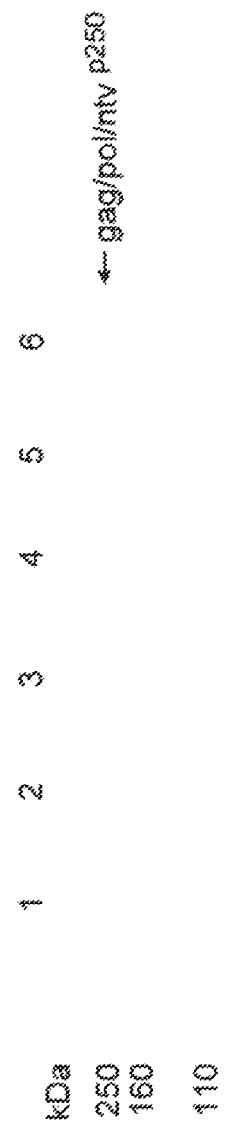

FIG. 12 shows HIV ntv expression in 293 cells. 293 cells were transfected with the indicated plasmid DNA concentration and combination. Forty-eight hours after transfections, cell associated HIV proteins were visualized by Western blot. The promoters and open reading frames for a particular plasmid are shown below:

| Lane | Plasmid Combinations Transfected | Plasmid concentration Transfected (micrograms) |
|---|---|---|
| 1 | 001 (control) | 2 |
| 2 | 201(gag, pol) + 202(ntv, env) | 1 + 1 |
| 3 | 204(gag/pol, env) + 104(ntv) | 1 + 1 |
| 4 | 203(gag/pol/ntv, env) | 2 |
| 5 | 302(gag/pol, ntv) + 101(env) | 1 + 1 |
| 6 | 303((gag/pol, env, ntv) | 2 |

DETAILED DESCRIPTION OF THE INVENTION

DNA based immunogenic compositions provide an alternative to traditional immunogenic compositions comprising administration of protein antigens and an adjuvant. Instead, DNA based immunogenic compositions involve the introduction of DNA, which encodes the antigen or antigens, into tissues of a subject, where the antigens are expressed by the cells of the subject's tissue. As used herein, such immunogenic compositions are termed "DNA based immunogenic compositions" or "nucleic acid-based immunogenic compositions." One problem has been that when multiple genes are required for generation of a protective immune response, multiple plasmids have had to be used to individually express the genes. This imposes manufacturing and regulatory burdens. Embodiments of the present invention provide solutions to this problem with a plasmid design capable of expressing three independent open reading frames in the same cell. In certain embodiments of the invention, genes are fused to make polyproteins and, in this way, many more proteins can be can be expressed from a single plasmid. In one embodiment, six proteins are expressed from the single plasmid.

A large number of factors can influence the expression of antigen genes and/or the immunogenicity of DNA based immunogenic compositions. Examples of such factors include the construction of the plasmid vector, size of the plasmid vector, choice of the promoter used to drive antigen gene expression, the number and size of transcriptional units on the plasmid, stability of the RNA transcripts, orientation of the transcriptional units within the plasmid, reproducibility of immunization and stability of the inserted gene in the plasmid. Embodiments of the present invention provide plasmid designs that optimize many of these key parameters.

The design and optimization of plasmid DNA vectors having multiple transcriptional units is critical. To improve the actual dose of antigen received by an immunized subject, the size of the plasmid must be minimized, while the number of protein products and quantity of protein produced should be maximized. To balance these considerations, one must consider placement of genes; spacing of transcriptional units; direction of transcription of the open reading frames; levels of expression; promoter size, orientation and strength; enhancer size, placement, orientation and strength; open reading frame size and organization; ease of manufacture; plasmid stability; safety; and the ultimate dose of the vector necessary to immunize the subject.

An important consideration with the use of DNA plasmids for immunization is manufacture of the plasmid. Due to potential safety concerns, the manufacturing process and the final products must undergo intense scrutiny and be subject to extensive quality control. The result is reflected in high costs for such procedures. As a result, any DNA immunization, which requires multiple plasmids, will be proportionately more expensive and less likely to be effective. Therefore, in certain embodiments of the present invention, where manufacturing costs need to be controlled, immunogenic compositions are provided comprising a single plasmid per application suitable to induce immune responses in virtually any disease process.

In some situations, in spite of higher manufacturing costs, the use of combinations of plasmids each containing a single transcriptional unit or two transcriptional units may lead to a more effective immunogenic composition. In such cases, it is important to design the immunogenic composition to have the optimal number of plasmids encoding all of the genes necessary for inducing an effective immune response. The use of a plasmid containing three transcriptional units expressing all of the necessary genes instead of multiple plasmids each containing a single transcriptional unit must be balanced with the immunogenicity of particular antigens. One advantage of the combination of single transcriptional unit plasmids approach is that the individual genes may each be driven by the same strong promoter. For example, the HCMV promoter can be used in each plasmid, rather than only once per plasmid, as is the case in a three transcriptional unit plasmid. In contrast, when using a three transcriptional plasmid, the HCMV promoter can only be used once to prevent the possibility of internal homologous recombination and plasmid instability. For example, in a composition having two antigen expressing plasmids where one plasmid has one transcriptional unit and the second has two transcriptional units. In such a composition, HCMV promoter may be used to drive expression of the single antigen or fusion protein in the plasmid with one transcriptional unit and it may also be used to drive expression of one of the proteins or fusion proteins in the plasmid having two transcriptional units.

In the case where the pathogen is human immunodeficiency virus (HIV), immunogenic compositions are described with four single transcriptional unit plasmids which contain nucleotide sequences encoding, respectively, an HIV envelope polypeptide, an HIV gag-pol fusion polypeptide, an HIV nef-tat-vif fusion polypeptide, and an adjuvant polypeptide. If desired, two single transcriptional unit plasmids may be used which contain nucleotide sequences encoding, respectively, an HIV gag polypeptide and an HIV pol fusion polypeptide, instead of the single transcriptional unit plasmid containing a nucleotide sequence encoding an HIV gag-pol fusion polypeptide (thus, in this aspect, five plasmids are used).

In general, depending on their origin, promoters differ in tissue specificity and efficiency in initiating mRNA synthesis [Xiang et al., Virology, 209:564-579 (1994); Chapman et al., Nucle. Acids. Res., 19:3979-3986 (1991)]. To date, most DNA based immunogenic compositions in mammalian systems have relied upon viral promoters derived from cytomegalovirus (CMV). The CMV may be human or simian in origin. These have had good efficiency in both muscle and skin immunization in a number of mammalian species. Another factor known to affect the immune response elicited by DNA immunization is the method of DNA delivery; parenteral routes can yield low rates of gene transfer and produce considerable variability of gene expression. See Montgomery et al., DNA Cell Bio., 12:777-783 (1993). High-velocity inoculation of plasmids, using a gene-gun, enhanced the immune responses of mice, presumably because of a greater efficiency of DNA transfection and more effective antigen presentation by dendritic cells. See Fynan et al., Proc. Natl. Acad. Sci., 90:11478-11482 (1993B); Eisenbraun et al., DNA Cell Biol., 12: 791-797 (1993). Vectors containing the nucleic acid-based immunogenic composition of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter. See, e.g., Wu et al., J. Biol. Chem. 267:963-967 (1992); Wu and Wu, J. Biol. Chem. 263: 14621-14624 (1988); Hartmut et al., Canadian Patent Application No. 2,012,311, filed Mar. 15, 1990.

Accordingly, the present invention relates to plasmids, immunogenic compositions and methods for the genetic immunization of vertebrates such as mammals, birds and fish. The plasmids, immunogenic compositions and methods of the present invention can be particularly useful for mammalian subjects including human, bovine, ovine, porcine, equine, canine and feline species. The plasmids, immunogenic compositions and methods are described in detail below and with reference to the cited documents that are incorporated by reference to provide detail known to one of skill in the art.

A. DNA Plasmids, Vectors, Constructs, Immunogenic Compositions

The terms plasmid, construct and vector are used throughout the specification. As used herein, the term "plasmid" refers to a circular, supercoiled DNA molecule into which various nucleic acid molecules coding for regulatory sequences, open reading frames, cloning sites, stop codons, spacer regions or other sequences selected for structural or functional regions are assembled and used as a vector to express genes in a vertebrate host. Further, as used herein, "plasmids" are capable of replicating in a bacterial strain. As used herein, the term "construct" refers to a particular vector or plasmid having a specified arrangement of genes and regulatory elements. A nucleic acid sequence can be "exogenous," which means that it is foreign to the cell into which the vector is being introduced, "heterologous" which means that it is derived from a different genetic source or "homologous", which means that the sequence is structurally related to a sequence in the cell but in a position within the host cell nucleic acid in which the sequence is ordinarily not found. One of skill in the art would be well equipped to construct a vector or modify a plasmid of the invention through standard recombinant techniques, which are described in See, e.g., Sambrook et al, *Molecular Cloning. A Laboratory Manual*, Cold Spring Harbor Laboratory, New York, (1989) and references cited therein at, for example, pages 3.18-3.26 and 16.17-16.27 and Ausubel et al., *Current Protocols in Molecular Biology*, Wiley Interscience Publishers, New York (1995) both incorporated herein by reference.

The term "vector" is used to refer to a carrier nucleic acid molecule into which a designated nucleic acid molecule encoding an antigen or antigens can be inserted for introduction into a cell where it can be expressed. Vectors include plasmids, cosmids, viruses (bacteriophage, animal viruses, and plant viruses), and artificial chromosomes (e.g., YACs). The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of expressed interfering RNA (eiRNA), short interfering RNA (siRNA), antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described below.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g. genomic or cDNA), but may be synthetically produced (e.g. produced by oligonucleotide synthesis).

The phrase "each derived from different transcriptional units", as used herein means that each of the regulatory control elements of a similar function, such as the promoters, are all of different origin and are not homologous to each other to such a level that genetic instability through recombination may arise in the plasmid. See Herrera et al., *Biochem. Biophys. Res. Commun.* 279:548-551 (2000).

Immunogenic compositions of this invention include a triple transcriptional unit DNA plasmid comprising a DNA sequence encoding at least three selected antigens to which an immune response is desired. In the plasmid, the selected antigens are under the control of regulatory sequences directing expression thereof in a mammalian or vertebrate cell. Immunogenic compositions of this invention also include combinations of plasmids encoding selected antigens. Such combinations may be comprised of two, three or four plasmids encoding additional selected antigens. There may be one, two, or three transcriptional units on any particular plasmid within the combination. Furthermore, additional plasmids encoding adjuvant polypeptides may be included in the immunogenic compositions of the invention.

Non-viral, plasmid vectors useful in this invention contain isolated and purified DNA sequences comprising DNA sequences that encode the selected immunogen and antigens. The DNA molecule encoding the target antigens may be derived from viral or non-viral sources such as bacterial species or tumor antigens that have been designed to encode an exogenous or heterologous nucleic acid sequence. Such plasmids or vectors can include sequences from viruses or phages. A variety of non-viral vectors are known in the art and may include, without limitation, plasmids, bacterial vectors, bacteriophage vectors, "naked" DNA, DNA condensed with cationic lipids or polymers, as well as DNA formulated with other transfection facilitating agents, for example the local anesthetic such as bupivacaine, discussed below.

Components of the plasmids of this invention may be obtained from existing vectors. Examples of bacterial vectors include, but are not limited to, sequences derived from bacille Calmette Guérin (BCG), *Salmonella, Shigella, E. coli*, and *Listeria*, among others. Suitable plasmid vectors for obtaining components include, for example, pBR322, pBR325, pACYC177, pACYC184, pUC8, pUC9, pUC18, pUC19, pLG339, pR290, pK37, pKC101, pAC105, pVA51, pKH47, pUB110, pMB9, pBR325, Col E1, pSC101, pBR313, pML21, RSF2124, pCR1, RP4, pBAD18, and pBR328.

Other components may be obtained from inducible expression vectors. Examples of suitable inducible *Escherichia coli* expression vectors include pTrc (Amann et al., *Gene*, 69:301-315 (1988)), the arabinose expression vectors (e.g., pBAD18, Guzman et al, *J. Bacteriol.*, 177:4121-4130 (1995)), and pETIId (Studier et al., *Methods in Enzymology*, 185:60-89 (1990)). Target gene expression from the pTrc vector relies on host RNA polymerase transcription from a hybrid trp-lac fusion promoter. Target gene expression from the pETIId vector relies on transcription from a T7 gn10-lac fusion promoter mediated by a coexpressed viral RNA polymerase T7 gn I. This viral polymerase is supplied by host strains BL21 (DE3) or HMS I74(DE3) from a resident prophage harboring a T7 gn1 gene under the transcriptional control of the lacUV5 promoter. The pBAD system relies on the inducible arabinose promoter that is regulated by the araC gene. The promoter is induced in the presence of arabinose.

Regulatory components may be obtained from inducible promoters that are regulated by exogenously supplied compounds, including, the zinc-inducible sheep metallothionine (MT) promoter, the dexamethasone (Dex) inducible mouse mammary tumor virus (MMTV) promoter, the tetracycline inducible system (Gossen et al, *Science* 268:1766-1769 (1995) and the repamycin inducible system (Magari et al, *J clin Invest*, 100:2865-2872 (1997)).

Transcriptional control signals in eukaryotes are comprised of promoter and enhancer elements. "Promoters" and "enhancers" as used herein refer to DNA sequences that interact specifically with proteins involved in transcription. See Maniatis, T., et al., *Science* 236:1237 (1987). As discussed above 5'-untranslated regions may be combined with promoters and enhancers to enhance expression of the selected antigens. The promoter, enhancers and other regulatory sequences that drive expression of the antigen in the desired mammalian or vertebrate subject may similarly be selected from a wide list of promoters known to be useful for that purpose. A variety of such promoters are disclosed below. In an embodiment of the immunogenic DNA plasmid composition described below, useful promoters are the human cytomegalovirus (HCMV) promoter/enhancer (described in, e.g., U.S. Pat. Nos. 5,158,062 and 5,385,839, incorporated herein by reference), the human herpes virus latency-associated promoters 1 and 2 (HSVLap1 & HSVLap2: sometimes referred to as "latency-active promoters 1 & 2") and the simian cytomegalovirus (SCMV) promoter enhancer. See Goins W. F. et al., *J. Virology* 68:2239-2252 (1994); Soares, K. J. et al., *Virology* 70:5384-5394; Goins W. F. et al., *J. Virology* 73:519-532 (1999). The murine cytomegalovirus (MCMV) promoter is also suitable for use.

Other useful transcriptional control elements include post-transcriptional control elements such as the constitutive transport enhancers (CTE) or CTE-like elements such as RNA transport elements (RTE), which aid in transport of unspliced or partially spliced RNA to the cytoplasm. See U.S. Pat. No. 5,585,263 to Hammarskjold et al., and Zolotukhin et al., *J. Virol.* 68:944-7952 (1994)). CTE or RTE are desirable because they have been shown to improve expression, and because many genes require the presence of post-transcriptional control elements. There are several types of CTE and CTE-like elements, which function using different pathways. See Tabernero et al., *J. Virol.* 71:95-101 (1997). See also International application WO 99/61596, which describes a new type of post-transcriptional control element that is able to replace CTE.

Gene expression can also be enhanced by the inclusion of polynucleotide sequences that function at the level of supporting mRNA accumulation, increasing mRNA stability or through the facilitation of ribosome entry all of which mechanisms produce greater levels of translation. In particular embodiments of the invention, certain 5' untranslated regions and introns can be combined with promoters and enhancers to produce composite or chimeric promoters capable of driving higher levels of gene expression.

Examples of 5' untranslated regions useful for enhancing gene expression include the adenovirus tripartite leader sequence (Adtp) which can be inserted downstream of a promoter to increase the expression of a of a gene or transgene by enhancing translation, without modifying the specificity of the promoter. See W. Sheay et al., Biotechniques 15(5): 856-62 (1993). The 5'UTR of the chimpanzee and mouse elongation factor 1 alpha (EF-1α) mRNAs contains an intron known to enhance the gene expression through increasing RNA transcription and/or RNA stability. See S. Y. Kim et al., J Biotechnol. 14; 93(2):183-7 (1993). The 5'-UTR of the mRNA encoding the eukaryotic initiation factor 4g (eIF4g) is characterized by the presence of a putative internal ribosome entry site (IRES) and displays a strong promoter activity. See B. Han B. & J. T. Zhang Mol Cell Biol 22(21):7372-84 (2002). In addition, the 5'UTR of human heat shock protein 70 (Hsp70) mRNA contains an element that increases the efficiency of mRNA translation under normal cell culture conditions by up to an order of magnitude. See S. Vivinus et al., Eur J Biochem. 268(7):1908-17 (2001). The 5'UTR of the NF-kappaB Repressing Factor acts as a potent IRES and also functions as a translational enhancer in the context of monocistronic mRNAs. See A. Oumard et al., Mol Cell Biol. 20(8): 2755-9 (2000). When associated and added between the CAP and the initiation codon, the SV40 5'UTR and the R region from human T cell leukemia virus (HTLV) Type 1 Long Terminal Repeat (SUR) increase translation efficiency possibly through mRNA stabilization. See Y. Takebe et al., Mol Cell Biol. 8(1):466-472) (1988).

In particular embodiments of the invention, regulatory sequences for inclusion in a nucleic acid molecule, DNA plasmid or vector of this invention include, without limitation, a promoter sequence, an enhancer sequence, 5' untranslated region sequence, intron, CTE, RTE, a polyadenylation sequence, a splice donor sequence and a splice acceptor sequence, a site for transcription initiation and termination positioned at the beginning and the end, respectively, of the gene to be translated, a ribosome binding site for translation in the transcribed region, an epitope tag, a nuclear localization sequence, an internal ribosome entry site (IRES) element, a Goldberg-Hogness "TATA" element, a restriction enzyme cleavage site, a selectable marker and the like. Enhancer sequences include, e.g., the 72 bp tandem repeat of SV40 DNA or the retroviral long terminal repeats or LTRs, etc. and are employed to increase transcriptional efficiency. See Wasylyk, et al., Nucleic Acid Res. 12:5589-5608 (1984).

These other components useful in DNA plasmids, including, e.g., origins of replication, polyadenylation sequences (e.g., bovine growth hormone (BGH) polyA, simian virus 40 (SV40) polyA), drug resistance markers (e.g., kanamycin resistance), and the like, may also be selected from among widely known sequences, including those described in the examples and mentioned specifically below.

Selection of individual promoters and other common plasmid elements are conventional and many such sequences are available with which to design the plasmids useful in this invention. See, e.g., Sambrook et al, *Molecular Cloning. A Laboratory Manual*, Cold Spring Harbor Laboratory, New York, (1989) and references cited therein at, for example, pages 3.18-3.26 and 16.17-16.27 and Ausubel et al., *Current Protocols in Molecular Biology*, John Wiley & Sons, New York (1989). All components of the plasmids useful in this invention may be readily selected by one of skill in the art from among known materials in the art and available from the pharmaceutical industry.

Examples of suitable genes, which express antigens or polypeptides, are identified in the discussion below. In one embodiment of the plasmids and immunogenic compositions herein, the selected antigens are HIV-1 antigens, including those expressed by the gag, pol, env, nef, vpr, vpu, vif and tat genes. In one embodiment, the coding and noncoding sequence and other components of the DNA plasmid are optimized, such as by codon selection appropriate to the intended host and by removal of any inhibitory sequences, also discussed below with regard to antigen preparation.

According to embodiments of the present invention, a composition contains one plasmid expressing at least three selected antigens. Alternatively, the plasmid composition also comprises one DNA plasmid comprising a DNA sequence encoding at least three copies of the same selected antigen or polypeptide of interest. In one embodiment of the present invention, a composition may contain one plasmid expressing multiple selected antigens from multiple open reading frames. In another embodiment, the plasmid composition comprises one DNA plasmid comprising a DNA sequence encoding multiple copies of similar open reading frames encoding multiple selected antigens, for example multiple env genes from different clades.

In a particular embodiment of the invention, the use of combinations of plasmids, each expressing a single antigen, may lead to a more effective immunogenic composition. For example, in one embodiment, the present invention provides an immunogenic composition where the immunogenic composition contains four plasmids, each encoding an HIV immunogen or an adjuvant. One such specific immunogenic composition contains the following combination of four plasmids: (a) a first DNA plasmid that has a single transcriptional unit with a nucleotide sequence that encodes an HIV envelope polypeptide; (b) a second DNA plasmid that has a single transcriptional unit with a nucleotide sequence that encodes an HIV gag-pol fusion polypeptide; (c) a third DNA plasmid that has a single transcriptional unit with a nucleotide sequence that encodes an HIV nef-tat-vif fusion polypeptide; (d) a fourth DNA plasmid that has a nucleotide sequence that encodes an adjuvant polypeptide; and (e) at least one of a pharmaceutically acceptable diluent, carrier or transfection facilitating agent. In a specific embodiment, the promoter driving the expression of each of the HIV genes is the HCMV promoter and the polyA sequence for each of the HIV genes is the bovine growth hormone polyA.

In a specific embodiment of the invention, where the use of combinations of plasmids each expressing a single antigen is desired, it may be advantageous to use more plasmids containing more individual genes encoding individual polypeptides and fewer fusion genes encoding fusion polypeptides. For example, in one embodiment the present invention provides an immunogenic composition where the immunogenic composition contains five plasmids each encoding and an HIV immunogen or an adjuvant. In this embodiment, the immunogenic composition comprises: (a) a first DNA plasmid that has a single transcriptional unit with a nucleotide sequence that encodes an HIV envelope polypeptide; (b) a second DNA plasmid that has a single transcriptional unit with a nucleotide sequence that encodes an HIV gag polypeptide; (c) a third DNA plasmid that has a single transcriptional unit with a nucleotide sequence that encodes an HIV pol polypeptide; (d) a fourth DNA plasmid that has a single transcriptional unit with a nucleotide sequence that encodes an HIV nef-tat-vif fusion polypeptide; (e) a fifth DNA plasmid that has a nucleotide sequence that encodes an adjuvant polypeptide. In a specific embodiment, the promoter driving the expression of each of the HIV genes is the HCMV promoter and the polyA sequence for each of the HIV genes is the bovine growth hormone polyA.

In still a further embodiment, the DNA plasmids and immunogenic compositions may further contain, as an individual DNA plasmid component or as part of the antigen-containing DNA plasmid, a nucleotide sequence that encodes a desirable cytokine, lymphokine or other genetic adjuvant. A description of such suitable adjuvants for which nucleic acid sequences are available is provided below. In the embodiments exemplified in this invention, a desirable cytokine for administration with the DNA plasmid composition of this invention is Interleukin-12.

The DNA plasmid composition may be administered in a pharmaceutically acceptable diluent, excipient or carrier, such as those discussed below. Although the composition may be administered by any selected route of administration, in one embodiment a desirable method of administration is coadministration intramuscularly of a composition comprising the plasmid molecules with bupivacaine as the transfection facilitating agent, described below.

B. Physical Arrangement of Elements within the Plasmid

A practical consideration for designing a vertebrate immunogenic composition is the amount of DNA that can be effectively administered when immunizing subjects. When dose is considered, limiting the total size of the plasmid, while simultaneously maximizing the number of complete transcriptional units within the plasmid provides a strategy for creating plasmid DNA designs. The advantages of minimizing plasmid size and maximizing the number of genes expressed are that dose of immunogenic protein delivered per microgram of DNA injected is enhanced. In addition, is known that as vector size increases, so does the potential for vector instability. See Herrera et al., *Biochem. Biophys. Res. Commun.* 279:548-551 (2000). Therefore to achieve this goal, the size of the individual regulatory control elements, such as the promoters, should be considered and balanced with the strength of the promoter required for a given expression level. Similarly, the size of open reading frames contributes to the overall size of the plasmid. As used herein, DNA regions in between transcriptional units, which are occupied by DNA not having a regulatory or selected antigen encoding role, are referred to herein as "spacer regions". The size of the spacer regions is important in determining the level of transcriptional interference between transcriptional units, the level of steric hindrance and the total plasmid size. Therefore, the size of each element, whether it is protein coding, regulatory control or a spacer region must be carefully considered and limited to the smallest effective numbers of base pairs.

Embodiments of the present invention provide a triple transcriptional unit DNA plasmid that is less than or equal to about 18 kilo base pairs (kb) of DNA in total length. In an alternate embodiment, the present invention provides a triple transcriptional unit DNA plasmid that is less than or equal to about 17 kb of DNA in total length. Another embodiment of the present invention provides a triple transcriptional unit DNA plasmid that is less than or equal to about 16 kb of DNA in total length. A certain embodiment of the present invention provides a triple transcriptional unit DNA plasmid that is less than or equal to about 15 kb of DNA in total length. Still another embodiment of the present invention provides a triple transcriptional unit DNA plasmid that is less than or equal to about 14 kb of DNA in total length. A specific embodiment of the present invention provides a triple transcriptional unit DNA plasmid that is less than or equal to about 13 kb of DNA in total length. A particular embodiment of the present invention provides a triple transcriptional unit DNA plasmid that is less than or equal to about 12 kb of DNA in total length. Another embodiment of the present invention provides a triple transcriptional unit DNA plasmid that is less than or equal to about 11 kb of DNA in total length.

As used herein, "about" or "approximately" shall generally mean within 20 percent of a given value or range.

Figure 1:
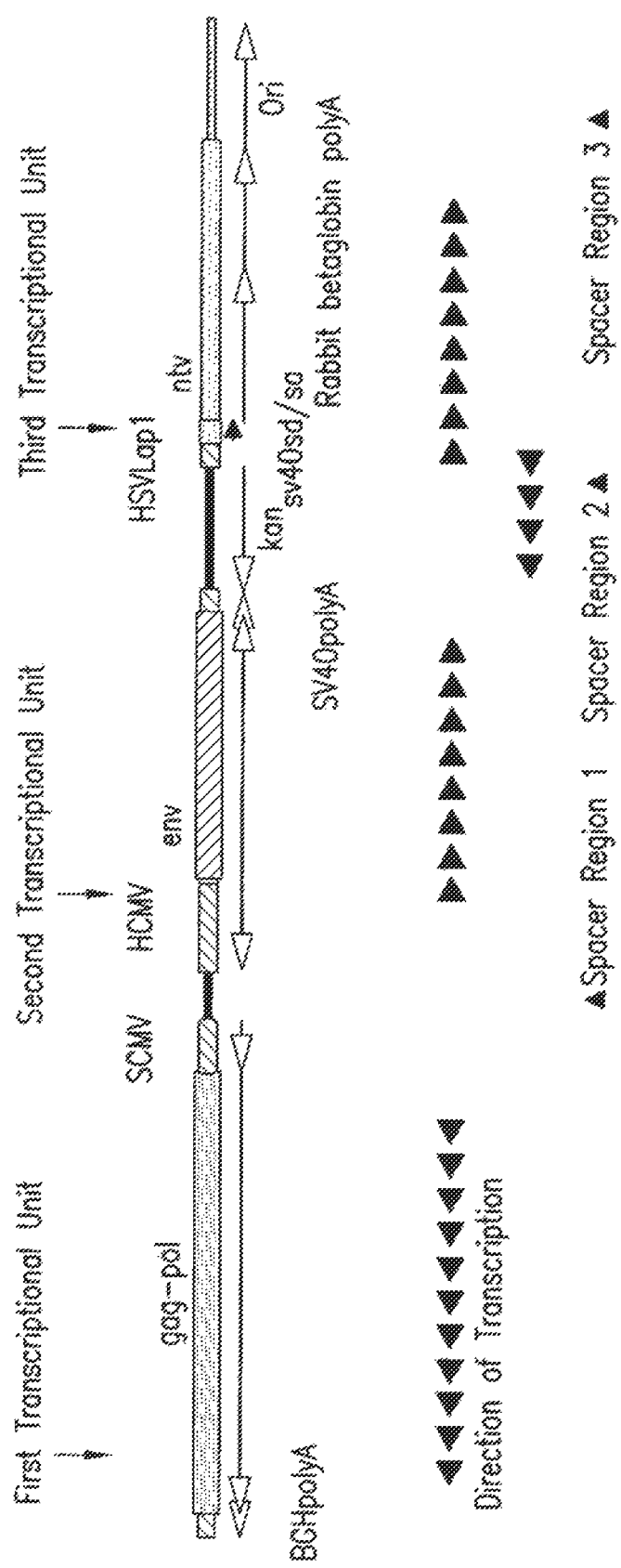
FIG. 1 shows a circular schematic diagram of an illustrative triple transcriptional unit DNA plasmid set up to express six HIV genes or gene constructs in eukaryotic cells from three separate open reading frames.

As defined in FIG. 1, orientation of the direction of transcription between the three transcriptional units is another consideration for DNA plasmid design. One of skill in the art of molecular biology would appreciate that in a circular DNA plasmid, there are only two directions of transcription. Therefore, in a plasmid with three transcriptional units, at least two of them will be going in the same direction. In a certain embodiment of the invention, the direction of transcription for the first transcriptional unit is in the opposite direction from the direction of expression of the second transcriptional unit. In another embodiment of the invention, the direction of transcription for the first transcriptional unit is in the opposite direction from the direction of expression of the second transcriptional unit and the direction of transcription of the third transcriptional unit is in the same direction as the second transcriptional unit. In still another embodiment of the invention, the direction of transcription for the first transcriptional unit is in the opposite direction from the direction of expression of the second transcriptional unit and the direction of transcription of the third transcriptional unit is in the same direction as the first transcriptional unit.

One of skill in the art will appreciate that the numbering of the transcriptional units as "first", "second" and "third" is for convenience only. The three transcriptional units can be arranged in any order around the plasmid.

In a plasmid with two transcriptional units, certain constraints exist regarding the direction of transcription for the two transcriptional units. If the directions of the transcription for the two transcriptional units are in the opposite direction, then the two transcriptional units may be separated by a spacer region of as small as 200 bp from one another, alternatively by a spacer region of small as 300 bp from one another, or alternatively by a spacer region of small as 400 bp from one another.

In a plasmid with two transcriptional units, if the directions of the transcription for the two transcriptional units are in the same directions, then the two transcriptional units should be separated by a spacer region of at least about 500 bp from one another. In another embodiment, the two transcriptional units should be separated by a spacer region of at least about 600 bp from one another. In still another embodiment, the two transcriptional units should be separated by a spacer region of at least about 700 bp from one another. In a certain embodiment, the two transcriptional units should be separated by a spacer region of at least about 800 bp from one another. In another embodiment, the two transcriptional units should be separated by a spacer region of at least about 900 bp from one another. In still another embodiment, the two transcriptional units should be separated by a spacer region of at least about 1000 bp from one another.

In another embodiment of the invention, the direction of transcription for the first transcriptional unit is in the same direction as the direction of expression of the second transcriptional unit. In still another embodiment of the invention, the direction of transcription for the first transcriptional unit is in the same direction as the direction of expression of the second transcriptional unit and the direction of transcription of the third transcriptional unit is in the same direction as the second transcriptional unit. In a particular embodiment of the invention, the direction of transcription for the first transcriptional unit is in the same direction as the direction of expression of the second transcriptional unit and the direction of transcription of the third transcriptional unit is in the opposite direction as the first transcriptional unit.

The size of the spacer regions is one variable that can be manipulated to relieve transcriptional interference between transcriptional units, decrease steric hindrance and to control overall plasmid size. In the embodiment shown in FIG. 1, there is a spacer region separating transcriptional units 1 and 2 that is located in between the SCMV and HCMV promoters. As used herein, the spacer region separating transcriptional units 1 and 2 is known as "spacer region 1." In the embodiment shown in FIG. 1, there is a spacer region separating transcriptional units 2 and 3 that is located in between the SV 40 poly A and HSV Lap 1 promoter. As used herein, the spacer region separating transcriptional units 2 and 3 is known as "spacer region 2." In the embodiment shown in FIG. 1, there is a third spacer region separating transcriptional units 3 and 1 that is located in between the BGH poly A and rabbit betaglobin poly A. As used herein, the spacer region separating transcriptional units 3 and 1 is known as "spacer region 3." See FIG. 1.

Another feature of the invention is that overall plasmid size may be minimized by using the spacer regions of the eukaryotic plasmid to fulfill plasmid and or adjuvant functions. For example, in the embodiment shown in FIG. 1, spacer region 3 also includes the bacterial origin of replication. In addition, in the embodiment shown in FIG. 1, spacer region 2 includes the kanamycin gene for growth in bacteria. In other embodiments, the spacer regions include CpG island sequences for stimulating the immune response. In another embodiment, the spacer regions include CTE and or RTE sequences for enhancing expression of antigens. In still another embodiment of the invention, the spacer region can include enhancer sequences. In another embodiment of the invention, the spacer region can include untranslated sequences known to be useful in enhancing expression.

In one embodiment of the invention, spacer region 1 is less than about 5 kb, alternatively less than about 4 kb in size. In another embodiment of the invention, spacer region 1 is less than less than about 3 kb, alternatively less than about 2 kb in size. In a certain embodiment of the invention, spacer region 1 is less than about 1 kb in size. In a particular embodiment of the invention, spacer region 1 is between about 800 base pairs (bp) and about 1000 bp in size. In an alternate embodiment of the invention, spacer region 1 is between about 600 bp and about 800 bp in size. In a certain embodiment of the invention, spacer region 1 is between about 400 bp and about 600 bp in size. In another embodiment of the invention, spacer region 1 is between about 300 bp and about 400 bp in size. In another embodiment of the invention, spacer region 1 is less than about 400 bp in size. In a specific embodiment of the invention, spacer region 1 is between about 200 bp and about 300 bp in size. In a particular embodiment of the invention, spacer region 1 is between about 100 bp and about 200 bp in size. In another embodiment of the invention, spacer region 1 is between about 10 bp and about 100 bp in size.

In one embodiment of the invention, spacer region 2 is less than less than about 5 kb, alternatively less than about 4 kb in size. In another embodiment of the invention, spacer region 2 is less than less than about 3 kb, alternatively less than about 2 kb in size. In a certain embodiment of the invention, spacer region 2 is less than about 1 kb in size. In another embodiment of the invention, spacer region 2 is less than about 1100 bp in size. In a particular embodiment of the invention, spacer region 2 is between about 800 base pairs (bp) and about 1000 bp in size. In an alternate embodiment of the invention, spacer region 2 is between about 600 bp and about 800 bp in size. In a certain embodiment of the invention, spacer region 2 is between about 400 bp and about 600 bp in size. In another embodiment of the invention, spacer region 2 is between about 300 bp and about 400 bp in size. In a specific embodiment of the invention, spacer region 2 is between about 200 bp and about 300 bp in size. In a particular embodiment of the invention, spacer region 2 is between about 100 bp and about 200 bp in size. In another embodiment of the invention, spacer region 2 is between about 10 bp and about 100 bp in size.

In one embodiment of the invention, spacer region 3 is less than less than about 5 kb, alternatively less than about 4 kb in size. In another embodiment of the invention, spacer region 3 is less than less than about 3 kb, alternatively less than about 2 kb in size. In a certain embodiment of the invention, spacer region 3 is less than about 1 kb in size. In another embodiment of the invention, spacer region 3 is less than about 1100 bp in size. In a particular embodiment of the invention, spacer region 3 is between about 800 bp and about 1000 bp in size. In an alternate embodiment of the invention, spacer region 3 is between about 600 bp and about 800 bp in size. In a certain embodiment of the invention, spacer region 3 is between about 400 bp and about 600 bp in size. In another embodiment of the invention, spacer region 3 is between about 300 bp and about 400 bp in size. In a specific embodiment of the invention, spacer region 3 is between about 200 bp and about 300 bp in size. In a particular embodiment of the invention, spacer region 3 is between about 100 bp and about 200 bp in size. In another embodiment of the invention, spacer region 3 is between about 10 bp and about 100 bp in size.

C. Antigens Expressed by Immunogenic Compositions of this Invention

As used herein, "polypeptide" refers to selected protein, glycoprotein, peptide or other modified protein antigens, which are encoded by the plasmids and immunogenic compositions of this invention. Embodiments of the invention provide plasmids and immunogenic compositions, which induce an immune response to "polypeptides" in a vertebrate host to a selected antigen. As used herein, the term "selected antigen" refers to these polypeptides. The selected antigens, which comprise the polypeptides, when expressed by the plasmid DNA, may include a protein, polyprotein, polypeptide, peptide, fragment or a fusion thereof derived from a pathogenic virus, bacterium, fungus, parasite, prion or combinations thereof. Alternatively, the selected antigens, may include a protein, polyprotein, polypeptide, peptide, fragment or fusion thereof derived from a cancer cell or tumor cell. In another embodiment, the selected antigens may include a protein, polyprotein, polypeptide, peptide, fragment or fusion thereof derived from an allergen so as to interfere with the production of IgE so as to moderate allergic responses to the allergen. In still another embodiment, the selected antigens may include a protein, polyprotein, polypeptide, peptide, fragment or fusion thereof derived from a molecule or portion thereof which represents those produced by a host (a self molecule) in an undesired manner, amount or location, such as those from amyloid precursor protein, so as to prevent or treat disease characterized by amyloid deposition in a vertebrate host. In one embodiment of this invention, the selected antigens may include a protein, polyprotein, polypeptide, peptide or fragment derived from HIV-1.

Embodiments of the present invention are also directed to immunogenic compositions comprising a plasmid encoding the selected antigens (1) from a pathogenic virus, bacterium, fungus or parasite to elicit the immune response in a vertebrate host, or (2) from a cancer antigen or tumor-associated antigen from a cancer cell or tumor cell to elicit a therapeutic or prophylactic anti-cancer effect in a mammalian subject, or (3) from an allergen so as to interfere with the production of IgE so as to moderate allergic responses to the allergen, or (4) from a molecule or portion thereof which represents those produced by a host (a self molecule) in an undesired manner, amount or location, so as to reduce such an undesired effect.

In another embodiment, a desirable immunogenic composition may utilize a triple transcriptional unit plasmid of this invention, which encodes selected antigens to induce an immune response aimed at preventing or to treating one of the following viral diseases: Human immunodeficiency virus, Simian immunodeficiency virus, Respiratory syncytial virus, Parainfluenza virus types 1-3, Influenza virus, Herpes simplex virus, Human cytomegalovirus, Hepatitis A virus, Hepatitis B virus, Hepatitis C virus, Human papillomavirus, Poliovirus, rotavirus, caliciviruses, Measles virus, Mumps virus, Rubella virus, adenovirus, rabies virus, canine distemper virus, rinderpest virus, Human metapneumovirus, avian pneumovirus (formerly turkey rhinotracheitis virus), Hendra virus, Nipah virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses, and Coronavirus, such as SARS virus.

In a particular embodiment, immunogenic compositions comprising the triple transcriptional unit plasmids of this invention include those encoding selected antigens from pathogens causing emerging diseases such as severe acute respiratory virus (SARS), human herpes virus 8 (HHV-8), Hantaanvirus, *Vibrio cholera* 0139, *Helicobacter pylori* and *Borrelia burgdorferi*.

In another embodiment, immunogenic compositions comprising the plasmids of this invention include those directed to the prevention and/or treatment of bacterial diseases caused by, without limitation, *Haemophilus influenzae* (both typable and nontypable), *Haemophilus somnus, Moraxella catarrhalis, Streptococcus pneumoniae, Streptococcus pyogenes, Streptococcus agalactiae, Streptococcus faecalis, Helicobacter pylori, Neisseria meningitidis, Neisseria gonorrhoeae, Chlamydia trachomatis, Chlamydia pneumoniae, Chlamydia psittaci, Bordetella pertussis, Alloiococcus otiditis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium-Mycobacterium intracellulare complex, Proteus mirabilis, Proteus vulgaris, Staphylococcus aureus, Staphylococcus epidermidis, Clostridium tetani, Leptospira interrogans, Borrelia burgdorferi, Pasteurella haemolytica, Pasteurella multocida, Actinobacillus pleuropneumoniae* and *Mycoplasma gallisepticum*.

Embodiments of the present invention are also directed to immunogenic compositions comprising a plasmid encoding selected antigens from, without limitation, *Aspergillis, Blastomyces, Candida, Coccidiodes, Cryptococcus* and *Histoplasma*. In certain embodiments, such immunogenic compositions comprising a plasmid encoding selected antigens from fungi are used for the prevention and/or treatment of fungal disease.

In another embodiment, of the present invention are also directed to immunogenic compositions comprising a plasmid encoding selected antigens from, without limitation, *Leishmania major, Ascaris, Trichuris, Giardia, Schistosoma, Cryptosporidium, Trichomonas, Toxoplasma gondii* and *Pneumocystis carinii*. In particular embodiments, such immunogenic compositions comprising a plasmid encoding selected antigens of parasites are used for the prevention and/or treatment of parasitic disease.

In a particular embodiment, this invention provides immunogenic compositions for eliciting a therapeutic or prophylactic anti-cancer effect in a vertebrate host, which comprise a plasmid encoding a selected antigen such as a cancer antigen or tumor-associated antigen, including, without limitation, prostate specific antigen, carcino-embryonic antigen, MUC-1, Her2, CA-125 and MAGE-3. In some embodiments, the same antigen or variants of the antigen may be placed in multiple transcriptional units to enhance transcription and ultimate dose of a particular target antigen.

Embodiments of the invention, also provide immunogenic compositions comprising plasmids encoding selected antigens that are allergens for use in moderating responses to allergens in a vertebrate host, include those containing an allergen or fragment thereof. Examples of such allergens are described in U.S. Pat. No. 5,830,877 and International Patent Publication No. WO99/51259, which are hereby incorporated by reference. Such allergens include, without limitation, pollen, insect venoms, animal dander, fungal spores and drugs. The immunogenic compositions of the invention may be used to interfere with the production of IgE antibodies, a known cause of allergic reactions.

Embodiments of the present invention are also directed to immunogenic compositions comprising a plasmid encoding selected antigens for moderating responses to self molecules in a vertebrate host. The selected antigens include those containing a self molecule or a fragment thereof. Examples of such self molecules include the β-chain of insulin that is involved in diabetes, the G17 molecule involved in gastroesophageal reflux disease, and antigens which down regulate autoimmune responses in diseases such as multiple sclerosis, lupus and rheumatoid arthritis. Also included is the β-amyloid peptide (also referred to as Aβ peptide), which is an internal, 39-43 amino acid fragment of amyloid precursor protein (APP), which is generated by processing of APP by the β and γ secretase enzymes. The Aβ1-42 peptide has the following sequence: Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO:1).

It is also desirable in the selection and use of the sequences encoding the selected antigens for design of the DNA plasmids of this invention to alter codon usage of the selected antigens encoding gene sequences, as well as the DNA plasmids into which they are inserted, in order to increase the expression of the antigens and/or to remove inhibitory sequences therein. The removal of inhibitory sequences can be accomplished by using the technology discussed in detail in U.S. Pat. Nos. 5,965,726; 5,972,596; 6,174,666; 6,291,664; and 6,414,132; and in International Patent Publication No. WO01/46408, incorporated by reference herein. Briefly described, this technology involves mutating identified inhibitor/instability sequences in the selected gene, preferably with multiple point mutations.

As one specific embodiment exemplified below, the DNA plasmid and immunogenic compositions of this invention desirably employ one or more sequences optimized for HIV-1 genes, such as the gag, pol, env nef, tat, and vif.

The triple transcriptional unit plasmid of this invention is also suitable for use to transfect, transform or infect a host cell to express three or more proteins of polypeptides in vitro.

D. Promoters Useful in the Transcriptional Units

The DNA plasmids of the invention comprise one, two or three transcriptional units. Each transcriptional unit comprises at least one promoter. Therefore, in certain embodiments of the invention, the nucleic acid encoding a selected antigen is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and transcription of the gene.

The term promoter is used herein to refer to a group of transcriptional control modules that are clustered around the initiation site for the RNA polymerase. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Suitable promoters for use in any of the transcriptional units include all promoters active in eukaryotic cells. Examples of suitable eukaryotic promoters include human cytomegalovirus (HCMV) immediate early promoter (optionally with the HCMV enhancer) (see, e.g., Boshart et al, Cell, 41:521-530 (1985)), the simian cytomegalovirus (SCMV) promoter, the murine cytomegalovirus (MCMV) promoter, the herpes simplex virus (HSV) LAP1 promoter, the simian virus 40 (SV40) promoter, the Human elongation factor 1 alpha promoter, the retroviral long terminal repeats (LTRs), the muscle cell specific desmin promoter, or any other promoter active in an antigen presenting cell.

In addition, suitable eukaryotic promoters may be characterized as being selected from among constitutive promoters, inducible promoters, tissue-specific promoters and others. Examples of constitutive promoters that are non-specific in activity and employed in the DNA plasmids encoding selected antigens include, without limitation, the retroviral Rous sarcoma virus (RSV) promoter, the retroviral LTR promoter (optionally with the RSV enhancer), the SV40 promoter, the dihydrofolate reductase promoter, the β-actin promoter, the phosphoglycerol kinase (PGK) promoter, and the EF1α promoter (Invitrogen). Inducible promoters that are regulated by exogenously supplied compounds, include, without limitation, the arabinose promoter, the zinc-inducible sheep metallothionine (MT) promoter, the dexamethasone (Dex)-inducible mouse mammary tumor virus (MMTV) promoter, the T7 polymerase promoter system (WO 98/10088); the ecodysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769, (1995) see also Harvey et al, Curr. Opin. Chem. Biol., 2:512-518, (1998)), the RU486-inducible system (Wang et al, Nat. Biotech., 15:239-243, (1997) and Wang et al, Gene Ther., 4:432-441, (1997)) and the rapamycin-inducible system (Magari et al, J. Clin. Invest., 100: 2865-2872, (1997)).

Other types of inducible promoters that may be useful in DNA plasmids of the invention are those regulated by a specific physiological state, e.g., temperature or acute phase or in replicating cells only. Useful tissue-specific promoters include the promoters from genes encoding skeletal β-actin, myosin light chain 2A, dystrophin, muscle creatine kinase, as well as synthetic muscle promoters with activities higher than naturally-occurring promoters (see Li et al., Nat. Biotech., 17:241-245, (1999)). Examples of promoters that are tissue-specific are known for the liver (albumin, Miyatake et al. J. Virol., 71:5124-32 (1997); hepatitis B virus core promoter, Sandig et al., Gene Ther., 3: 1002-9, (1996); alpha-fetoprotein (AFP), Arbuthnot et al., Hum. Gene Ther., 7:1503-14, (1996)), bone (osteocalcin, Stein et al., Mol. Biol. Rep., 24:185-96, (1997); bone sialoprotein, Chen et al., J. Bone Miner. Res., 11:654-64, (1996)), lymphocytes (CD2, Hansal et al., J. Immunol., 161:1063-8, (1988); immunoglobulin heavy chain; T cell receptor α chain), neuronal (neuron-specific enolase (NSE) promoter, Andersen et al. Cell. Mol. Neurobiol., 13:503-15, (1993); neurofilament light-chain gene, Piccioli et al., Proc. Natl. Acad. Sci. USA, 88:5611-5, (1991); the neuron-specific ngf gene, Piccioli et al., Neuron, 15:373-84, (1995)); among others. See, e.g., International Patent Publication No. WO00/55335 for additional lists of known promoters useful in this context.

E. Polyadenylation Signals Useful in the Transcription Units

The DNA plasmids of the invention comprise three transcriptional units and each transcriptional unit comprises at least one polyadenylation signal. A "polyadenylation signal", as defined herein refers to a stop sequence (or stop site) that terminates transcription of a particular transcriptional unit and ensures that the nucleic acid sequence ecoding a polypeptide is transcribed and translated properly. The stop site can be synthetic or of natural origin. Examples of stop sites include, but are not limited to, a polyadenylation signal and a synthetic bi-directional transcriptional stop site. Typically, the polyadenylation signal arrests transcription of DNA sequences.

Suitable polyadenylation signals for use in any of the transcriptional units include all polyadenylation signals active in eukaryotic cells. Examples of eukaryotic polyadenylation signals include rabbit beta-globin poly(A) signal, a signal that has been characterized in the literature as strong (Gil and Proudfoot, Cell 49: 399-406 (1987); Gil and Proudfoot, Nature 312: 473-474 (1984)). One of its key features is the structure of its downstream element, which contains both UG- and U-rich domains. Other poly A signals include synthetic polyA, HSV Thymidine kinase poly A, (see Cole, C. N. and T. P. Stacy, Mol. Cell. Biol. 5:2104-2113 (1985)); Human alpha globin poly A SV40 poly A (See Schek, N, Cooke, C., and J. C. Alwine, Mol. Cell. Biol. 12:5386-5393 (1992)); human beta globin poly A (See Gil, A., and N. J. Proudfoot, Cell 49:399-406 (1987)); polyomavirus poly A (See Batt, D. B and G. G. Carmichael Mol. Cell. Biol. 15:4783-4790 (1995); Bovine growth hormone poly A, (Gimmi, E. R., Reff, M. E., and I. C. Deckman, Nucleic Acid Res. (1989)). Many other polyadenylation signals are known in the art, and will also be useful in embodiments of the invention.

Both the early and late polyadenylation signals of SV40 are useful in the various embodiments of the invention. See Schek, et al., Mol. Cell Biol. 12:5386-5393 (1992). These sequences are encoded within the 237-base pair fragment between the BamnHI site at nucleotide 2533 and the BclI site at nucleotide 2770 of the SV40 genome (Carswell and Alwine, Mol. Cell. Biol. 9:4248; 1989). Carswell and Alwine concluded that, of the two SV40 polyadenylation signals, the late signal was more efficient, most likely because it comprises both downstream and upstream sequence elements that facilitate efficient cleavage and polyadenylation.

Additional polyadenylation sites can be identified or constructed using methods that are known in the art. A minimal polyadenylation site is composed of AAUAAA and a second recognition sequence, generally a G/U rich sequence, found about 30 nucleotides downstream. As used herein, the sequences are presented as DNA, rather than RNA, to facilitate preparation of suitable DNAs for incorporation into expression vectors. When presented as DNA, the polyadenylation site is composed of AATAAA, with, for example, a G/T rich region downstream. Both sequences must be present to form an efficient polyadenylation site. The purpose of these sites is to recruit specific RNA binding proteins to the RNA. The AAUAAA binds cleavage polyadenylation specificity factor (CPSF; Murthy K. G., and Manley J. L. (1995), Genes Dev 9:2672-2683), and second site, frequently a G/U sequence, binds to Cleavage stimulatory factor (CstF; Takagaki Y. and Manley J. L. (1997) Mol Cell Biol 17:3907-3914). CstF is composed of several proteins, but the protein responsible for RNA binding is CstF-64, a member of the ribonucleoprotein domain family of proteins (Takagaki et al. (1992) Proc Natl Acad Sci USA 89:1403-1407).

F. Carriers, Diluents, Facilitating Agents, Adjuvants and Formulations Useful for the Immunogenic Compositions of this Invention The DNA plasmids and immunogenic compositions useful in this invention, further comprise an pharmaceutically acceptable diluent, excipient or a pharmaceutically acceptable carrier. In one embodiment, said pharmaceutically acceptable diluent is sterile water, sterile isotonic saline or a biological buffer. The antigenic compositions may also be mixed with such diluents or carriers in a conventional manner. As used herein the language "pharmaceutically acceptable carrier" is intended to include any and all solvents, dispersion media, coatings, antibacterial and antifungal agents, isotonic and absorption delaying agents, and the like, compatible with administration to humans or other vertebrate hosts. The appropriate carrier is evident to those skilled in the art and will depend in large part upon the route of administration.

Still additional excipients that may be present in the immunogenic compositions of this invention are adjuvants, facilitating agents, preservatives, surface active agents, and chemical stabilizers, suspending or dispersing agents. Typically, stabilizers, adjuvants, and preservatives are optimized to determine the best formulation for efficacy in the human or veterinary subjects.

1. Adjuvants

An adjuvant is a substance that enhances the immune response when administered together with an immunogen or antigen. A number of cytokines or lymphokines have been shown to have immune modulating activity, and thus may be used as adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms), the interferons-α, β and γ, granulocyte-macrophage colony stimulating factor (see, e.g., U.S. Pat. No. 5,078,996 and ATCC Accession Number 39900), macrophage colony stimulating factor (MCSF), granulocyte colony stimulating factor (GCSF), and the tumor necrosis factors α and β (TNF). Still other adjuvants useful in this invention include a chemokine, including without limitation, MCP-1, MIP-1α, MIP-1β, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin superfamily such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.1, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, incorporated herein by reference.

In one embodiment, the desired adjuvant is IL-12 protein, which is expressed from a plasmid. See, e.g., U.S. Pat. Nos. 5,457,038; 5,648,467; 5,723,127 and 6,168,923, incorporated by reference herein. In one embodiment, the cytokine may be administered as a protein. In a certain embodiment, IL-12 is expressed from one or two of the three transcriptional units of the DNA plasmid of the invention. Alternatively, Il-12 is expressed independently from a separate plasmid. In another embodiment, a plasmid encoding and expressing IL-15 is administered instead of a plasmid encoding and expressing IL-12.

Suitable adjuvants used to enhance an immune response include, without limitation, MPL™ (3-O-deacylated monophosphoryl lipid A; Corixa, Hamilton, Mont.), which is described in U.S. Pat. No. 4,912,094, which is hereby incorporated by reference. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecanoylamino]ethyl 2-Deoxy-4-O-phosphono-3-O—[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form or as a stable emulsion.

Still other adjuvants include mineral oil and water emulsions, aluminum salts (alum), such as aluminum hydroxide, aluminum phosphate, etc., Amphigen, Avridine, L121/squalene, D-lactide-polylactide/glycoside, pluronic polyols, muramyl dipeptide, killed Bordetella, saponins, such as Stimulon™ QS-21 (Antigenics, Framingham, Mass.), described in U.S. Pat. No. 5,057,540, which is hereby incorporated by reference, and particles generated therefrom such as ISCOMS (immunostimulating complexes), Mycobacterium tuberculosis, bacterial lipopolysaccharides, synthetic polynucleotides such as oligonucleotides containing a CpG motif (U.S. Pat. No. 6,207,646, which is hereby incorporated by reference), a pertussis toxin (PT), or an E. coli heat-labile toxin (LT), particularly LT-K63, LT-R72, PT-K9/G129; see, e.g., International Patent Publication Nos. WO 93/13302 and WO 92/19265, incorporated herein by reference.

Also useful as adjuvants are cholera toxins and mutants thereof, including those described in published International Patent Application number WO 00/18434 (wherein the glutamic acid at amino acid position 29 is replaced by another amino acid (other than aspartic acid), preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid positions 35 and 36).

In some embodiments, plasmid DNA that encodes an adjuvant may be administered in an immunogenic composition. In such cases, an adjuvant whose DNA is inserted into a plasmid for inclusion in the immunogenic compositions of the invention includes, but are not limited to, interleukin-1 (IL-1), IL-5, IL-10, IL-12, IL-15, IL-18, TNF-α, TNF-β and BL-1 (as described in published International Patent Application WO 98/17799); B7.2 (as described in published International Patent Application WO 00/51432); IL-8, RANTES, G-CSF, IL-4, mutant IL-18, IL-7, TNF-R (as described in published International Patent Application WO 99/43839); and mutant CD80 (as described in published International Patent Application WO 00/66162). As used herein, the term "IL-12 protein" is meant to refer to one or both human IL-12 subunits including single chain IL-12 proteins in which the two subunits are encoded by a single coding sequence and expressed as a single protein having a linker sequences connecting the two subunits.

In a particular embodiment, the cytokine is administered as a nucleic acid composition comprising a DNA sequence encoding the cytokine under the control of regulatory sequences directing expression thereof in a mammalian cell. In still another embodiment, the cytokine-expressing plasmid is administered with the DNA plasmid encoding selected antigens in an immunogenic composition. In still another embodiment, the cytokine is administered between the administrations of a priming immunogenic composition and a boosting immunogenic composition. In yet another embodiment, the cytokine is administered with the boosting step. In still another embodiment, the cytokine is administered with both priming and boosting compositions.

In certain embodiments of the invention, CpG DNA may be included in the plasmid as an adjuvant. As used herein, CpG DNA refers to an oligonucleotide containing at least one unmethylated CpG dinucleotide nucleic acid molecule which contains an unmethylated cytosine-guanine dinucleotide sequence (i.e. "CpG DNA") or DNA containing a 5' cytosine followed by 3' guanosine and linked by a phosphate bond) and activates the immune system. See U.S. Pat. No. 6,406,705 to Davis et al., and U.S. Pat. No. 6,207,646 to Krieg et al., which are hereby incorporated by reference in their entirety. CpG DNA from bacterial DNA, but not vertebrate DNA, has direct immunostimulatory effects on peripheral blood mononuclear cells (PBMC) in vitro. This lymphocyte activation is due to unmethylated CpG dinucleotides, which are present at the expected frequency in bacterial DNA ($1/16$), but are underrepresented (CpG suppression, $1/50$ to $1/60$) and methylated in vertebrate DNA. It is has been suggested that the rapid immune activation in response to CpG DNA may have evolved as one component of the innate immune defense mechanisms that recognize structural patterns specific to microbial molecules. See U.S. Pat. No. 6,406,705 to Davis et al., and U.S. Pat. No. 6,207,646 to Krieg et al., which are hereby incorporated by reference in their entirety.

In certain embodiments, the subject is administered a combination of adjuvants, wherein the combination of adjuvants includes at least one oligonucleotide containing at least one unmethylated CpG DNA dinucleotide and at least one non-nucleic acid adjuvant such as IL-12.

2. Facilitating Agents or Co-Agents

Immunogenic compositions composed of polynucleotide molecules desirably contain optional excipients such as polynucleotide transfection facilitating agents or "co-agents", such as a local anesthetic, a peptide, a lipid including cationic lipids, a liposome or lipidic particle, a polycation such as polylysine, a branched, three-dimensional polycation such as a dendrimer, a carbohydrate, a cationic amphiphile, a detergent, a benzylammonium surfactant, or another compound that facilitates polynucleotide transfer to cells. Such a facilitating agent includes the local anesthetic bupivacaine or tetracaine (see U.S. Pat. Nos. 5,593,972; 5,817,637; 5,380,876; 5,981,505 and 6,383,512 and International Patent Publication No. WO98/17799, which are hereby incorporated by reference). Other non-exclusive examples of such facilitating agents or co-agents useful in this invention are described in U.S. Pat. Nos. 5,703,055; 5,739,118; 5,837,533; International Patent Publication No. WO96/10038, published Apr. 4, 1996; and International Patent Publication No WO94/16737, published Aug. 8, 1994, which are each incorporated herein by reference.

Most preferably, the transfection facilitating agent is present in an amount that forms one or more complexes with the nucleic acid molecules. When the transfection facilitating agent is mixed with nucleic acid molecules or plasmids of this invention, it forms a variety of small complexes or particles that pack the DNA and are homogeneous. Thus, in one embodiment of the immunogenic compositions of this invention, the complexes are formed by mixing the transfection facilitating agent and at least one plasmid of this invention.

In a particular embodiment, an immunogenic composition of the invention may be comprised of more than one type of plasmid. Alternatively, in another embodiment of the compositions of the invention, the transfection facilitating agent may be pre-mixed with each plasmid separately. The separate mixtures are then combined in a single composition to ensure the desired ratio of the plasmids is present in a single immunogenic composition, if all plasmids are to be administered in a single bolus administration. Alternatively, the transfection facilitating agent and each plasmid may be mixed separately and administered separately to obtain the desired ratio.

Where, hereafter, the term "complex" or "one or more complexes" or "complexes" is used to define this embodiment of the immunogenic composition, it is understood that the term encompasses one or more complexes. Each complex contains a plasmid. Preferably, the complexes are between about 50 to about 150 nm in diameter. When the facilitating agent used is a local anesthetic, preferably bupivacaine, an amount from about 0.1 weight percent to about 1.0 weight percent based on the total weight of the polynucleotide composition is preferred. See, also, International Patent Publication No. WO99/21591, which is hereby incorporated by reference, and which teaches the incorporation of benzylammonium surfactants as co-agents, preferably administered in an amount between about 0.001-0.03 weight %. According to the present invention, the amount of local anesthetic is present in a ratio to said nucleic acid molecules of about 0.01-2.5% w/v local anesthetic to about 1-10 μg/ml nucleic acid. Another such range is about 0.05-1.25% w/v local anesthetic to about 100 μg/ml to 1 mg/ml nucleic acid.

3. Other Additives to the Immunogenic Compositions

Other excipients can be included in the immunogenic compositions of this invention, including preservatives, stabilizing ingredients, surface active agents, and the like.

Suitable exemplary preservatives include chlorobutanol, potassium sorbate, sorbic acid, sulfur dioxide, propyl gallate, the parabens, ethyl vanillin, glycerin, phenol, and parachlorophenol.

Suitable stabilizing ingredients that may be used include, for example, casamino acids, sucrose, gelatin, phenol red, N-Z amine, monopotassium diphosphate, lactose, lactalbumin hydrolysate, and dried milk.

Suitable surface active substances include, without limitation, Freunds incomplete adjuvant, quinone analogs, hexadecylamine, octadecylamine, octadecyl amino acid esters, lysolecithin, dimethyl-dioctadecylammonium bromide), methoxyhexadecylglycerol, and pluronic polyols; polyamines, e.g., pyran, dextransulfate, poly IC, carbopol; peptides, e.g., muramyl peptide and dipeptide, dimethylglycine, tuftsin; oil emulsions; and mineral gels, e.g., aluminum phosphate, etc. and immune stimulating complexes (IS-COMS). The plasmids may also be incorporated into liposomes for use as an immunogenic composition. The immunogenic compositions may also contain other additives suitable for the selected mode of administration of the immunogenic composition. The immunogenic composition of the invention may also involve lyophilized polynucleotides, which can be used with other pharmaceutically acceptable excipients for developing powder, liquid or suspension dosage forms. See, e.g., Remington: The Science and Practice of Pharmacy, Vol. 2, 19$^{th}$ edition (1995), e.g., Chapter 95 Aerosols; and International Patent Publication No. WO99/45966, the teachings of which are hereby incorporated by reference.

These immunogenic compositions can contain additives suitable for administration via any conventional route of administration. In some embodiments, the immunogenic composition of the invention is prepared for administration to human subjects in the form of, for example, liquids, powders, aerosols, tablets, capsules, enteric-coated tablets or capsules, or suppositories. Thus, the immunogenic compositions may also include, but are not limited to, suspensions, solutions, emulsions in oily or aqueous vehicles, pastes, and implantable sustained-release or biodegradable formulations. In one embodiment of the invention, the immunogenic compositions are prepared as a formulation for parenteral administration, the active ingredient is provided in dry (i.e., powder or granular) form for reconstitution with a suitable vehicle (e.g., sterile pyrogen-free water) prior to parenteral administration of the reconstituted composition. Other useful parenterally-administrable formulations include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The immunogenic compositions of the present invention, are not limited by the selection of the conventional, physiologically acceptable carriers, diluents and excipients such as solvents, buffers, adjuvants, facilitating agents or other ingredients useful in pharmaceutical preparations of the types described above. The preparation of these pharmaceutically acceptable compositions, from the above-described components, having appropriate pH isotonicity, stability and other conventional characteristics is within the skill of the art.

F. Dosages and Routes of Administration, Electroporation for Immunogenic Compositions In general, selection of the appropriate "effective amount" or dosage for the components of the immunogenic composition(s) of the present invention will also be based upon the identity of the selected antigens in the immunogenic composition(s) employed, as well as the physical condition of the subject, most especially including the general health, age and weight of the immunized subject. The method and routes of administration and the presence of additional components in the immunogenic compositions may also affect the dosages and amounts of the DNA plasmid compositions. Such selection and upward or downward adjustment of the effective dose is within the skill of the art. The amount of plasmid required to induce an immune response, preferably a protective response, or produce an exogenous effect in the patient without significant adverse side effects varies depending upon these factors. Suitable doses are readily determined by persons skilled in the art.

The immunogenic compositions of this invention are administered to a human or to a non-human vertebrate by a variety of routes including, but not limited to, intranasal, oral, vaginal, rectal, parenteral, intradermal, transdermal (see, e.g., International patent publication No. WO 98/20734, which is hereby incorporated by reference), intramuscular, intraperitoneal, subcutaneous, intravenous and intraarterial. The appropriate route is selected depending on the nature of the immunogenic composition used, and an evaluation of the age, weight, sex and general health of the patient and the antigens present in the immunogenic composition, and similar factors by an attending physician.

The order of immunogenic composition administration and the time periods between individual administrations may be selected by the attending physician or one of skill in the art based upon the physical characteristics and precise responses of the host to the application of the method. Such optimization is expected to be well within the skill of the art.

In another embodiment, a method is provided for co-expressing in a single cell, in vivo, one, two or three open reading frames of discrete gene products, which comprises introducing between about 0.1 µg and about 100 mg of a polynucleotide into the tissue of the mammal.

The immunogenic compositions may be administered and the uptake of the plasmids enhanced by the use of electroporation at the time of administration. To perform electroporation, electrodes are placed about 1-4 mm apart, near the area where the polynucleotide is injected. The exact position or design of the electrodes can be varied so long as current is permitted to pass through the muscle fibers perpendicular to their direction in the area of the injected polynucleotide. See U.S. Pat. No. 5,273,525 to G. A. Hofmann; U.S. Pat. No. 5,869,326 to G. A. Hofmann; U.S. Pat. No. 5,993,434 to S. B. Dev, et al.; U.S. Pat. No. 6,014,584 to G. A. Hofmann, et al.; U.S. Pat. No. 6,068,650 to G. A. Hofmann, et al.; U.S. Pat. No. 6,096,020 to G. A. Hofmann; U.S. Pat. No. 6,233,482 to G. A. Hofmann, et al.; U.S. Pat. No. 6,241,701 to G. A. Hofmann; U.S. Pat. No. 6,418,341 to G. A. Hofmann, et al.; U.S. Pat. No. 6,451,002 to S. B. Dev, et al.; U.S. Pat. No. 6,516,223 to G. A. Hofmann; U.S. Pat. No. 6,763,264 to G. A. Hofmann; U.S. Pat. No. 6,110,161 to I. Mathiesen, et al.; all of which are incorporated by reference in their entirety.

Once the electrodes are in position, the muscle is electroporated or electrically stimulated. The stimulation is delivered as a pulse having a predetermined amplitude and duration. In order to optimize the transfection efficiencies, the parameters of pulse duration, voltage, capacitance, field strength, number, wave type may be varied and transfection efficiencies compared. Electrical pulses are pulsed electric fields applied via electroporation. The pulse can be unipolar, bipolar, exponential or square wave form. Voltages have ranged from approximately 0 to 1000 volts; the pulse durations have ranged from 5 microseconds to 5 milliseconds; the number of pulses have ranged from a single pulse to 30,000 pulses; and the pulse frequency within trains have ranged from 0.5 Hz to 1000 Hz. Useful ranges for field strength are in the range of from about 25 V/cm to about 800 V/cm. Electric pulses contemplated for use in the practice of the present invention include those pulses of sufficient voltage and duration to cause electroporation. See Hofmann, G. A. Cells in electric fields. In E. Neumann, A. E. Sowers, & C. A. Jordan (Eds.), Electroporation and electrofusion in cell biology (pp. 389-407). Plenum Publishing Corporation (1989).

G. Kit Components

In still another embodiment, the present invention provides a pharmaceutical kit for ready administration of an immunogenic, prophylactic, or therapeutic regimen for treatment of any of the above-noted diseases or conditions for which an immune response to a selected antigen is desired. This kit is designed for use in a method of inducing a high level of antigen-specific immune response in a mammalian or vertebrate subject. The kit contains at least one immunogenic composition comprising a DNA plasmid comprising three transcriptional units encoding a set of selected antigens or peptides. Multiple prepackaged dosages of the immunogenic compositions can be provided in the kit for multiple administrations.

Where the above-described immunogenic compositions comprising a DNA plasmid does not also express a cytokine or other adjuvant, such as IL-12, the kit also optionally contains a separate cytokine/adjuvant composition or multiple prepackaged dosages of the cytokine/adjuvant composition for multiple administrations. These cytokine compositions are generally nucleic acid compositions comprising a DNA sequence encoding the selected cytokine under the control of regulatory sequences directing expression thereof in a mammalian or vertebrate cell. Other adjuvants may optionally be provided in a prepackaged vial either as a solution, liquid or solid.

The kit also contains instructions for using the immunogenic compositions in a prime/boost method. The kits may also include instructions for performing certain assays, various carriers, excipients, diluents, adjuvants and the like above-described, as well as apparatus for administration of the compositions, such as syringes, spray devices, etc. Other components may include disposable gloves, decontamination instructions, applicator sticks or containers, among other compositions.

In order that this invention may be better understood, the following examples are set forth. The examples are for the purpose of illustration only and are not to be construed as limiting the scope of the invention. All documents, publications and patents cited in the following examples are incorporated by reference herein.

EXAMPLES

Example 1

Selection and Modification of HIV Genes

One of skill in the art would appreciate that sequence information from many viruses and bacteria is available in the art. More particularly, sequence information can be used to clone genes for use in expressing polypeptides in plasmids of the invention. Information on many sequences from HIV and other pathogens is available from the HIV sequence database at the Los Alamos National Laboratory and the National Center for Biotechnology Information at the United States National Library of Medicine, (8600 Rockville Pike, Bethesda, Md. 20894).

In one embodiment of the invention, the following HIV genes were selected for inclusion into a single exemplary DNA plasmid expressing most of the HIV genome: gag gene from the HXB2 isolate and the pol gene from the HXB2 isolate. The complete HXB2 sequence is listed in the GenBank computer database under the accession number K03455. The nef, tat and vif genes were derived from the NL4-3 isolate. The complete NL4-3 sequence is listed in the GenBank computer database under the accession number M19921. The HIV envelope gene was derived from a primary isolate 6101 obtained from Dr. David Montefiore. The complete HIV envelope sequence is listed in the GenBank computer database under the accession numbers AY612855 and bankit625244.

To allow for the inclusion of most of the HIV genome into a single expression plasmid, gene fusions were prepared using full length gag-pol genes and nearly full length nef-tat-vif genes. In addition, the protease cleavage site between the gag and pol genes was removed. All HIV genes used in the embodiments of this invention were RNA optimized (sequence modified) for high-level protein expression. See U.S. Pat. Nos. 5,965,726; 5,972,596; 6,174,666; 6,291,664; and 6,414,132.

Alternatively, the HIV genes may be optimized in accordance with the methods provided in U.S. Application No. 60/576,819, filed on Jun. 4, 2004. According to this method, the expression of genes is enhanced by replacing certain wild type codons with "surrogate" codons. The enhanced sequence of the polynucleotide is determined by selecting suitable surrogate codons. Surrogate codons are selected in order to alter the A and T (or A and U in the case of RNA) content of the naturally-occurring (wild-type) gene. The surrogate codons are those that encode the amino acids alanine, arginine, glutamic acid, glycine, isoleucine, leucine, proline, serine, threonine, and valine. Therefore, the modified nucleic acid sequence has surrogate codons for each of these amino acids throughout the sequence. For the remaining 11 amino acids, no alterations are made, thereby leaving the corresponding naturally-occurring codons in place.

Standard techniques were employed to modify the above HIV genes to improve their safety and to optimize their expression. See Sambrook J, Fritsch E F and Maniatis T. Molecular cloning: A laboratory manual, $2^{nd}$ ed., Cold Spring Harbor Laboratory Press, Cold Spring Harbor N.Y. (1989). For example, the following genetic modifications were used to enhance safety (i.e., by inactivating viral enzymes) and maximize the breadth of HIV genes included in a subsequent vector:

1) Fusion polyproteins of HIV-1 gag-pol were created in a single open reading frame by removing the gag terminator and pol initiator from the respective genes and mutations were introduced in the wild type frameshift region to eliminate the formation of two individual proteins. In this example of a fusion construct the frameshift "slippery" sequence TTTTTT (SEQ ID NO:2) in wild type gagpol has been changed to cTTcTg (SEQ ID NO:3). For information on constructing a gag-pol fusion gene, see Megede, J. Z. et al. J. Virology 77:6197-6207 (2003), the disclosure of which is hereby incorporated by reference in its entirety. The wild type gag-pol fusion protein contains a 56 amino acid open reading frame polypeptide with no function, which separates the gag and pol genes. In order to minimize the overall size of the present construct, the gag polyprotein, which has the final four residues of the (Lys-Gly-Arg-Pro) (SEQ ID NO:4), was modified so as to be followed by a reduced ten amino acid intergenic region (Asp-Arg-Gln-Gly-Thr-Val-Ser-Phe-Asn-Phe) (SEQ ID NO:5). The first four residues of the pol polyprotein remain (Pro-Gln-Ile-Thr) (SEQ ID NO:6). No deviations from the wild-type coding regions of gag and pol genes were made to facilitate expression within the triple transcriptional unit plasmid.

2) All proteolytic activity of HIV-1 protease was inactivated by deleting the nucleotides that code for three active site amino acids (Asp-Thr-Gly from 25-27). See Loeb et al. Nature, 340:397 (1989); Wu et al. J Virol, 70: 3378 (1996).

3) Reverse transcriptase (RT) was inactivated by deleting nucleotides that code for the following four amino acids: Tyr 183, Met 184, Asp 185, Asp 186. See Larder et al., Nature, 327: 716-717 (1987); Larder et al. PNAS, 86: 4803-4807 (1989).

4) RNAse activity was abolished by deleting the nucleotides that code for a single amino acid: glu 478. See Davies et al., Science, 252:88-95 (1991); Schatz et al. 1989, FEBS lett. 257:311-314 (1989).

5) Integrase function was abolished by deleting the nucleotides that code for the following three amino acids: Asp 626, Asp 678 and Glu 714. See Wiskerchen et al. J. Virol, 69: 376-386 (1995); Leavitt et al. J. Biol. Chem., 268: 2113-2119 (1993).

6) A single open reading frame was created for the HIV-1 nef, tat and vif genes by fusing the following coding regions in frame (nef amino acid residues 4-206; tat amino acid residues 2-80; vif amino acid residues 2-192) to encode a single polyprotein. This polyprotein is referred to as nef-tat-vif or ntv.

7) As a safety precaution the nef and tat proteins were inactivated by removal of the myristylation signal (residues 1-3, MGG) of nef and deletion of two cysteines (C30 & C34) from tat.

Example 2

Construction of Single, Double and Triple Transcriptional Unit Plasmids

The plasmids discussed in these examples are set forth in Tables 1 and 2.

A triple transcriptional unit expression cassette was constructed by using a variety of components in a circular double stranded DNA plasmid. See FIG. 1. The first component was a first transcriptional unit for expressing polypeptides in eukaryotic cells, composed of the simian cytomegalovirus (SCMV) promoter, a cloning site and bovine growth hormone (BGH) poly-A signal. The second component is a second transcriptional unit for expressing polypeptides in eukaryotic cells, which consists of human cytomegalovirus (HCMV) immediate early promoter, a cloning site and the SV40 polyadenylation (polyA) signal. Separating the first and second transcriptional units is spacer region 1. The third component is a third transcriptional unit for expressing polypeptides in eukaryotic cells and is composed of the Herpes simplex virus Lap1 promoter, the SV40 splice donor/acceptor, a cloning site, and a rabbit beta globin poly-A signal. See Goins W. F. et al., J. Virology 68:2239-2252 (1994); Soares, K. J. et al., Virology 70:5384-5394; Goins W. F. et al., J. Virology 73:519-532 (1999). Separating the second and third transcriptional units is spacer region 2. Also included with spacer region 2 is a chimeric bacterial kanamycin resistance ($km^r$) gene, adenylyl 4'-nucleotidyl transferase type 1a. See Shaw K J, et al., Microbiol. Reviews 57: 138-163 (1993) and Sadale, Y, et al., J. Bacteriol. 141: 1178-1182 (1980). This gene has been devised to confer resistance to a limited number of aminoglycosides while it enables selection of bacteria containing the plasmid. Separating the third and first transcriptional units is spacer region 3. Spacer region 3 includes a pUC bacterial origin of replication that is required for propagation of the plasmid in bacteria.

Example 3

Triple Transcriptional Unit Plasmid Containing Six HIV Genes

As a demonstration of the use of the three transcriptional unit plasmid DNA vectors, a plasmid vector capable of co-expressing three eukaryotic open reading frames was created. The three transcriptional unit plasmid DNA vector was created by inserting the following selected genes encoding HIV-1 antigens into the triple transcriptional unit expression cassette described in Example 2. All cloning techniques were performed following conventional procedures (Sambrook et al. 1989).

First, an HIV-1 gag-pol fusion gene was inserted into the PmeI-XhoI cloning site between the SCMV and BGH poly-A sites of the first transcriptional unit. The gag gene was derived from the HXB2 isolate, and, similarly, the pol gene was also derived from the HXB2 isolate. The complete HXB2 sequence is listed in the GenBank computer database under the accession number K03455. One of skill in the art would understand that other HIV-1 gag and pol genes from other clades or other viral or bacterial genes could be inserted in a similar fashion. Sequence information on HIV and other pathogens is available from the HIV sequence database at the Los Alamos National Laboratory and the National Center for Biotechnology Information at the United States National Library of Medicine, 8600 Rockville Pike, Bethesda, Md. 20894.

Next, a full-length envelope gene (gp160) derived from a primary isolate (6101) of HIV-1 was inserted into the MluI cloning site between the HCMV and SV40 poly-A sites of the second eukaryotic transcriptional unit. The 6101 envelope sequence can be obtained in the GenBank computer database under the accession numbers AY612855 and bankit625244.

Finally, a gene construct coding for an HIV nef-tat-vif (NTV) fusion protein, which included nef residues 4-206 fused to tat residues 2-80 and fused to vif residues 2-192 was inserted into the KpnI-EcoRV cloning site between the HSV-Lap1 promoter and rabbit beta-globin poly-A signals. The nef, tat, and vif genes were derived from the NL4-3 isolate of HIV-1. The complete HIV-1 NL4-3 sequence is listed in the GenBank computer database under the accession number M19921.

Therefore, as constructed, the gag-pol open reading frame was placed under the control of SCMV promoter and BGH poly-A sites in the first transcriptional unit; the envelope open reading frame was placed under the control of HCMV promoter and SV40 poly-A signals in the second eukaryotic transcriptional unit; and the nef-tat-vif fusion open reading frame was placed under the control of HSV Lap1/SV40 intron and rabbit beta-globin poly-A signals in the third eukaryotic transcriptional unit.

Example 4

Expression of HIV Genes from Single, Double, Triple Transcriptional Unit Plasmids Materials and Methods: Cells and Transfection The plasmid expressing six HIV genes described in Example 3 was evaluated in vitro for the ability to express the encoded proteins. The cells used for all in vitro expression studies were 293 cells and RD cells that were obtained from the American Type Culture Collection (ATCC). The procedure for expressing HIV proteins in these cells was as follows: Cells were plated 24 hrs prior to transfection at a density of $2 \times 10^5$ cells per 35 mm diameter well and transfected with purified plasmid DNA. For transfection 2 µg of plasmid was mixed with Fugene transfection reagent (Roche Diagnostics, Indianapolis, Ind.) and layered over cells in a total volume of 100 µl. Next, the cells were incubated with 2 ml of DMEM media (BRL) with 10% FBS for 48 hrs. Finally, cell lysates were harvested for further analysis.

Detection of Expressed Proteins

Specific detection of HIV proteins was accomplished using a western blot assay. For example, a western blot assay for each of gag, pol, envelope and vif proteins was done by separating the protein mixture using SDS polyacrylamide gel electroproresis. Next, the separated proteins were then transferred onto PVDF membranes (Invitrogen, Carlsbad, Calif.). Prestained molecular weight markers and recombinant HIV-1 p24 (gag), p66 (pol), gp160 (env) and vif proteins (Invitrogen) were used as size standards and positive controls, respectively. Detection of gag, pol, env and vif expression was accomplished by immunostaining. The PVDF membranes having the bound and separated proteins were incubated with antibodies specific to the respective proteins. Secondary antibodies conjugated to alkaline phosphatase (Invitrogen) were used and color detection was performed by using the chromogenic detection kit (Invitrogen)

Expression of HIV Genes from Single, Double and Triple Transcriptional Unit Plasmids Expression of HIV genes from the triple transcriptional unit plasmid was evaluated and compared to expression of the same genes from each of a single transcriptional unit plasmid and a double transcriptional unit plasmid. The single transcriptional unit plasmid had a single eukaryotic transcriptional unit that contained an HCMV promoter and BGH poly-A signal as expression regulatory elements. The single transcriptional unit plasmids are numbered from 101 through 105, plus 110 and 111 as shown in Table 1. For example, plasmid 101 contained the HIV env gene as the open reading frame in the single transcriptional unit. Similarly, plasmid 102 contained the HIV gag gene as the open reading frame in the single transcriptional unit. In addition, plasmid 103 contained the HIV pol gene as the open reading frame in the single transcriptional unit and plasmid 104 contained the HIV nef-tat-vif (ntv) gene fusion as the open reading frame in the single transcriptional unit. Plasmid 101 also contained the HIV nef-tat-vif (ntv) gene fusion as the open reading frame in the single transcriptional unit, except it was driven by the Lap1 promoter rather than HCMV as in plasmid 104. Finally, plasmid 110 contained the HIV gag-pol-nef-tat-vif gene fusion as the open reading frame in the single transcriptional unit and plasmid 111 contained the HIV gag-pol gene fusion as the open reading frame in the single transcriptional unit.

The double transcriptional unit plasmids had two complete eukaryotic transcriptional units. The double transcriptional unit plasmids were numbered from 201 to 204 and 212 as shown in Table 1. The expression regulatory elements for the double transcriptional unit plasmids were comprised of an HCMV promoter coupled with an SV40 polyA in the first transcriptional unit and a SCMV promoter coupled with a BGH poly-A signal in the second transcriptional unit. In this embodiment, Plasmid 201 contained the HIV pol gene in the first transcriptional unit and HIV gag gene in the second transcriptional unit. Plasmid 202 contained the HIV nef-tat-vif gene fusion gene in the first transcriptional unit and HIV env gene in the second transcriptional unit. Plasmid 203 contained a HIV gag-pol-nef-tat-vif gene fusion gene in the first transcriptional unit and HIV env gene in the second transcriptional unit. Plasmid 204 contained the HIV gag-pol gene fusion gene in the first transcriptional unit and HIV env gene in the second transcriptional unit.

In some embodiments an adjuvant is provided by having it expressed from a plasmid. In such cases, the plasmid must contain the appropriate number of transcriptional units. For the sake of clarity, and in order to distinguish from antigen plasmids, the primary, secondary and tertiary terminology will be used to refer to adjuvant plasmids having one or two or three transcriptional units. For example, IL-12 is an adjuvant that is made up of two polypeptides. An appropriate plasmid is plasmid 212, which contained the IL-12 p35 subunit expressed under control of the HCMV immediate early promoter and SV40 polyadenylation signal in the primary transcriptional unit, and the IL-12 p40 subunit is expressed under control of the simian CMV promoter (SCMV) and BGH polyadenylation signal in the secondary transcriptional unit.

The triple transcriptional unit plasmids had three complete eukaryotic transcriptional units and were numbered 301, 302 and 303. See Table 2. The difference between the three plasmids was in the number of HIV open reading frames that were inserted. The expression regulatory elements for the triple transcriptional unit plasmids were comprised of an SCMV promoter coupled with a BGH poly-A signal in the first transcriptional unit, an HCMV promoter coupled with an SV40 polyA in the second transcriptional unit and an HSVLap1 promoter coupled with a rabbit betaglobin poly-A signal in the third transcriptional unit. As shown in Table 2, plasmid number 301 is a triple transcriptional unit plasmid, but with only one transcriptional unit having an inserted open reading frame. Specifically, plasmid 301 contained the gag-pol fusion gene open reading frame in the first transcriptional unit. Plasmid number 302 is the triple transcriptional unit plasmid having two transcriptional units with inserted open reading frames, the gag-pol in the first transcriptional unit and an HIV nef-tat-vif fusion gene open reading frame in the third transcriptional unit (no genes were inserted in the second transcriptional unit). Finally, plasmid number 303 is the triple transcriptional unit plasmid having all three transcriptional units with inserted open reading frames, the gag-pol gene fusion open reading frame in the first transcriptional unit, env gene open reading frame in the second transcriptional unit and nef-tat-vif fusion gene open reading frame in the third transcriptional unit.

TABLE 1

Single and Double Transcriptional Unit Plasmids*

| Plasmid No. | HIV Construct | Type |
| --- | --- | --- |
| 001 | Empty vector control | Control/No TUs |
| 101 | HCMV-env-BGH polyA | Single |
| 102 | HCMV-gag-BGH polyA | Single |
| 103 | HCMV-pol-BGH polyA | Single |
| 104 | HCMV-ntv-BGH polyA | Single |
| 105 | Lap1-ntv-Rabbit beta globin polyA | single |
| 110 | HCMV-gag-pol-ntv-BGH polyA | Single/fusion |
| 111 | HCMV-gag-pol-BGH polyA | Single/fusion |
| 201 | HCMV-pol-SV40 polyA, SCMV-gag-BGH polyA | Double |
| 202 | HCMV-ntv-SV40 polyA, SCMV-env-BGH polyA | Double |
| 203 | HCMV-gag-pol-ntv-SV40 polyA, SCMV-env-BGH polyA | Double |

TABLE 1-continued

Single and Double Transcriptional Unit Plasmids*

| Plasmid No. | HIV Construct | Type |
|---|---|---|
| 204 | HCMV-gag-pol-SV40 polyA, SCMV-env-BGH polyA | Double |
| 212 | **HCMV-mIL-12 p35-SV 40 polyA, SCMV-MIL-12 p40-BGH polyA | Adjuvant |

*The following abbreviations are used: SCMV: Simian cytomegalavirus promoter, HCMV: Human cytomegalovirus promoter, HSVlap1: Herpes simplex virus latency-associated promoter 1, gag-pol: HIV gag-pol fusion, ntv: HIV nef-tat-vif fusion, env: HIV envelope, mIL-12: murine interleukin-12.

TABLE 2

Triple Transcriptional Unit Plasmids*

| Plasmid No. | HIV Construct | No. ORFs |
|---|---|---|
| 301 | SCMV-gag-pol-BGH polyA, HCMV-[none], Lap1-[none] | one |
| 302 | SCMV-gag-pol-BGH polyA, HCMV-[none], Lap1: ntv-Rabbit beta globin polyA | two |
| 303 | SCMV: gag-pol-BGH polyA, HCMV-env-SV40 polyA, Lap1: ntv-Rabbit beta globin polyA | three |

*The following abbreviations are used: SCMV: Simian cytomegalavirus promoter, HCMV: Human cytomegalovirus promoter, HSVlap1: Herpes simplex virus latency-associated promoter 1, gag-pol: HIV gag-pol fusion, ntv: HIV nef-tat-vif fusion, env: HIV envelope, HCMV-[none], Lap1-[none] indicates the transcriptional units did not contain an open reading frame (see plasmid 301);
**Il-12 can be either murine or rhesus macaque or human As discussed above, multiple single and double transcriptional unit plasmids were constructed for use in comparing with the expression of the triple transcriptional unit plasmids. See Tables 1 and 2. The expression patterns of these gag, pol, env, nef-tat-vif, gag-pol and gag-pol-nef-tat-vif containing constructs were evaluated by transiently transfecting 293 and/or RD cells with the single, double, and triple transcriptional unit plasmids and analyzing cell lysates by western blots using appropriate antibodies.

Figure 2:
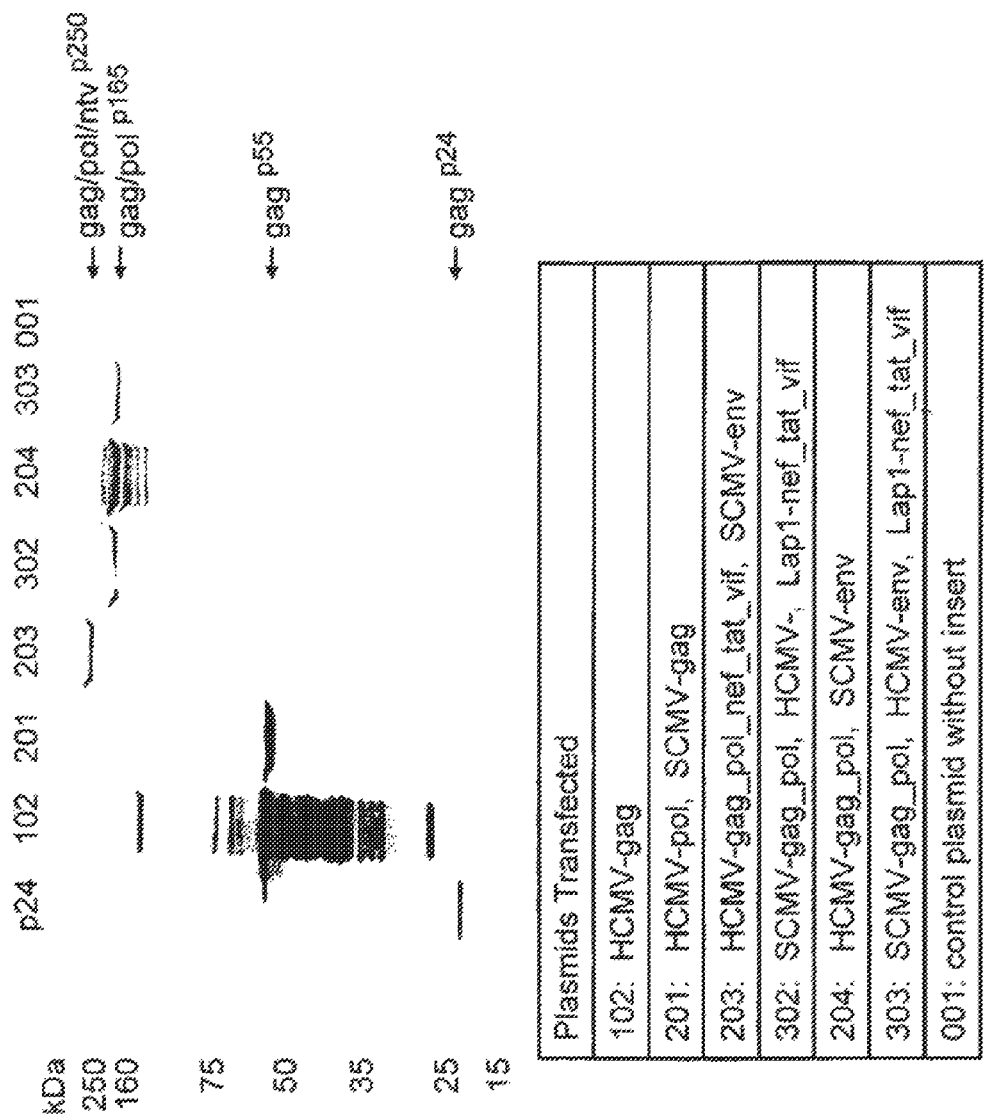
FIG. 2 shows HIV gag expression in 293 cells. 293 cells were transfected with 2 µg of indicated plasmid DNA expression vector. Forty-eight hours after transfection, cell associated HIV proteins were visualized by Western blot. The promoters and open reading frames for a particular plasmid are shown below:
Plasmids Transfected
102: HCMV-gag
201: HCMV-pol, SCMV-gag
203: HCMV-gag/pol/nef/tat/vif, SCMV-env
302: SCMV-gag/pol, HCMV-, Lap1-nef/tat/vif
204: HCMV-gag/pol, SCMV-env
303: SCMV-gag/pol, HCMV-env, Lap1-nef/tat/vif
001: control plasmid without insert

The in vitro expression of gag in cell lysates from various constructs was performed and the results were detected using Western blots. See FIG. 2 and Table 1. Gag and pol proteins were detected with mouse anti gag monoclonal and human polyclonal sera. Molecular weight markers and HIV p24 were included in the first two lanes as standards. The single transcriptional unit plasmid 102, which expressed gag, was run in the first sample lane. The plasmids having two transcriptional units and two transcriptional units with an inserted open reading frame were plasmids 201, 203 and 204 all produced significant amounts of gag, or gag-containing polyproteins such as gag-pol-nef-tat-vif, or gag-pol. In the gag-pol fusion constructs, frameshift sequences between gag and pol were mutated to allow gag and pol expression from the same reading frame. The two transcriptional unit plasmids 201, 203 and 204 produced less gag than the single transcriptional unit plasmid 102. The double or triple transcriptional unit plasmids, which encoded gag-pol fusions, expressed equivalent amounts of gag-pol polyprotein which migrated with an expected size of ~180 kd. Expression of gag from plasmid 203 that encodes a large gag-pol-ntv polyprotein was also detected in cell lysates of transfected cells and the protein migrated at an expected size of ~220 kD. Expression from this large fusion (plasmid 203), however, was lower than that of plasmids 302 and 303 encoding gag-pol. The three transcriptional unit plasmid 303 also produced significant amounts of gag in the form of gag-pol polyprotein but less gag than the single and about equivalent to the level produced from double transcriptional unit plasmids. The three transcriptional unit plasmid 302, which had two open reading frames inserted and one transcriptional unit without an open reading frame produced gag at approximately the same level as the two transcriptional unit plasmids. See FIG. 2.

Figure 3:
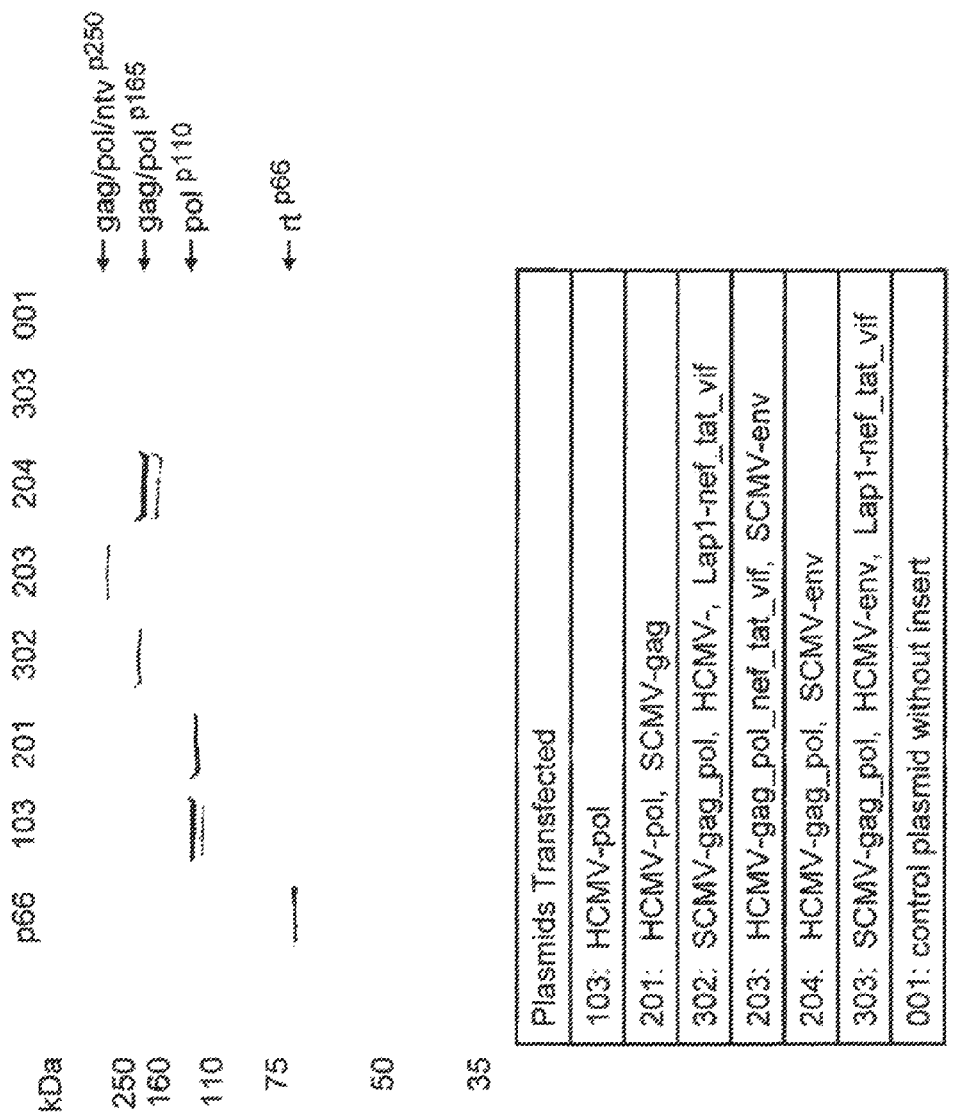
FIG. 3 shows HIV pol expression in 293 cells. 293 cells were transfected with 2 µg of indicated plasmid DNA expression vector. Forty-eight hours after transfections, cell associated HIV proteins were visualized by Western blot. The promoters and open reading frames for a particular plasmid are shown below:
Plasmids Transfected
103: HCMV-pol
201: HCMV-pol, SCMV-gag
302: SCMV-gag/pol, HCMV-, Lap1-nef/tat/vif
203: HCMV-gag/pol/nef/tat/vif, SCMV-env
204: HCMV-gag/pol, SCMV-env
303: SCMV-gag/pol, HCMV-env, Lap1-nef/tat/vif
001: control plasmid without insert

The in vitro expression profile of pol in cell lysates from various constructs was performed and the results as detected using Western blots followed a similar pattern as observed in the case of gag. See FIG. 3 and Table 1. In this case, pol proteins were detected with human polyclonal sera. Molecular weight markers and HIV reverse transcriptase were included in the first two lanes as standards. The single transcriptional unit plasmid 103, which expressed pol, was run in the first sample lane. Next, plasmids 201, 203 and 204 having two transcriptional units and two transcriptional units with an inserted open reading frame all produced significant amounts of pol, or pol-containing polyproteins such as gag-pol-nef-tat-vif, or gag-pol. In contrast to the situation with gag, the two transcriptional unit plasmids 201, 203 and 204 produced about the same level of pol as the single transcriptional unit plasmid 103. The pol, and gag-pol fusions expressed pol polyprotein which migrated with expected sizes of approximately 110 kd for pol, approximately 180 kd for gag-pol and approximately 250 kd for gag-pol-nef-tat-vif. The three transcriptional unit plasmid 303 also produced pol in the form of gag-pol polyprotein but less pol than the single and double transcriptional unit plasmids. Again, the three transcriptional unit plasmid 302, which had two open reading frames inserted and one transcriptional unit without an open reading frame expressed pol in the form of a gag-pol polyprotein at approximately the same level as the two transcriptional unit plasmids 201 and 203. See FIG. 3. In this example, plasmid 204 expressed greater levels of pol than the other two transcriptional unit plasmids 201 and 203. See FIG. 3.

Figure 4:
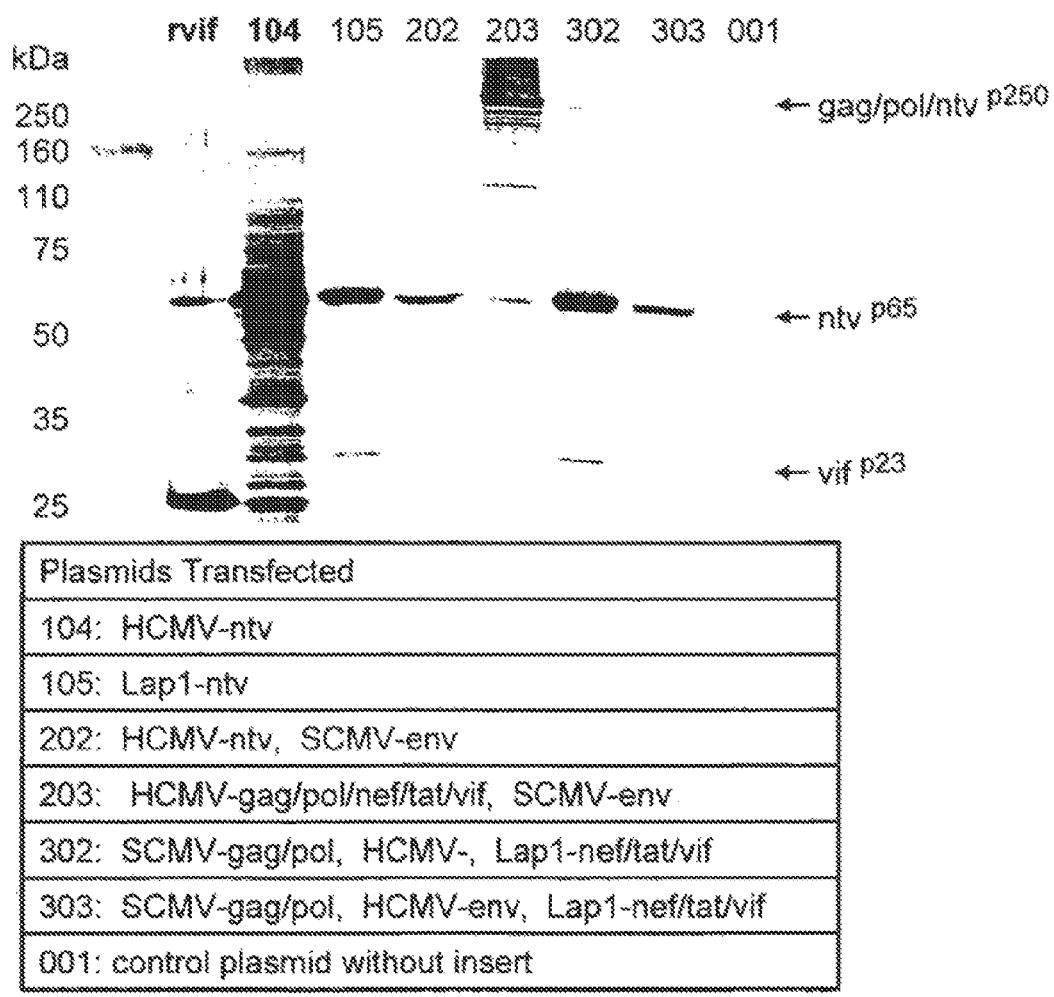
FIG. 4 shows HIV nef/tat/vif (ntv) expression in 293 cells. 293 cells were transfected with 2 µg of indicated plasmid DNA expression vector. Forty-eight hours after transfections, cell associated HIV proteins were visualized by Western blot. The promoters and open reading frames for a particular plasmid are shown below:
Plasmids Transfected
104: HCMV-ntv
105: Lap1-ntv
202: HCMV-ntv, SCMV-env
203: HCMV-gag/pol/nef/tat/vif, SCMV-env
302: SCMV-gag/pol, HCMV-, Lap1-nef/tat/vif
303: SCMV-gag/pol, HCMV-env, Lap1-nef/tat/vif
001: control plasmid without insert

A similar analysis was performed for the in vitro expression in cell lysates of the fusion of HIV regulatory proteins known as nef-tat-vif or NTV. See FIG. 4 and Table 1. NTV protein was detected with mouse anti-vif monoclonal antibody. Molecular weight markers and recombinant HIV vif p23 were included in the first two lanes, respectively, as standards. Two single transcriptional unit plasmids 104 and 105, which expressed NTV from either the HCMV or Lap 1 promoters respectively, were run in the first two sample lanes. See FIG. 4. The level of nef-tat-vif expression was about the same from both plasmids. Next, two plasmids having two compete transcriptional units with an inserted open reading frame (plasmids 202 and 203) both produced significant amounts of nef-tat-vif polyprotein. The level of nef-tat-vif protein expression appeared less for plasmid 203, but this was expected because the polyprotein being expressed was so large (gag-pol-nef-tat-vif ~220 kD). The three transcriptional unit plasmid 302, which had two open reading frames inserted, and one transcriptional unit without an open reading frame, produced nef-tat-vif at approximately the same level as the single transcriptional unit plasmid. See FIG. 4. The three transcriptional unit plasmid 303, which had three open reading frames inserted, also produced significant amounts of nef-tat-vif polyprotein. Specifically, the three transcriptional unit plasmid 303 produced less nef-tat-vif than the single transcriptional unit plasmids (104 and 105) and about equivalent to or better than the level of nef-tat-vif polyprotein produced from the double transcriptional unit plasmids (202 and 203). See FIG. 4.

Figure 5:
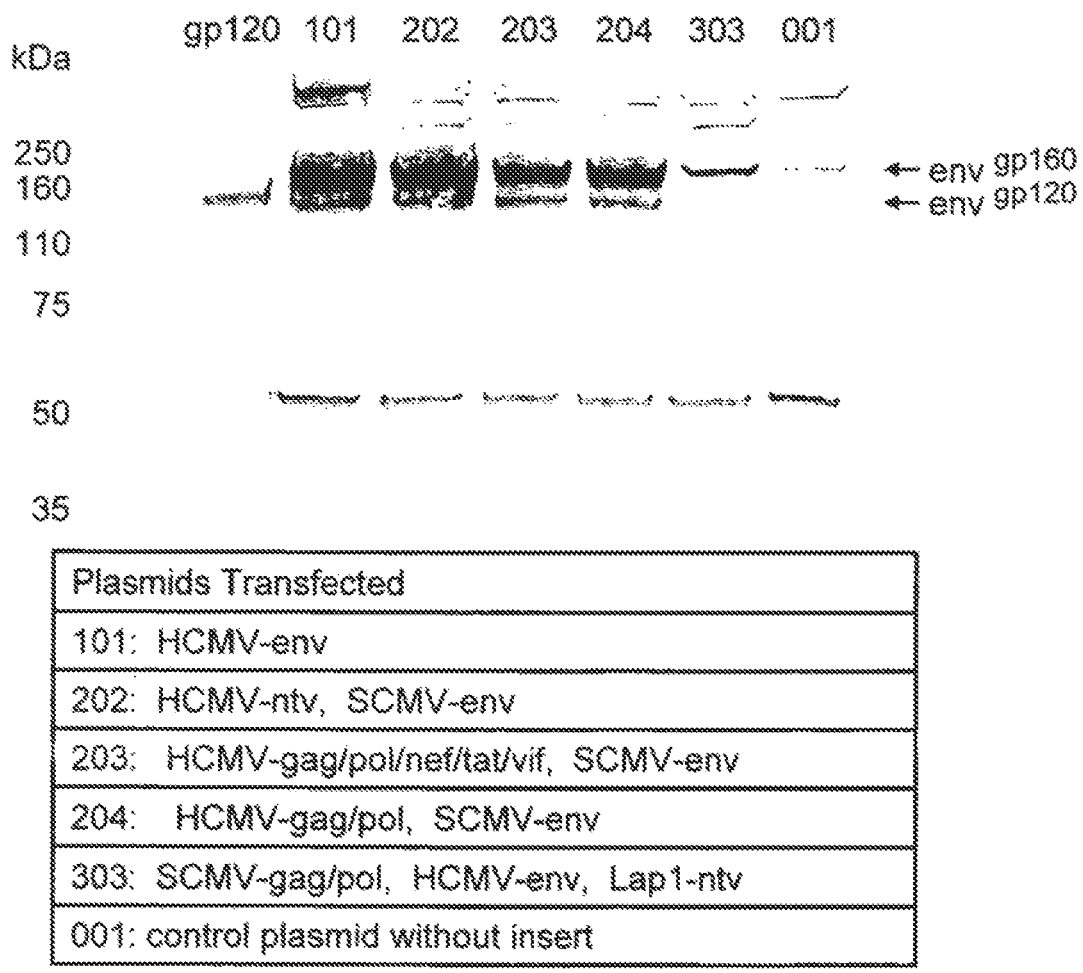
FIG. 5 shows HIV env expression in 293 cells. 293 cells were transfected with 2 µg of indicated plasmid DNA expression vector. Forty-eight hours after transfections, cell associated HIV proteins were visualized by Western blot. The promoters and open reading frames for a particular plasmid are shown below:
Plasmids Transfected
101: HCMV-env
202: HCMV-ntv, SCMV-env
203: HCMV-gag/pol/nef/tat/vif, SCMV-env
204: HCMV-gag/pol, SCMV-env
303: SCMV-gag/pol, HCMV-env, Lap1-nef/tat/vif
001: control plasmid without insert

The ability of various single, double and triple transcriptional unit plasmids to express the HIV-envelope gene in cell lysates was assessed. See FIG. 5 and Table 1. Envelope protein was detected with mouse anti-env monoclonal antibody.

Molecular weight markers and recombinant HIV gp120 were included in the first two lanes, respectively, as standards. The first sample lane contains the protein expressed from a single transcriptional unit plasmid 101, which expressed env from the HCMV promoter. See FIG. 5. Significant amounts of envelope glycoprotein were expressed. Next, three plasmids having two compete transcriptional units with two inserted open reading frames (plasmids 202, 203 and 204) produced significant amounts of envelope glycoprotein. In each case, envelope gene was controlled by the SCMV promoter. The three transcriptional unit plasmid 303 also produced significant amounts of env glycoprotein, but the level of expression was reduced by 2-3 fold, when compared to single and double transcriptional unit plasmids (101, 202, 203 and 204). See FIG. 5.

Conclusion

Based upon semi-quantitative in vitro expression analysis, the data indicate that all the inserted HIV genes, including gag-pol, env and ntv, were expressed at significant levels from the triple promoter plasmid carrying three independent transcriptional units.

Example 5

Figure 6:
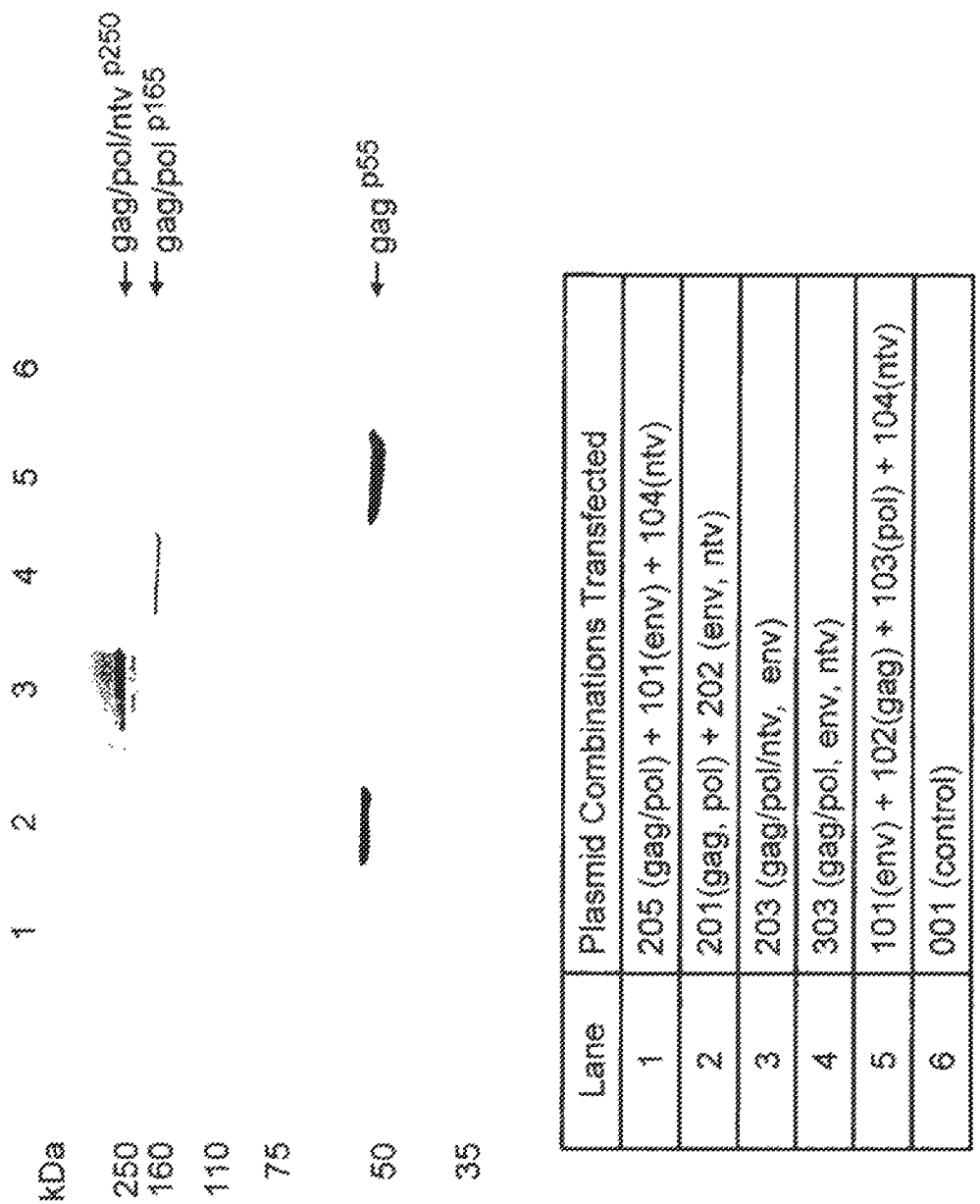
FIG. 6 shows HIV gag expression in 293 cells. 293 cells were transfected with 1 µg of indicated plasmid DNA combination. Forty-eight hours after transfections, cell associated HIV proteins were visualized by Western blot. The promoters and open reading frames for a particular plasmid are shown below.

Expression of Multiple Genes Via Multiple Plasmids or by a Single Plasmid at Constant DNA Concentration Per Plasmid Next, the expression from a single triple transcriptional unit plasmid encoding multiple genes was compared to multiple plasmids, each expressing a single gene from the same array of genes, where the DNA per plasmid was held constant at 1 µg. In each case, the total amount of DNA was also held constant at 4 µg by supplementing with plasmid DNA without an open reading frame insert. HIV gag expression was evaluated using cultured cells that were transiently transfected with 1 µg of each plasmid, and cell lysates were analyzed by western blot. As shown in FIG. 6, HIV gag expression was readily detected in lane 2 (two plasmids), lane 3 (one plasmid), lane 4 (one plasmid), and lane 5 (4 plasmids). HIV gag expression was low in lane 1 (three plasmids). The three transcriptional unit plasmid 303 again produced significant amounts of gag protein, although less than the combinations containing more plasmids.

HIV env expression from single or multiple plasmids was evaluated and the results are shown in FIG. 7. Again, 1 µg of each plasmid was transiently transfected into cultured cells and cell lysates were analyzed by western blot. The results demonstrate that HIV env expression was readily detected in lane 1 (3 plasmids), lane 2 (two plasmids), lane 3 (one plasmid), lane 4 (one plasmid), and lane 5 (4 plasmids). In each case the total amount of DNA was held constant at 4 µg by supplementing with plasmid DNA without an open reading frame insert to make the total amount of DNA equal to 4 µg. The three transcriptional unit plasmid 303 again produced significant amounts of env glycoprotein. See FIG. 7. In this case, the single three transcriptional unit plasmid 303 produced comparable amounts of env glycoprotein to that produced in lane 5 where 4 plasmids were used.

As shown in FIG. 8, HIV nef-tat-vif expression from single or multiple plasmids was evaluated using 1 µg of each plasmid transiently transfected into cultured cells and cell lysates were analyzed by western blot. See FIG. 8. The results demonstrate that HIV nef-tat-vif expression was detected in lane 1 (3 plasmids), lane 2 (2 plasmids), lane 3 (one plasmid), lane 4 (one three transcriptional unit plasmid), and lane 5 (4 plasmids). See FIG. 8. The total amount of DNA was held constant at 4 µg. The three transcriptional unit plasmid 303 produced significant amounts of nef-tat-vif protein, although less than the combination containing two plasmids.

Conclusion

As shown in FIGS. 6, 7 and 8, using the three transcriptional unit plasmid (303), all three open reading frames coding for gag-pol, env and ntv proteins were expressed simultaneously at similar levels, thus confirming the functionality of this plasmid.

Example 6

Expression of Multiple Genes Via Two Plasmids or by a Single Plasmid at Constant Total DNA Concentration The expression of HIV genes gag, pol, env and nef-tat-vif was compared between the triple transcriptional unit plasmid at 2 µg concentration and combinations of two plasmids each at 1 µg DNA. The total DNA concentration was held constant at 2 µg as indicated in FIGS. 9, 10, 11 and 12.

FIG. 9 shows that pol protein expression was similar from either of the two plasmid combinations or from the triple transcriptional unit plasmid. Lane 2 shows western blots of pol protein expressed from the combination of plasmids 201 and 202, two double transcriptional unit plasmids constructed to express the entire array of HIV genes, gag, pol, nef-tat-vif and env. Next, expression of pol protein from two combinations of a double transcriptional unit plasmid and a single transcriptional unit plasmid, which were expressing gag, pol, env and nef-tat-vif in various configurations, was evaluated using western blots of pol protein. See FIG. 9, lane 3 (plasmids 204 and 104) and lane 5 (plasmids 302 and 101). In each case there is detectable pol expression. Lane 4 contains western blots of pol protein expressed from plasmid 203, which is a double transcriptional unit plasmid expressing the entire array of HIV genes, gag-pol-nef-tat-vif and env. See FIG. 9. Lane 6 contains western blots of pol protein expressed from plasmid 303, which is an example of a triple transcriptional unit plasmid expressing the entire array of HIV genes, gag-pol env and nef-tat-vif, as described in Examples 2 and 3. See FIG. 9.

FIGS. 10 and 11 compare gag and envelope protein expression from the two plasmid combinations with protein expression from the triple transcriptional unit plasmid. Lane 2 shows western blots of gag and env proteins expressed from the combination of plasmids 201 and 202, which were two double transcriptional unit plasmids constructed to express the entire array of HIV genes, gag, pol, nef-tat-vif and env. Next, expression of gag and env proteins from combinations of a double transcriptional unit plasmid and a single transcriptional unit plasmid was evaluated using western blots. See FIGS. 10 and 11: lane 3 (plasmids 204 and 104) and lane 5 (plasmids 302 and 101). Plasmid 302 is a three transcriptional unit plasmid functioning as a two transcriptional unit plasmid because it has only two inserted open reading frames. See Table 2. There was detectable gag and env expression in each case. See FIG. 10. Lane 4 exemplifies western blots of gag and env proteins expressed from plasmid 203, which was a double transcriptional unit plasmid expressing the entire array of HIV genes, gag-pol-nef-tat-vif and env. See FIGS. 10 and 11. Lane 6 contains western blots of gag and env proteins expressed from the triple transcriptional unit plasmid 303 described in Examples 2 and 3. See FIGS. 10 and 11. Expression of gag and env proteins from the triple transcriptional unit plasmid 303 was comparable to that of the combinations of plasmids.

FIG. 12 compares nef-tat-vif polyprotein expression from various plasmid combinations with protein expression from the triple transcriptional unit plasmid using western blot detection. Lane 2 shows western blots of nef-tat-vif polyprotein expressed from the combination of plasmids 201 and 202, two double transcriptional unit plasmids designed to express HIV genes, gag, pol, nef-tat-vif and env. Lanes 3 and 5 show expression, as detected using western blots, of nef-tat-vif polyprotein from two different combinations of double transcriptional unit plasmids and a single transcriptional unit plasmid. See FIG. 12: lane 3 (plasmids 204 and 104) and lane 5 (plasmids 302 and 101). As discussed above, plasmid 302 is a three transcriptional unit plasmid functioning as a two transcriptional unit plasmid because it has only two inserted open reading frames. See Table 2. In this case, the nef-tat-vif protein expression from plasmid 302 seen in lane 5 was of a lower level than from plasmid combinations of 201 and 202 (lane 2) or 204 and 104 (lane 3). See FIG. 12. Lane 4 depicts nef-tat-vif polyprotein expressed from plasmid 203, which was a double transcriptional unit plasmid expressing the entire array of HIV proteins, gag-pol-nef-tat-vif and env. See FIG. 12. Lane 6 depicts nef-tat-vif polyprotein expressed from the triple transcriptional unit plasmid 303. See FIG. 12. Expression from 303 of nef-tat-vif was significantly higher than from plasmid 302. Noticeably, the expression from a two transcriptional unit plasmid (203) expressing a large gag-pol-nef-tat-vif polyprotein from one promoter and env protein from the other was substantially lower than that of plasmid 303 encoding the same genes from three independent transcriptional units.

In summary, using the triple transcriptional unit plasmid, three open reading frames could be expressed simultaneously at approximately equivalent levels and overall levels were comparable to both single and dual promoter constructs encoding those genes. The in vitro gene expression data suggests a lack of significant promoter interference when multiple HIV genes are expressed from a triple transcriptional unit plasmid. Therefore, the individual transcriptional units are placed appropriately in the vector.

Example 7

Expression of Multiple Genes Via Multiple Plasmids or by a Single Plasmid without Holding the Total DNA Concentration Constant The expression from a single triple transcriptional unit plasmid encoding multiple genes was compared to multiple plasmids, expressing the same array of genes, where the DNA per plasmid was held constant at 1 µg. In contrast to Example 5, the total amount of DNA was not supplemented with plasmid DNA without an open reading frame insert to make up for the total amount of DNA. The data are not shown, but are summarized below.

In this example, HIV gag, pol, env and ntv expression was evaluated using cultured 293 cells that were transiently transfected with 1 µg of each plasmid and cell lysates were analyzed by western blot. HIV gag expression was detected from transfections with combinations with three plasmids (101, 104, 301), two plasmids (201 and 202), one plasmid (203), one plasmid (303), and four plasmids (101, 102, 103, 104). The three transcriptional unit plasmid 303 produced significant amounts of gag protein as compared to combinations requiring more plasmids. Specifically, the three transcriptional unit plasmid 303 produced more gag polyprotein than the two transcriptional unit plasmid 203 having all six HIV genes and slightly less than the combination of two transcriptional unit plasmids 201 and 202 having all six HIV genes. The expression of gag in from the combination of three plasmids (101, 104, 301) was weak where gag was expressed as a gag-pol fusion driven by the SCMV promoter.

HIV env expression from single or multiple plasmids was also evaluated. The results demonstrated that HIV env expression was easily detected from combinations with three plasmids (301, 101 and 104), two plasmids (201 and 202), one plasmid (203), one plasmid (303), and four plasmids (101, 102, 103 and 104). The total amount of DNA depended on the number of plasmids being used, with 1 µg of DNA transfected per plasmid. In this case the three transcriptional unit plasmid 303 produced more env glycoprotein than any other plasmid or plasmid combination.

HIV nef-tat-vif expression from single or multiple plasmids was evaluated using 1 µg of each plasmid transiently transfected into cultured cells and cell lysates were analyzed by western blot. HIV nef-tat-vif expression was detected from combinations with three plasmids (301, 101 and 104), two plasmids (201 and 202), one plasmid (203), one plasmid (303), and four plasmids (101, 102, 103 and 104). The three transcriptional unit plasmid 303 produced significant amounts of nef-tat-vif protein.

Conclusion

A triple transcriptional unit plasmid encoding multiple HIV genes that express high levels of specific proteins in a rev-independent manner was designed and constructed, which confirmed that a single plasmid construct expressed three transcripts independently and efficiently. In this example, expression of HIV genes from the triple transcriptional unit plasmid was compared to the expression of the same genes from either single or double transcriptional unit constructs. The data indicate that gene expression from a triple transcriptional unit plasmid was lower when compared to those being expressed by single or dual expression cassettes. However, in the above example it was found that HCMV promoter-driven gene expression was higher than SCMV promoter, followed by HSV-lap1promoter. This difference in strength of the promoters in the triple transcriptional unit construct should be considered when positioning genes for expressing antigens of higher versus lower immunogenicity in the plasmid.

Example 8

Murine Immunization Studies with Plasmid Vectors Containing One, Two or Three Complete Transcriptional Units Murine studies were performed to establish and compare immunogenic functionality of the three transcriptional unit plasmid vector expressing proteins from six HIV-1 genes including gag, pol, env, nef, tat and vif. Specifically, the relative ability of various single, double and triple plasmid DNA-based immunogenic compositions to elicit multi-antigen-specific cell-mediated immune responses in Balb/c mice was compared.

Balb/c mice were immunized intramuscularly with 100 total µg doses of DNA as outlined in Table 3. In all cases, immunogenic compositions were formulated with 0.25% bupivacaine and injected into the quadricep muscles in a 100 µl volume. Ten days after the second immunization, animals were sacrificed and the serum and spleens were isolated for immune assays. Sera of immunized mice were analyzed for anti-gag, and anti-env specific antibody titers. Spleens were used to measure antigen-specific IFN-gamma secreting cells using ELISPOT assays as described below.

Animals

For these studies, 4-6 week old female Balb/c mice were used. Mice were maintained in accordance with the Guide for the Care and Use of Laboratory Animals (National Research Council, National Academic Press, Washington, D.C., 1996). In addition, procedures for the use and care of the mice were approved by Wyeth Research's Institutional Animal Care and Use Committee.

Immunogenic Compositions and Immunization

Various plasmid DNA expression vectors encoding HIVenv gp160, gag p55, pol, or a nef-tat-vif fusion protein were used as the experimental immunogenic compositions, and the empty expression vector backbone was used as a control immunogenic composition vector. See Table 3 below for study design. HIV gene expression by the various expression vectors was confirmed by Western blot after transient transfection of human rhabdosarcoma (RD) cells. See Examples 4-7.

The adjuvant used for these studies was also delivered via a DNA plasmid. In this example, all animals were co-injected with 25 μg of plasmid no. 212 expressing Il-12. This adjuvant plasmid is a two-trancriptional unit expression plasmid (plasmid no. 212 in Table 1) encoding murine IL-12 p35 and p40 genes. See Table 1. The IL-12 p35 subunit was expressed under control of the HCMV immediate early promoter and SV40 polyadenylation signal, while the IL-12 p40 subunit was expressed under control of the simian CMV promoter (SCMV) and BGH polyadenylation signal. Production of murine IL-12 was confirmed after transient transfection of RD cells by screening cell supernatants using an anti-mouse IL-12 p70 capture ELISA (Endogen, Woburn, Mass.) (data not shown).

TABLE 3

Mouse Study Design - Two Immunizations

| Group No. | Plasmid No. | Plasmid description | Total DNA.(ug) | No. mice | Immunization Schedule (week) |
|---|---|---|---|---|---|
| 1 | 303 | HCMV-env; SCMV-gag/pol; lap-ntv | 100 | 9 | 0 - 3 |
| 1a | 203 | HCMV- gag/pol; SCMV-env; | 100 | 9 | 0 - 3 |
| 2b | 101 + 110 | HCMV-env HCMV-gag-pol-ntv | 50 50 | 9 | 0 - 3 |
| 2c | 104 + 204 | HCMV-ntv HCMV-gag-pol, SCMV-env | 50 50 | 9 | 0 - 3 |
| 2d | 111 + 202 | HCMV-gag-pol HCMV-ntv, SCMV-env | 50 50 | 9 | 0 - 3 |
| 2e | 201 + 202 | HCMV-pol, SCMV-gag HCMV-ntv, SCMV-env | 50 50 | 9 | 0 - 3 |
| 3a | 111 101 104 | HCMV-gag/pol HCMV-env HCMV-ntv | 33 33 33 | 9 | 0 - 3 |
| 3b | 101 104 201 | HCMV-env HCMV-ntv HCMV-pol, SCMV-gag | 33 33 33 | 9 | 0 - 3 |
| 3c | 102 103 202 | HCMV-gag HCMV-pol HCMV-ntv, SCMV-env | 33 33 33 | 9 | 0 - 3 |
| 4 | 001 | Vector control | 100 | 6 | 0 - 3 |

Expression plasmids for immunization were produced by Puresyn, Inc. (Malvern, Pa.). Plasmids were propagated in *E. coli*, isolated from cells by alkaline lysis, purified by column chromatography and were formulated individually at a concentration of 2.5 mg/mL in isotonic citrate buffer (29.3 mM sodium citrate, 0.67 mM citric acid, 150 mM NaCl, 0.34 mM EDTA, pH=6.4-6.7) containing 0.25% bupivacaine as a facilitating agent to allow for the formation of DNA:bupivacaine complexes. For all groups, the adjuvant plasmid was mixed with the antigen expressing plasmids as part of the immunogenic composition. Final plasmid preparations were shown to consist of >90% supercoiled plasmid DNA and residual endotoxin was shown to be <30 EU/mg DNA (data not shown). Immediately prior to immunization, the immunogenic compositions were prepared by mixing the appropriate plasmid expression vector formulations. The resulting immunogenic compositions were administered by intramuscular injection into both quadriceps muscles (0.1 cc total injection volume, with 0.05 cc per site) using an 18 gauge needle and 0.3 mL syringe.

Murine IFN-γ ELISPOT Assay

ELISPOT (or ElisaSpot, short for Enzyme-linked ImmunoSpot Assay) originally was developed as a method to detect antibody-secreting B-cells. The method has now been adapted to determine T-cell reactions to a specific antigen, usually represented as number of activated cells per million. In the present example, Interferon gamma (IFN-gamma) production was used as a read-out for activation of single cells.

In this analysis, ELISPOT served to determine cytotoxic T-cell activity elicited by immunogenic compositions expressing specific HIV antigens. For the determination of IFN-γ ELISPOT responses, a Mouse IFN-γ ELISPOT kit (material number 551083, BD Biosciences, San Diego Calif.) was used. ELISPOT Assays were performed in ninety-six-well micotiter plates with a membrane bottom to each well. Specifically, ninety-six-well flat-bottom ELISPOT plates (ImmunoSpot, Cellular Technology Limited, Cleveland Ohio) were coated overnight with a purified anti-mouse γ-interferon (mIFN-γ) monoclonal antibody (Material No. 51-2525KC, BD-Biosciences, San Diego Calif.) at a concentration of 10 mcg/mL, after which the plates were washed three times with sterile 1× phosphate buffered saline (1×PBS) and then blocked for 2 hours with R10 complete culture medium (RPMI-1640 containing 10% heat inactivated (HI) fetal bovine serum (FBS) and 2 mM L-glutamine, 100 units/mL penicillin, 100 mcg/mL streptomycin sulfate, 1 mM sodium pyruvate, 1 mM HEPES, 100 mcM non-essential amino acids). Mouse spleens were first processed by grinding the spleens between the frosted end of two sterile microscope slides. The resulting homogenate was resuspended in 10 mls of in complete R05 culture medium (RPMI 1640 medium supplemented with 5% FBS, 2 mM L-glutamine, 100 units/mL penicillin, 100 mcg/mL streptomycin sulfate, 1 mM sodium pyruvate, 1 mM HEPES, 100 mcM non-essential amino acids) and splenocytes were subsequently isolated by Ficoll-Hypaque density gradient centrifugation and resuspended in complete R10 culture medium containing either 2 mcg/mL Con-A (Sigma), peptide pools (15 mers overlapping by 11 amino acids; 2.5 mcM each final peptide concentration) spanning HIV gag p55, HIV-1 6101 env gp160, pol, nef, tat, vif, or medium alone. Input cell numbers were $4\times10^5$ splenocytes per well ($4\times10^6$ splenocytes/mL) and assayed in duplicate wells. Splenocytes were incubated for 22-24 hours at 37° C. and then removed from the ELISPOT plate by first washing 3 times with deionized water and incubating on ice for 10-20 minutes. Then plates were washed 6 times with 1×PBS containing 0.1% Tween-20. Thereafter, plates were treated with an anti-mouse IFN-γ biotinylated detection antibody (5.0 mcg/ml, Material No. 51-1818KZ, BD-Biosciences, San Diego Calif.) diluted with R10 and incubated overnight at 4° C. ELISPOT plates were then washed 10 times with 1×PBS containing 0.1% Tween-20 and treated with 100 mcL per well of streptavidin-horseradish peroxidase conjugate (Catalog No. 51-9000209, BD-Biosciences, San Diego Calif.)) diluted 1:100 with R10 and incubated an additional 1 hour at room temperature. The unbound streptavidin-horseradish peroxidase conjugate was removed by rinsing the plate 6 times with 1×PBS containing 0.1% Tween-20 and 3 times with 1×PBS. Next, the peroxidase substrate was prepared by diluting 20 mcL/mL of AEC Chromogen in AEC substrate solution (Catalog No. 551951, BD-Biosciences, San Diego Calif.). Color development was initiated by adding 100 mcL/well of substrate solution for 3-5 minutes. Finally, the plates were rinsed with water and were air-dried. The results were determined using an ELISPOT analyzer or imaging device that takes a picture of a single well of the ELISPOT plate and then the spots were enumerated. In this case, the resulting spots were counted using an Immunospot Reader (CTL Inc., Cleveland, Ohio). Peptide-specific IFN-γ ELISPOT responses were considered positive if the response (minus media background) was ≥3 fold above the media response and ≥50 spot forming cells excreting interferon gamma per $10^6$ splenocytes (#SFC/$10^6$ splenocytes).

As shown in Table 4, individual HIV-1 antigen and total HIV-specific IFN-gamma ELISPOT responses in mice after multi-plasmid DNA immunizations were measured after two immunizations with immunogenic compositions made up of the plasmids shown in Table 3.

TABLE 4

Murine Immune Responses Following Two Immunizations

| Group ID | gag-specific response* | pol-specific response | env-specific response | ntv#-specific response | Total HIV-specific response |
|---|---|---|---|---|---|
| Control | 2 | 0 | 3 | 0 | 5 |
| 1a | 46 | 43 | 238 | 4 | 331 |
| 2e | 29 | 138 | 181 | 12 | 360 |
| 2c | 102 | 118 | 203 | 44 | 467 |
| 1 | 20 | 39 | 468 | 2 | 529 |
| 3b | 16 | 109 | 404 | 20 | 548 |
| 2d | 188 | 185 | 251 | 8 | 632 |
| 2b | 43 | 65 | 548 | 6 | 662 |
| 3a | 139 | 105 | 802 | 18 | 1064 |
| 3c | 174 | 378 | 616 | 11 | 1179 |

*antigen-specific IFN-gamma ELISPOT responses were reported as the spot forming cells (#SFC/$10^6$ splenocytes) excreting interferon gamma per $10^6$ splenocytes.
ntv, nef-tat-vif fusion protein.

In all cases, the nef-tat-vif specific responses were relatively low. It was lowest in group 1 mice where nef-tat-vif was under the control of the lap1 promoter. However, in the above examples 4-7 it was found that HCMV promoter-driven gene expression was higher than with the SCMV promoter, and SCMV-promoter driven gene expression was higher than with the HSV-lap1 promoter. This difference in strength of the promoters being utilized in the triple promoter construct may be responsible for the lower induced immune responses observed when this construct was used in an immunogenic composition.

Regarding the use of fusion proteins, comparing the ELISPOT response to HIV pol in 3a and 3c, it appears that there is some reduced immunogenicity when fusion polypeptides are used rather than single polypeptides.

Another consideration is the relative immunogenicity of the protein being examined. For example, by examining 3b versus 3c (where HCMV promoter-driven gene expression drives each of the genes, env, gag, pol and nef-tat-vif, on a single plasmid containing a single transcription unit), there still remains a hierarchy of immunogenicty that is approximately env>pol>gag>nef-tat-vif. As discussed above, promoter strength and relative immunogenicity should both be considered in the design of individual plasmids and combinations of plasmids for use in immunogenic compositions.

Next, another study was performed to evaluate the effect on immune responses when three immunizations using one, two and three plasmid immunogenic compositions. See Table 5. Groups of six mice were immunized as described above, except that they were immunized three times at three-week intervals rather than two times at three-week intervals. See Table 5. Groups 1, 2e and 3a utilize the same immunogenic compositions as in Table 3. In addition, in the study using three immunizations a new plasmid, designated 301, was constructed to directly compare HCMV promoter-driven gene expression of a gag/pol fusion protein with SCMV promoter-driven gene expression of a gag/pol fusion protein. Compare groups 3a and 4b in Tables 5 and 6. This plasmid also allowed the comparison of the immunogenic potential of gag-pol fusion being expressed from a triple transcriptional unit plasmid with the gag-pol fusion and env genes being expressed from three single transcriptional unit plasmids driven by similar promoters. Compare groups 1 and 4b in Tables 5 and 6. Spleen tissue was harvested 17 days after the final boost and analyzed for antigen specific ELISPOT responses to the individual HIV proteins.

TABLE 5

Murine Study Design - Three Immunizations

| [1]Group No. | Plasmid No. | Plasmid description | Total DNA (ug) | No. mice | Immunization Schedule (week) |
|---|---|---|---|---|---|
| 1 | 303 | HCMV-env; SCMV-gag/pol; lap-ntv | 100 | 9 | 0 - 3 - 6 |
| 2e | 201 + | HCMV-pol, | 50 | 9 | 0 - 3 - 6 |
|  | 202 | SCMV-gag HCMV-ntv, SCMV-env | 50 |  |  |
| 3a | 111 | HCMV-gag/pol | 33 | 9 | 0 - 3 - 6 |
|  | 101 | HCMV-env | 33 |  |  |
|  | 104 | HCMV-ntv | 33 |  |  |
| 4b | 101 | HCMV-env | 33 | 9 | 0 - 3 - 6 |
|  | 104 | HCMV-ntv | 33 |  |  |
|  | 301 | SCMV-gag/pol, HCMV-[none], Lap1-[none] | 33 |  |  |
| control | 001 | Vector control | 100 | 6 | 0 - 3 - 6 |

[1]Groups 1, 2e and 3a utilize the same immunogenic compositions as in Table 3, except that three immunizations were carried out.

The total induced cellular immune responses from the three transcriptional unit plasmid were approximately the same or higher than cellular immune responses induced by immunogenic compositions containing single and double transcriptional unit plasmids. See Table 6.

TABLE 6

Murine Cellular Immune Responses - Three Immunizations

| Group ID | gag-specific response* | pol-specific response | env-specific response | ntv#-specific response | Total HIV-specific response |
|---|---|---|---|---|---|
| 1 | 34 | 58 | 986 | 1 | 1077 |
| 2e | 32 | 363 | 431 | 69 | 895 |
| 3a | 174 | 162 | 713 | 82 | 1131 |
| 4b | 47 | 35 | 722 | 79 | 883 |
| control | 0 | 0 | 3 | 2 | 5 |

*antigen-specific IFN-gamma ELISPOT responses were reported as the #SFC/$10^6$ splenocytes.
ntv, nef-tat-vif fusion protein.

The ELISPOT results of the following three immunizations of the immunogenic compositions indicated that HIV cellular immune responses after three immunizations with the three transcriptional unit plasmid-based immunogenic composition were increased by 100% following the third immunization. However, the balance of the response can still vary depending on the strength of the promoters involved and the relative immunogenicity of the antigens. Clearly, for some situations where a manufacturing advantage is necessary, the tripe transcriptional unit plasmid will be a good vehicle for administering three or more genes in an immunogenic composition.

All plasmid designs tested thus far in immunogenic compositions have been found to correctly express the antigens and to be immunogenic, activating cellular immune responses after three immunizations. However, nef, tat and vif specific responses were undetectable when placed under the control of HSV Lap1 promoter in the triple promoter construct.

Under some scenarios, immunogenic compositions which induce broad, and balanced cellular immune responses to a range of antigens would be preferable. In this case, two and three pDNA immunogenic composition designs (2d, 3a and 3c) as shown in Tables 3 and 4 appear capable of eliciting potent (>600 SFC/$10^6$ cells), balanced, HIV-specific ELISPOT responses and were selected for further testing in non-human Primates. See Example 9.

Example 9

Macaque Immunization Studies with Plasmid Vectors Containing One or Two Complete Transcriptional Units In Example 8, Tables 3 and 4, three pDNA immunogenic compositions, particularly the immunogenic compositions used in groups 2d, 3a and 3c, appeared capable of eliciting potent (>600 SFC/$10^6$ cells), balanced, HIV-specific ELISPOT responses to all six HIV proteins and were selected for further testing in non-human primates.

Experimental Design

For this study, a total of 30 Mamu-A*01 negative, captive-bred, male rhesus macaques (*Macaca mulatta*) of Indian origin were used. Macaques were housed at the New Iberia Research Center (New Iberia, La.) and maintained in accordance with the Guide for the Care and Use of Laboratory Animals (National Research Council, National Academic Press, Washington, D.C., 1996). In addition, procedures for the use and care of the macaques were approved by Wyeth Research's Institutional Animal Care and Use Committee.

Immunizations:

Expression plasmids for immunization were produced by Puresyn, Inc. (Malvern, Pa.). Plasmids were propagated in *E. coli*, isolated from cells by alkaline lysis, and purified by column chromatography. The plasmids were then individually formulated at a concentration of 2.5 mg/mL in isotonic citrate buffer (29.3 mM sodium citrate, 0.67 mM citric acid, 150 mM NaCl, 0.34 mM EDTA, pH=6.4-6.7) containing 0.25% bupivacaine to allow for the formation of DNA:bupivacaine complexes. Final plasmid preparations were shown to consist of >90% supercoiled plasmid DNA and residual endotoxin was shown to be <30 EU/mg DNA (data not shown).

The adjuvant used for the rhesus macaque studies was a DNA plasmid that was delivered as part of the immunogenic composition. This adjuvant plasmid is a two-trancriptional unit expression plasmid (plasmid no. 212 in Table 1) encoding rhesus IL-12 p35 and p40 genes. See Table 7. The IL-12 p35 subunit was expressed under control of the HCMV immediate early promoter and SV40 polyadenylation signal, while the IL-12 p40 subunit was expressed while under control of the simian CMV promoter (SCMV) and BGH polyadenylation signal. Bioactivity of the plasmid-expressed rhesus IL-12 was confirmed by assaying supernatants from transiently transfected RD cells for their capacity to induce IFN-γ secretion in resting rhesus peripheral blood lymphocytes (PBLs; data not shown).

TABLE 7

Macaque Study Design

| Group No. | Plasmid No. | [1]Plasmid description | Total DNA (ug) | No. animal |
|---|---|---|---|---|
| 2d | 111 + | HCMV-gag-pol | 4.25 | 6 |
| | 202 | HCMV-ntv, | 4.25 | |
| | 212 | SCMV-env HCMV-IL-12 p35, SCMV-IL-12 p40 | 1.5 | |
| 3a | 111 | HCMV-gag/pol | 2.8 | 6 |
| | 101 | HCMV-env | 2.8 | |
| | 104 | HCMV-ntv | 2.8 | |
| | 212 | HCMV-IL-12 p35, SCMV-IL-12 p40 | 1.5 | |
| 3c | 102 | HCMV-gag | 2.8 | 6 |
| | 103 | HCMV-pol | 2.8 | |
| | 202 | HCMV-ntv, SCMV-env | 2.8 | |
| | 212 | HCMV-IL-12 p35, SCMV-IL-12 p40 | 1.5 | |
| 3cE[2] | 102 | HCMV-gag | 0.56 | 6 |
| | 103 | HCMV-pol | 0.56 | |
| | 202 | HCMV-ntv, SCMV-env | 0.56 | |
| | 212 | HCMV-IL-12 p35, SCMV-IL-12 p40 | 0.30 | |
| 4a[3] | 102 | HCMV-gag | 2.1 | 6 |
| | 101 | HCMV-env | 2.1 | |
| | 103 | HCMV-pol | 2.1 | |
| | 104 | HCMV-ntv | 2.1 | |
| | 212 | HCMV-IL-12 p35, SCMV-IL-12 p40 | 1.5 | |
| 4 -- control | 001 | Vector control | 8.5 | 6 |
| | 212 | HCMV-IL-12 p35, SCMV-IL-12 p40 | 1.5 | |

[1]All groups received 1.5 mg of plasmid no. 212 (HCMV-IL-12 p35, SCMV-IL-12 p40) encoding rhesus macaque IL-12 (rIL-12) as adjuvant.
[2]A second Group 3c was included where electroporation was added to the administration protocol.
[3]An additional group (4a) was added to the macaque study at a later time to determine the immunogenicity of the indicated 4 vector vaccine design.

All macaques were immunized on a schedule of 0, 4, and 8 weeks. Immediately prior to immunization, the appropriate plasmid expression vector formulations were mixed to create immunogenic compositions and administered by intramuscular injection (groups 2d, 3a, 3c and controls) into both deltoid muscles and both quadriceps muscles (1 ml injection volume, 2.5 mg DNA per site) using an 18 gauge needle and 3 mL syringe.

Group 3cE macaques were immunized with pDNA by intramuscular injection into both deltoid muscles and both quadriceps muscles using standard 1 mL syringes with 21 gauge needles (Braun) positioned 8.0 mm apart and, followed immediately by electrostimulation (i.e., electroporation). The injection volume was 0.2 ml providing 0.5 mg plasmid DNA per site per injection for a total of 2 mg total DNA. Therefore, the electroporation group (3cE) received ⅕ the total DNA administered to the other groups.

In this example, the electroporation conditions were as follows: six 20 ms unipolar pulses at 250 mA and about 100 V/cm. There was a 250 ms pause between each pulse.

In the absence of electroporation, the results shown in Table 8 indicated that immunogenic compositions based on a combination of plasmids having a single transcriptional unit (group 3a) produced the highest total cellular immune responses after ten or sixteen weeks as compared to immunogenic compositions based on a combination of plasmids containing at least one plasmid with more than one transcriptional unit. Compare 3a with 2d and 3c.

A surprising result was that electroporation enhanced the total cellular immune responses by more than 450% at ten weeks and by more that 990% at sixteen weeks. Compare 3cE with 3c. The results shown in Table 8 indicated that immunogenic compositions based on a combination of plasmids containing at least one plasmid with more than one transcriptional unit when combined with electroporation produced the highest total cellular immune responses after ten or sixteen weeks as compared to immunogenic compositions based on a combination of plasmids having a single transcriptional unit. Compare group 3c and group 3a.

In the macaque study, excluding the use of electroporation, group 3a developed the highest ten or sixteen week total HIV antigen-specific ELISPOT responses (1,652 and 1015 SFC/$10^6$ cells). This response was not statistically different relative to group 2d (770 SFC/$10^6$ cells) or group 3c (787 SFC/$10^6$ cells). See Table 8. However, the highest ELISPOT response was achieved with the use of electroporation. See group 3cE in Table 8.

Interestingly, the peak immune response following booster immunizations where electroporation was used was later than for the non-electroporation groups. For example, the total HIV specific IFN-gamma ELIspot response for group 3a animals peaked around week 6 following the week 4 immunization or boost. See Table 8. In contrast, for the electroporation group, the peak was closer to week 10. See Table 8.

The cellular immune response was further analyzed as IFN-gamma ELISPOT responses to the six HIV proteins. Table 9 shows IFN-gamma ELISPOT responses to the HIV env, gag, pol and a fusion protein of nef-tat-vif proteins. In the macaque study, again excluding the use of electroporation, group 3a developed the highest ten-week HIV antigen-specific ELISPOT responses to env and nef-tat-vif. See Table 9. Group 3c animals developed the highest ELISPOT response to gag and group 2d developed the highest ELISPOT response to pol protein. Compare 3a with 2d and 3c in Table 9. By far the highest ELISPOT response was achieved with the use of electroporation. See group 3cE in Table 9.

TABLE 8

Total HIV-Specific IFN-Gamma ELISPOT Responses Over Time After Multi-Plasmid DNA Vaccination

| Group ID | Baseline | Week 2 | Week 4 | Week 6 | Week 8 | Week 10 | Week 16 |
|---|---|---|---|---|---|---|---|
| 2d | 43.8 ± 10.5 | 286.5 ± 234.9 | 278.7 ± 104.5 | 403.1 ± 89.9 | 348.3 ± 108.8 | 769.9 ± 340.4 | 407.5 ± 82.2 |
| 3a | 29.5 ± 12.8 | 61.5 ± 23.2 | 204.8 ± 26.4 | 635.0 ± 230.5 | 365.8 ± 47.1 | 1652.5 ± 563.3 | 1015.3 ± 584.8 |
| 3c | 35.5 ± 9.0 | 56.5 ± 12.3 | 138.3 ± 32.5 | 892.5 ± 277.5 | 300.0 ± 95.9 | 786.7 ± 213.1 | 816.3 ± 330.6 |
| 3cE | 41.5 ± 13.6 | 1405.0 ± 422.0 | 346.3 ± 72.7 | 1287.9 ± 365.6 | 3349.6 ± 1575.9 | 3637.8 ± 863.7 | 8140.8 ± 1819.0 |
| 4a | 18.8 ± 8.2 | 52.1 ± 13.3 | 43.3 ± 16.6 | 272.9 ± 60.0 | 230.0 ± 40.5 | 190.6 ± 38.9 | nd[1] |
| control | 32.0 ± 12.5 | 10.2 ± 2.7 | 33.2 ± 12.0 | 24.2 ± 9.3 | 16.7 ± 4.0 | 12.1 ± 4.1 | 47.1 ± 13.7 |

*Total HIV-specific IFN-gamma ELISpot responses are reported as the mean #SFC/$10^6$ PBLs ± standard error.
[1]nd, not done

TABLE 9

Individual HIV Antigen-Specific IFN-Gamma ELISPOT Responses At Week 10 After Multi-Plasmid DNA Vaccination

| Group ID | Antigen-specific IFN-gamma ELISPOT response* | | | | |
|---|---|---|---|---|---|
| | Env | Gag | Pol | ntv | total |
| 2d | 360.4 ± 111.8 | 107.9 ± 45.2 | 204.0 ± 182.6 | 97.6 ± 67.6 | 769.9 ± 340.4 |
| 3a | 1170.4[1] ± 427.0 | 43.8 ± 17.5 | 173.8 ± 97.7 | 264.6[3] ± 113.8 | 1652.5 ± 563.3 |
| 3c | 412.0 ± 131.7 | 246.43[2] ± 59.7 | 106.7 ± 60.5 | 21.7 ± 8.9 | 786.7 ± 213.1 |
| 3cE | 861.1 ± 292.5 | 1147.9 ± 356.9 | 1023.1 ± 384.0 | 605.7 ± 159.3 | 3637.8 ± 863.7 |
| 4a | 132.9 ± 33.9 | 29.4 ± 6.5 | 9.1 ± 5.4 | 19.2 ± 7.9 | 190.6 ± 38.9 |
| control | 7.1 ± 3.4 | 1.7 ± 0.8 | 2.5 ± 1.1 | 0.8 ± 0.5 | 12.1 ± 4.1 |

*individual HIV antigen-specific IFN-gamma ELISPOT responses are reported as the mean #SFC/$10^6$ PBIs ± standard error.
[1]Statistically higher env-specific ELISPOT response relative to group 2d ($p < 0.05$).
[2]Statistically higher gag-specific ELISPOT response relative to group 3a ($p < 0.05$).
[3]Statistically higher ntv-specific ELISPOT response relative to group 3c ($p < 0.05$).

Table 10 shows IFN-gamma ELISPOT responses to the HIV env, gag, pol and a fusion protein of nef-tat-vif proteins at week sixteen, 8 weeks after the last immunization. Excluding the use of electroporation, group 3a developed the highest sixteen-week HIV antigen-specific ELISPOT responses to env and nef-tat-vif, while group 3c developed the highest ten-week HIV antigen-specific ELISPOT responses to gag and pol. The highest ELISPOT response was achieved with the use of electroporation. See group 3cE in Table 10.

Tables 9 and 10 show that increasing the number of antigen expressing plasmids from 3 to 4 in the immunogenic composition decreased immune response to all of the HIV proteins. See Tables 9 and 10.

Tables 9 and 10 also show that the plasmids in group 2d with two antigen expressing plasmids in the immunogenic composition, where one plasmid has two transcriptional units, induced the broadest and most balanced immune response to all of the HIV proteins. See Tables 9 and 10.

to gag. Compare 3a with 2d and 3c in Table 11. The highest ELISPOT response was achieved with the use of electroporation. See group 3cE in Table 11.

In both the mouse and macaque studies, antigen-specific ELISPOT responses were generally highest in groups receiving each individual gene by itself under control of the HCMV promoter. In the macaque study, electroporation was a more important factor in producing immune responses than whether the immunogenic composition contained plasmids having one versus two complete transcriptional units or whether fusion proteins were used.

TABLE 10

Individual HIV antigen-specific IFN-gamma ELISpot responses at week 16 after multi-plasmid DNA vaccination.

| Group ID | Antigen-specific IFN-gamma ELISpot response* | | | | |
|---|---|---|---|---|---|
| | Env | Gag | Pol | ntv | total |
| 2d | 217.5 ± 33.3 | 76.3 ± 25.8 | 81.3 ± 32.2 | 32.5 ± 14.3 | 407.5 ± 82.2 |
| 3a | 831.0 ± 457.8 | 39.7 ± 35.6 | 80.2 ± 68.7 | 64.3 ± 25.6 | 1015.3 ± 584.8 |
| 3c | 437.5 ± 187.9 | 250.0 ± 88.2 | 96.3 ± 68.0 | 32.5 ± 10.7 | 816.3 ± 330.6 |
| 3cE | 1984.7 ± 698.1 | 1975.3 ± 567.2 | 2305.6 ± 786.2 | 1875.3 ± 624.4 | 8140.8 ± 1819.0 |
| 4a | nd[1] | nd | nd | nd | nd |
| control | 22.5 ± 7.2 | 5.0 ± 2.3 | 9.2 ± 3.6 | 10.4 ± 4.4 | 47.1 ± 13.7 |

*individual HIV antigen-specific IFN-gamma ELISpot responses are reported as the mean #SFC/$10^6$ PBLs ± standard error.
[1]nd, not done Table 11 shows IFN-gamma ELISPOT responses to the HIV env, gag, pol and a fusion protein of nef-tat-vif proteins at thirty weeks, 22 weeks after the last immunization. In the macaque study, again excluding the use of electroporation, group 3a developed the highest HIV antigen-specific ELISPOT responses to env, pol and nef-tat-vif. See Table 11. Group 3c animals developed the highest ELISPOT response

TABLE 11

Individual HIV antigen-specific IFN-gamma ELISpot responses at week 30 after multi-plasmid DNA vaccination.

| Group ID | Antigen-specific IFN-gamma ELISpot response* | | | | |
|---|---|---|---|---|---|
| | Env | Gag | Pol | ntv | total |
| 2d | 44.2 ± 11.6 | 6.7 ± 3.1 | 8.8 ± 6.3 | 4.6 ± 3.6 | 64.2 ± 16.0 |
| 3a | 184.0 ± 105.4 | 5.6 ± 3.7 | 14.0 ± 6.9 | 10.2 ± 4.7 | 213.9 ± 119.1 |
| 3c | 52.5 ± 11.7 | 25.4 ± 6.6 | 2.9 ± 2.0 | 0.8 ± 0.8 | 81.7 ± 19.6 |
| 3cE | 831.3 ± 339.1 | 768.9 ± 216.7 | 907.4 ± 476.5 | 886.4 ± 371.8 | 3,393.9 ± 920.4 |
| 4a[1] | nd | nd | nd | nd | nd |
| control | 9.6 ± 4.8 | 0.0 ± 0.0 | 1.6 ± 1.2 | 0.0 ± 0.0 | 11.3 ± 5.8 |

*individual HIV antigen-specific IFN-gamma ELISpot responses were reported as the mean #SFC/$10^6$ PBLs ± standard error.
[1]Not done Cellular Immune Response To Individual HIV Proteins Over Time IFN-gamma ELISPOT responses were measured at weeks 2, 4, 6, 8, 10 and 16 to individual HIV proteins env, gag, pol, nef, tat, and vif following immunization with the plasmids described in Table 7. The results are presented in Tables 12-17.

TABLE 12

HIV env-specific IFN-gamma ELISpot responses over time after multi-plasmid DNA vaccination.

HIV env-specific IFN-gamma ELISpot response*

| Group ID | Baseline | Week 2 | Week 4 | Week 6 | Week 8 | Week 10 | Week 16 |
|---|---|---|---|---|---|---|---|
| 2d | 17.7 ± 4.5 | 204.0 ± 162.8 | 182.3 ± 64.8 | 295.1 ± 60.9 | 209.6 ± 66.1 | 360.4 ± 111.8 | 217.5 ± 33.3 |
| 3a | 5.3 ± 2.2 | 43.8 ± 19.6 | 165.3 ± 20.6 | 577.9 ± 224.5 | 308.8 ± 38.6 | 1170.4 ± 427.0 | 831.0 ± 457.8 |
| 3c | 21.0 ± 8.4 | 26.3 ± 7.1 | 84.8 ± 20.2 | 538.3 ± 174.2 | 192.1 ± 71.1 | 412.1 ± 131.7 | 437.5 ± 187.9 |
| 3cE | 23.2 ± 9.5 | 598.3 ± 203.9 | 144.2 ± 30.9 | 382.9 ± 87.2 | 1165.8 ± 647.7 | 861.1 ± 295.5 | 1984.7 ± 698.1 |
| 4a | 14.6 ± 8.7 | 24.2 ± 10.1 | 22.1 ± 9.6 | 254.2 ± 57.5 | 169.2 ± 33.5 | 132.9 ± 33.9 | nd[1] |
| control | 13.7 ± 5.4 | 3.0 ± 1.6 | 17.2 ± 9.0 | 17.1 ± 6.0 | 9.2 ± 2.6 | 7.1 ± 3.4 | 22.5 ± 7.2 |

*HIV env-specific IFN-gamma ELISpot responses were reported as the mean #SFC/$10^6$ PBLs ± standard error.
[1]nd, not done

TABLE 13

HIV gag-specific IFN-gamma ELISpot responses over time after multi-plasmid DNA vaccination.

HIV gag-specific IFN-gamma ELISpot response*

| Group ID | Baseline | Week 2 | Week 4 | Week 6 | Week 8 | Week 10 | Week 16 |
|---|---|---|---|---|---|---|---|
| 2d | 6.8 ± 1.5 | 23.5 ± 16.7 | 36.0 ± 18.3 | 28.1 ± 5.7 | 59.6 ± 31.2 | 107.9 ± 45.2 | 76.3 ± 25.8 |
| 3a | 2.2 ± 1.0 | 9.0 ± 3.4 | 21.5 ± 4.9 | 17.5 ± 11.5 | 10.0 ± 2.7 | 43.8 ± 17.5 | 39.7 ± 35.6 |
| 3c | 4.5 ± 2.1 | 19.0 ± 6.7 | 51.7 ± 15.6 | 229.6 ± 67.0 | 86.7 ± 21.8 | 246.3 ± 59.7 | 250.0 ± 88.2 |
| 3cE | 4.8 ± 2.9 | 709.6 ± 244.1 | 161.3 ± 38.3 | 381.7 ± 78.5 | 1169.6 ± 551.6 | 1147.9 ± 356.9 | 1975.3 ± 567.2 |
| 4a | 2.1 ± 8.7 | 12.4 ± 3.7 | 5.4 ± 2.4 | 10.0 ± 4.0 | 27.5 ± 6.2 | 29.4 ± 6.5 | nd[1] |
| control | 3.2 ± 2.2 | 1.0 ± 0.6 | 7.7 ± 4.5 | 1.7 ± 0.8 | 2.1 ± 1.2 | 1.7 ± 0.8 | 5.0 ± 2.3 |

*HIV gag-specific IFN-gamma ELISpot responses are reported as the mean #SFC/$10^6$ PBLs ± standard error.
[1]nd, not done

TABLE 14

HIV pol-specific IFN-gamma ELISpot responses over time after multi-plasmid DNA vaccination.

HIV pol-specific IFN-gamma ELISpot response*

| Group ID | Baseline | Week 2 | Week 4 | Week 6 | Week 8 | Week 10 | Week 16 |
|---|---|---|---|---|---|---|---|
| 2d | 12.2 ± 4.3 | 33.8 ± 31.3 | 27.7 ± 7.6 | 53.3 ± 32.3 | 41.7 ± 25.1 | 204.0 ± 182.6 | 81.3 ± 32.2 |
| 3a | 7.3 ± 4.1 | 1.8 ± 0.9 | 7.3 ± 2.9 | 17.5 ± 7.9 | 15.0 ± 4.5 | 173.8 ± 97.7 | 80.2 ± 68.7 |
| 3c | 6.5 ± 3.4 | 3.5 ± 2.1 | 1.8 ± 1.3 | 102.1 ± 42.3 | 17.1 ± 6.8 | 106.7 ± 60.5 | 96.3 ± 68.0 |
| 3cE | 3.7 ± 2.4 | 54.6 ± 30.5 | 22.1 ± 9.1 | 316.3 ± 215.8 | 497.9 ± 179.7 | 1023.1 ± 384.0 | 2305.6 ± 786.2 |
| 4a | 1.7 ± 1.1 | 9.3 ± 6.8 | 2.5 ± 1.3 | 5.4 ± 2.0 | 13.8 ± 4.8 | 9.1 ± 5.4 | nd[1] |
| control | 10.7 ± 4.4 | 3.2 ± 2.8 | 4.7 ± 3.0 | 2.1 ± 1.6 | 4.2 ± 2.7 | 2.5 ± 1.1 | 9.2 ± 3.6 |

*HIV pol-specific IFN-gamma ELISpot responses are reported as the mean #SFC/$10^6$ PBLs ± standard error.
[1]nd, not done

TABLE 15

HIV nef-specific IFN-gamma ELISpot responses over time after multi-plasmid DNA vaccination.

HIV nef-specific IFN-gamma ELISpot response*

| Group ID | Baseline | Week 2 | Week 4 | Week 6 | Week 8 | Week 10 | Week 16 |
|---|---|---|---|---|---|---|---|
| 2d | 4.8 ± 3.2 | 16.3 ± 16.3 | 22.5 ± 16.7 | 12.4 ± 6.0 | 32.9 ± 14.4 | 43.7 ± 27.6 | 24.6 ± 12.3 |
| 3a | 20.1 ± 9.8 | 2.5 ± 2.0 | 7.9 ± 3.6 | 13.8 ± 5.2 | 22.5 ± 9.8 | 192.1 ± 76.7 | 54.8 ± 25.4 |

TABLE 15-continued

HIV nef-specific IFN-gamma ELISpot responses over time after multi-plasmid DNA vaccination.

| Group ID | Baseline | Week 2 | Week 4 | Week 6 | Week 8 | Week 10 | Week 16 |
|---|---|---|---|---|---|---|---|
| 3c | 4.2 ± 4.2 | 0.4 ± 0.4 | 0.0 ± 0.0 | 10.4 ± 7.5 | 3.3 ± 2.5 | 10.0 ± 8.1 | 18.3 ± 9.6 |
| 3cE | 5.1 ± 3.4 | 11.9 ± 7.2 | 11.7 ± 7.7 | 67.1 ± 56.6 | 281.7 ± 207.0 | 403.2 ± 158.3 | 1276.2 ± 516.3 |
| 4a | 0.4 ± 0.4 | 1.7 ± 1.4 | 5.4 ± 3.1 | 2.1 ± 2.1 | 10.4 ± 5.0 | 8.3 ± 4.4 | nd[1] |
| control | 3.6 ± 2.8 | 0.8 ± 0.8 | 0.8 ± 0.8 | 0.0 ± 0.0 | 0.0 ± 0.0 | 0.0 ± 0.0 | 2.9 ± 1.5 |

*HIV nef-specific IFN-gamma ELISpot responses are reported as the mean #SFC/$10^6$ PBLs ± standard error.
[1]nd, not done

TABLE 16

HIV tat-specific IFN-gamma ELISpot responses over time after multi-plasmid DNA vaccination.

| Group ID | Baseline | Week 2 | Week 4 | Week 6 | Week 8 | Week 10 | Week 16 |
|---|---|---|---|---|---|---|---|
| 2d | 7.1 ± 3.3 | 0.8 ± 0.5 | 7.1 ± 4.2 | 8.5 ± 3.3 | 2.9 ± 2.1 | 4.6 ± 2.1 | 3.8 ± 1.4 |
| 3a | 10.0 ± 5.3 | 3.8 ± 2.3 | 2.9 ± 1.2 | 4.2 ± 2.0 | 8.8 ± 7.3 | 14.6 ± 8.2 | 1.7 ± 1.2 |
| 3c | 6.2 ± 4.5 | 6.3 ± 2.9 | 0.4 ± 0.4 | 8.3 ± 3.5 | 0.4 ± 0.4 | 1.3 ± 1.3 | 2.9 ± 1.2 |
| 3cE | 7.6 ± 5.2 | 22.4 ± 13.8 | 2.1 ± 1.0 | 25.0 ± 17.8 | 75.0 ± 42.4 | 29.3 ± 19.9 | 190.0 ± 88.4 |
| 4a | 0.0 ± 0.0 | 1.8 ± 1.5 | 5.8 ± 2.9 | 1.3 ± 1.3 | 5.8 ± 3.7 | 10.3 ± 6.1 | nd[1] |
| control | 5.1 ± 4.5 | 0.8 ± 0.5 | 2.1 ± 1.6 | 3.3 ± 1.5 | 0.0 ± 0.0 | 0.0 ± 0.0 | 2.1 ± 1.2 |

*HIV tat-specific IFN-gamma ELISpot responses are reported as the mean #SFC/$10^6$ PBLs ± standard error.
[1]nd, not done

TABLE 17

HIV vif-specific IFN-gamma ELISpot responses over time after multi-plasmid DNA vaccination.

| Group ID | Baseline | Week 2 | Week 4 | Week 6 | Week 8 | Week 10 | Week 16 |
|---|---|---|---|---|---|---|---|
| 2d | 9.4 ± 3.9 | 7.9 ± 7.9 | 3.3 ± 2.9 | 5.8 ± 2.7 | 1.7 ± 1.2 | 8.7 ± 8.1 | 4.2 ± 1.9 |
| 3a | 12.9 ± 8.5 | 0.4 ± 0.4 | 0.4 ± 0.4 | 4.2 ± 2.3 | 0.8 ± 0.8 | 12.1 ± 12.1 | 7.8 ± 2.7 |
| 3c | 6.4 ± 4.8 | 0.8 ± 0.5 | 0.0 ± 0.0 | 3.8 ± 2.0 | 0.4 ± 0.4 | 2.5 ± 2.5 | 11.3 ± 3.3 |
| 3cE | 8.9 ± 5.9 | 8.2 ± 5.1 | 5.0 ± 2.6 | 115.0 ± 51.6 | 159.6 ± 64.8 | 173.2 ± 103.6 | 409.1 ± 129.9 |
| 4a | 0.0 ± 0.0 | 2.8 ± 1.8 | 2.1 ± 0.8 | 0.0 ± 0.0 | 3.3 ± 1.1 | 0.6 ± 0.2 | nd[1] |
| control | 6.8 ± 2.2 | 1.2 ± 0.8 | 0.8 ± 0.8 | 0.0 ± 0.0 | 1.3 ± 1.3 | 0.0 ± 0.0 | 5.4 ± 3.1 |

*HIV vif-specific IFN-gamma ELISpot responses are reported as the mean #SFC/$10^6$ PBLs ± standard error.
[1]nd, not done Tables 12-17, which show immune responses to individual proteins over time indicate that increasing the number of antigen expressing plasmids from 3 to 4 in the immunogenic composition, resulted in decreased immune response to all of the HIV proteins at this given concentration of DNA administered. See Tables 12-17.

Example 10

Estimation of the Percentage of HIV Specific CTL and Helper Cells

The relative amounts of HIV specific CTL and helper cells were estimated by first depleting unfractionated peripheral blood lymphocytes (PBLs) of CD4+ or CD8+ cells prior to measuring total HIV-specific IFN-gamma ELISpot responses at weeks 10 and 16.

Preparation of Bead Depleted PBLs

CD4+ or CD8+ cells were depleted from unfractionated PBLs using magnetic polystyrene beads coated with anti-human CD4- or CD8-specific mouse monoclonal antibodies, as per the manufacturer's instructions (Dynal Biotech, Oslo, Norway). Briefly, freshly isolated rhesus PBLs were washed and resuspended to a final concentration of $2 \times 10^6$ cells/mL in ice cold 1×PBS containing 2% FBS. Dynal microbeads coated with either anti-human CD4- or anti-CD8-specific mouse monoclonal antibodies were washed three times with 1×PBS containing 2% FCS then added to unfractionated PBLs at a 5:1 bead to cell ratio, and incubated for one hour at 4° C. on a rotating/tilting apparatus. After incubation, the bead/cell suspension was placed in a magnetic column, and the flow through containing either CD4+ or CD8+ cell depleted PBLs was collected. The cells were washed once with complete culture medium supplemented with 5% FBS, and resuspended to the original volume with complete culture medium supplemented with 5% FBS. Equal volumes of unfractionated, and bead depleted PBLs, were used directly in the ELISpot assay.

The efficiency of CD4+ and CD8+ cell subset depletion and the precise numbers of CD4+ and CD8+ cells added to the ELISpot plate were subsequently quantified by flow cytometry. Briefly, bead depleted PBLs were washed once with 1×PBS containing 2% FBS and stained for 15 minutes at room temperature with the following monoclonal antibodies: anti-rhesus macaque CD3-fluorescein isothiocyanate (FITC, clone SP34; BD Pharmingen, San Jose, Calif.); anti-human CD4-phycoerythrin (PE, clone M-T477; BD Pharmingen, San Jose, Calif.); anti-human CD8-peridinin chlorophyll protein (PerCP; clone SK1; BD Pharmingen, San Jose, Calif.); and anti-human CD20-allophycocyanin (APC, clone L27; BD Pharmingen, San Jose, Calif.). Cells were then washed once with 1×PBS containing 2% FBS, 0.02% azide and resuspended in 1×PBS containing 1% paraformaldehyde. FACS analysis was performed on a FACSCalibur Flow Cytometer (Becton Dickinson, Franklin Lakes, N.J.) and analyzed using CellQuest Software. The percent CD4+ or CD8+ cell depletion was routinely >95% (data not shown).

ability complex (MHC) Class I antigen processing pathway. The class I antigen processing pathway is critical for the induction of CD8+ T-cell mediated immune responses. However, conventional protein based subunit ICs typically outperform DNA based ICs in terms of their ability to elicit antigen-specific antibody responses.

For the determination of HIV viral lysate-specific antibody titers, ELISA plates were coated for 18 hours at 4° C. with detergent disrupted HIV-1$_{MN}$ at 20 ng/well, (Advanced Biotechnologies, Columbia, Md.). The detergent disrupted HIV-1$_{MN}$ was diluted in carbonate/bicarbonate buffer (15 mM Na$_2$CO$_3$, 35 mM NaHCO$_3$, pH 9.6). For the determination of HIV env-specific antibody titers, ELISA plates were coated with purified HIV-1 6101 gp120 (kindly provided by Larry Liao, Duke University, 20 ng/well) diluted in 1×PBS. Following the 18 hour incubation with HIV proteins, the ELISA plates were then washed five times with 1×PBS containing 0.1% Tween 20 and blocked for 2 hours at room temperature with 1×PBS containing 0.1% Tween 20 and 3% BSA. Serum samples from immunized and control animals were diluted with 1×PBS containing 1% BSA and 0.1% Tween-20, added to the ELISA plates at a starting dilution of 1:100 and further diluted 3-fold across the plates. The diluted

TABLE 18

Total HIV-specific IFN-gamma ELISpot responses at week 10 and 16 in unfractionated and CD4+ or CD8+ cell depleted PBLs.

| Group ID | Week 10 | | | Week 16 | | |
| --- | --- | --- | --- | --- | --- | --- |
| | Unfrac | CD4 depleted | CD8 depleted | Unfrac | CD4 depleted | CD8 depleted |
| 2d | 1,501 ± 632 | 1,494 ± 801 | 364 ± 77 | 902 ± 173 | 758 ± 141 | 431 ± 93 |
| 3a | 2,524 ± 789 | 1,239 ± 662 | 997 ± 222 | 1,821 ± 906 | 1,059 ± 689 | 539 ± 175 |
| 3c | 1,484 ± 359 | 908 ± 268 | 536 ± 147 | 1,532 ± 556 | 856 ± 308 | 607 ± 203 |
| 3cE | 6,651 ± 1,326 | 10,563 ± 3,388 | 1,921 ± 274 | 13,361 ± 2,770 | 21,051 ± 7,067 | 2,754 ± 543 |
| 4a | 1,591 ± 281 | 688 ± 119 | 954 ± 248 | nd[1] | nd | nd |
| control | 6 ± 2 | 31 ± 10 | 34 ± 15 | 187 ± 12 | 107 ± 31 | 118 ± 24 |

*Total HIV-specific IFN-gamma ELISpot responses are reported as the mean #SFC/10$^6$ unfractionated, CD4+ or CD8+ depleted PBLs ± standard error.
[1]nd, not done The results shown in Table 18 provide an estimate of the relative percentage of HIV specific CTL cells versus helper cells participating in a particular induced immune response. A few general observations may be drawn from the data. First groups 2d, 3a and 3c elicit similar magnitudes of cellular immune response to HIV. Group 3a appears to induce a higher level of immune response, but the amount of variation in the assay is also greater with that group. Where electroporation was used in conjunction with immunization, the magnitude of the immune response to the plasmids in group 3c was enhanced by about 5 fold to about 10 fold. See Table 18, compare 3cE and 3c. It is also worthy of note that many more cells were participating in the immune response as a result of the use of electroporation with the immunization.

Example 11

HIV Specific Antibody Titers Induced by Multi-Plasmid Immunization

An immunogenic composition (IC) containing plasmid DNA provides several advantages over other types of immunogenic composition technologies currently in use. For example, DNA based ICs, in contrast to conventional protein based subunit ICs, allow for the encoded antigen to be efficiently processed and presented by the major histocompatserum samples were incubated overnight at 4° C. with the protein coated plates. Detection of antigen-specific immunoglobulin was accomplished by incubating a biotin conjugated primary antibody specific for primate IgG for 2 hours at room temp. This antibody was diluted 1:30,000 with 1×PBS supplemented with 0.1% Tween-20, 1% BSA, Accurate Scientific, Westbury, N.Y. Next, the primary antibody was washed away and followed with a 1 hour room temperature incubation of streptavidin-horseradish peroxidase conjugated anti-biotin secondary antibody (500 units/ml stock, diluted 1:10,000 with 1×PBS supplemented with 0.1% Tween-20, 1% BSA, Roche Immunochemical, Indianapolis, Ind.). Finally, color was developed by the addition of 100 mcL/well of TMB (3,3',5,5'-tetramethyl benzidine, Sigma). Antigen-specific antibody titers were defined as the reciprocal of the last serum dilution giving an O.D.$_{450}$ greater than the same animal's naïve serum (i.e. week 0)+3 standard deviations.

HIV envelope titers for certain time points over the first 16 weeks of multi-plasmid DNA immunizations were determined and are shown in Table 19. HIV-1 6101 env gp120 ELISA titers were calculated as the reciprocal of the last serum dilution giving an O.D.$_{450}$ greater than the same animal's naïve serum (i.e. week 0)+3 standard deviations. The data in Table 19 (as well as in Table 20 below) were presented as the mean log$_{10}$ titer±standard error of the mean. In this case, HIV-1 env titers≤2.00 represent an endpoint titer of less than 1:100 and were below the limit of detection.

TABLE 19

HIV-1 6101 env gp120 specific ELISA antibody titers over time after multi-plasmid DNA Immunization.

| Group[1] ID | HIV-1 env ELISA titer* | | | | | |
|---|---|---|---|---|---|---|
| | Week 2 | Week 4 | Week 6 | Week 8 | Week 10 | Week 16 |
| 2d | 2.00 ± 0.00 | 2.00 ± 0.00 | 2.08 ± .035 | 2.43 ± 0.21 | 2.73 ± 0.27 | 2.59 ± 0.20 |
| 3a | 2.00 ± 0.00 | 2.00 ± 0.00 | 2.16 ± 0.10 | 2.64 ± 0.32 | 2.95 ± 0.28 | 2.56 ± 0.29 |
| 3c | 2.00 ± 0.00 | 2.00 ± 0.00 | 2.16 ± 0.16 | 2.48 ± 0.21 | 2.80 ± 0.32 | 2.95 ± 0.37 |
| 3cE | 2.16 ± 0.16 | 2.72 ± 0.16 | 4.39 ± 0.49 | 3.67 ± 0.44 | 5.18 ± 0.20 | 4.78 ± 0.23 |
| 4a | nd[1] | nd | nd | nd | nd | nd |
| control | 2.00 ± 0.00 | 2.08 ± 0.08 | 2.00 ± 0.00 | 2.16 ± 0.10 | 2.16 ± 0.16 | 2.32 ± 0.16 |

*Data were reported as the mean $\log_{10}$ titer ± standard error of the mean. HIV-1 env titers ≤2.00 represent an endpoint titer of less than 1:100 and were below the limit of detection.
[1]nd indicates not done As shown in Table 19, group 3c animals immunized with immunogenic compositions based on a combination of plasmids containing at least one plasmid with more than one transcriptional unit achieved the highest non-electroporation titers at week 16. However, the results for groups 2d and 3a were somewhat similar, but with groups 3a animals showing the highest titers at weeks 8 and 10. See Table 19, compare 3a with 2d and 3c. An immunogenic composition based on a combination of plasmids containing at least one plasmid with more than one transcriptional unit and receiving electroporation-electrostimulation with immunization developed by far the highest titers to the HIV envelope protein. See Table 19, Compare 3c with 3cE.

Total HIV titers to whole virus lysate was determined for weeks 2, 4, 6, 8, 10, and 16 weeks of multi-plasmid DNA immunizations are shown in Table 20. HIV-1$_{MN}$ viral lysate-specific ELISA titers were determined as the reciprocal of the last serum dilution giving an O.D.$_{450}$ greater than the same macaque's naïve serum (i.e. pre-immune)+3 standard deviations. In this table, the data were reported as the mean $\log_{10}$ titer±standard error of the mean. Note that antibody titers≤1.70 represent an endpoint titer of less than 1:50 and were below the limit of detection. The results in Table 20 at week 16 were similar to these presented in Table 19.

Example 12

Effect of Multi-Plasmid Immunization on Various Serological Parameters and Body Weight in Macaques The peripheral blood white blood cell counts (WBC) in macaques used in the study were determined over time by complete blood count analysis and reported as the mean WBC (×1000/ml)±standard error. See Table 21.

TABLE 20

Total HIV-1-specific ELISA antibody titers over time after multi-plasmid DNA vaccination.

| Group ID | Total HIV-1 ELISA titer* | | | | | |
|---|---|---|---|---|---|---|
| | Week 2 | Week 4 | Week 6 | Week 8 | Week 10 | Week 16 |
| 2d | 1.70 ± 0.00 | 1.70 ± 0.00 | 1.75 ± 0.05 | 1.75 ± 0.05 | 2.04 ± 0.28 | 1.70 ± 0.00 |
| 3a | 1.75 ± 0.05 | 1.75 ± 0.05 | 1.70 ± 0.00 | 1.70 ± 0.00 | 1.70 ± 0.00 | 1.70 ± 0.00 |
| 3c | 2.06 ± 0.19 | 2.11 ± 0.18 | 1.75 ± 0.05 | 1.88 ± 0.13 | 1.85 ± 0.07 | 1.90 ± 0.06 |
| 3cE | 1.88 ± 0.13 | 1.88 ± 0.13 | 3.46 ± 0.53 | 2.38 ± 0.34 | 4.36 ± 0.16 | 3.75 ± 0.29 |
| 4a | nd[1] | nd | nd | nd | nd | nd |
| control | 1.70 ± 0.00 | 1.75 ± 0.05 | 1.70 ± 0.00 | 1.70 ± 0.00 | 1.91 ± 0.21 | 1.91 ± 0.21 |

*Data were reported as the mean $\log_{10}$ titer ± standard error of the mean. Antibody titers ≤1.70 represent an endpoint titer of less than 1:50 and were below the limit of detection.
[1]nd indicates not done

TABLE 21

Total WBC counts (×1000) in macaques immunized with plasmid DNA vaccines with and without electroporation.

| Group ID | Week -2 | 0 | 2 | 4 | 6 | 8 | 10 | 16 |
|---|---|---|---|---|---|---|---|---|
| 2d | 10.3 ± 1.1 | 8.8 ± 1.4 | 8.1 ± 1.0 | 7.2 ± 0.7 | 7.1 ± 1.0 | 8.6 ± 0.7 | 6.9 ± 0.9 | 6.6 ± 0.4 |
| 3a | 8.6 ± 1.4 | 5.5 ± 0.8 | 7.9 ± 1.3 | 6.0 ± 0.9 | 6.3 ± 1.0 | 7.3 ± 1.1 | 7.8 ± 1.1 | 8.0 ± 1.6 |
| 3c | 9.4 ± 1.4 | 6.3 ± 0.6 | 8.0 ± 0.8 | 7.0 ± 0.8 | 7.3 ± 0.9 | 9.9 ± 0.9 | 8.4 ± 1.4 | 7.8 ± 1.2 |
| 3cE | 11.0 ± 1.7 | 12.1 ± 1.5 | 8.2 ± 1.1 | 18.4 ± 2.0 | 11.0 ± 1.3 | 13.1 ± 1.3 | 9.3 ± 0.9 | 7.9 ± 0.5 |
| 4a | 11.6 ± 0.8 | 10.3 ± 1.4 | 8.9 ± 0.8 | 8.0 ± 0.8 | 8.2 ± 0.5 | 7.9 ± 0.5 | 8.3 ± 0.7 | nd[1] |
| control | 7.6 ± 0.9 | 5.6 ± 0.7 | 7.1 ± 0.9 | 5.7 ± 0.6 | 5.9 ± 0.7 | 7.6 ± 1.3 | 5.6 ± 0.5 | 6.6 ± 0.7 |

*Peripheral blood white blood cell counts (WBC) as determined by complete blood count analysis are reported as the mean WBC (×1000/ml) ± standard error.
[1] nd, not done Peripheral blood red blood cell counts (RBC) in animals used in the study were determined over time by complete blood count analysis and reported as the mean RBC (×10$^6$/ml)±standard error. See Table 22.

The peripheral blood hemoglobin levels (g/dL) in animals used in the study were determined over time by complete blood count analysis and reported as the mean hemoglobin level±standard error. See Table 23.

Multi-plasmid immunization with the plasmids and immunogenic compositions described in Table 7 did not produce any adverse effects on the WBCs, RBCs and hemoglobin levels in animals used in this study. See Tables 21-23. One clear positive effect was detected when electroporation was used with the immunogenic composition used to immunize group 3cE. In this group, the number of WBC was significantly elevated throughout the time course of the study. See Table 21.

Peripheral blood platelet levels as determined in animals used in the study were determined over time by complete blood count analysis and reported as the mean platelet level (×1000)±standard error. See Table 24.

Percent hematocrit levels in animals used in the study were determined over time by complete blood count analysis and reported as the mean percent hematocrit level±standard error. See Table 25.

Peripheral blood total lymphocyte numbers as determined in animals used in the study were determined over time by complete blood count analysis and reported as the mean total lymphocyte number±standard error. See Table 26.

Peripheral blood total CD3$^+$ T-lymphocyte numbers in animals used in the study were determined over time by complete blood count analysis and reported as the mean total CD3$^+$ T-lymphocyte number±standard error. See Table 27.

TABLE 22

Total RBC counts (×10$^6$) in macaques immunized with plasmid DNA vaccines with and without electroporation.

| Group ID | Week -2 | 0 | 2 | 4 | 6 | 8 | 10 | 16 |
|---|---|---|---|---|---|---|---|---|
| 2d | 5.60 ± 0.12 | 5.64 ± 0.03 | 5.62 ± 0.08 | 5.69 ± 0.09 | 5.70 ± 0.11 | 5.67 ± 0.11 | 5.74 ± 0.06 | 5.91 ± 0.08 |
| 3a | 5.61 ± 0.19 | 5.36 ± 0.17 | 5.39 ± 0.17 | 5.40 ± 0.13 | 5.39 ± 0.15 | 5.53 ± 0.18 | 5.32 ± 0.14 | 5.70 ± 0.16 |
| 3c | 5.39 ± 0.13 | 5.32 ± 0.14 | 5.43 ± 0.09 | 5.46 ± 0.13 | 5.38 ± 0.14 | 5.45 ± 0.10 | 5.52 ± 0.13 | 5.69 ± 0.09 |
| 3cE | 5.63 ± 0.15 | 5.91 ± 0.09 | 5.80 ± 0.07 | 5.60 ± 0.21 | 5.87 ± 0.10 | 5.57 ± 0.13 | 5.70 ± 0.07 | 5.75 ± 0.11 |
| 4a | 5.99 ± 0.11 | 5.68 ± 0.09 | 5.97 ± 0.08 | 5.77 ± 0.11 | 5.84 ± 0.07 | 5.79 ± 0.12 | 5.54 ± 0.10 | nd[1] |
| control | 5.69 ± 0.18 | 5.49 ± 0.13 | 5.57 ± 0.09 | 5.63 ± 0.09 | 5.61 ± 0.08 | 5.66 ± 0.09 | 5.73 ± 0.12 | 5.94 ± 0.13 |

*Peripheral blood red blood cell counts (RBC) were determined by complete blood count analysis and reported as the mean RBC (×10$^6$/ml) ± standard error.

TABLE 23

Total hemaglobin levels in macaques immunized with plasmid DNA vaccines with and without electroporation.

| Group ID | Week -2 | 0 | 2 | 4 | 6 | 8 | 10 | 16 |
|---|---|---|---|---|---|---|---|---|
| 2d | 12.5 ± 0.3 | 12.7 ± 0.2 | 12.5 ± 0.2 | 12.6 ± 0.2 | 12.5 ± 0.1 | 12.6 ± 0.2 | 12.9 ± 0.2 | 13.1 ± 0.2 |
| 3a | 13.1 ± 0.3 | 12.6 ± 0.3 | 12.6 ± 0.3 | 12.5 ± 0.3 | 12.6 ± 0.3 | 13.0 ± 0.3 | 12.8 ± 0.4 | 13.4 ± 0.2 |
| 3c | 12.7 ± 0.3 | 12.6 ± 0.2 | 12.7 ± 0.2 | 12.7 ± 0.2 | 12.6 ± 0.4 | 13.0 ± 0.3 | 13.2 ± 0.3 | 13.5 ± 0.3 |
| 3cE | 12.8 ± 0.3 | 13.4 ± 0.2 | 13.0 ± 0.2 | 13.1 ± 0.3 | 13.4 ± 0.2 | 12.9 ± 0.2 | 13.0 ± 0.1 | 13.3 ± 0.2 |
| 4a | 13.5 ± 0.3 | 13.1 ± 0.2 | 13.5 ± 0.2 | 13.1 ± 0.2 | 13.2 ± 0.2 | 13.1 ± 0.2 | 12.5 ± 0.2 | nd[1] |
| control | 13.3 ± 0.3 | 12.8 ± 0.3 | 13.0 ± 0.2 | 12.9 ± 0.2 | 13.0 ± 0.2 | 13.2 ± 0.1 | 13.6 ± 0.3 | 13.9 ± 0.3 |

*Peripheral blood hemoglobin levels (g/dL) as determined by complete blood count analysis are reported as the mean hemoglobin level ± standard error.
[1] nd, not done Peripheral blood total $CD3^+CD4^+$ Th-lymphocyte numbers in animals used in the study were determined over time by complete blood count analysis and reported as the mean total $CD3^+CD4^+$ Th-lymphocyte number±standard error. See Table 28.

Peripheral blood total $CD3^+CD8^+$ T-lymphocyte numbers in animals used in the study were determined over time by complete blood count analysis and reported as the mean total $CD3^+CD8^+$ T-lymphocyte number±standard error. See Table 29.

Peripheral blood total $CD20^+$ lymphocyte numbers in animals used in the study were determined over time by complete blood count analysis and reported as the mean total $CD20^+$ lymphocyte number±standard error. See Table 30.

TABLE 24

Total platelet counts (×1000) in macaques immunized with plasmid DNA vaccines with and without electroporation.

| Group ID | Week | | | | | | | |
|---|---|---|---|---|---|---|---|---|
| | −2 | 0 | 2 | 4 | 6 | 8 | 10 | 16 |
| 2d | 404 ± 42 | 433 ± 19 | 399 ± 21 | 411 ± 16 | 392 ± 30 | 420 ± 13 | 448 ± 17 | 394 ± 21 |
| 3a | 419 ± 41 | 418 ± 31 | 399 ± 28 | 441 ± 25 | 402 ± 30 | 411 ± 20 | 450 ± 35 | 380 ± 17 |
| 3c | 454 ± 19 | 404 ± 13 | 418 ± 21 | 405 ± 19 | 391 ± 13 | 423 ± 41 | 381 ± 23 | 381 ± 27 |
| 3cE | 384 ± 29 | 389 ± 30 | 414 ± 31 | 389 ± 33 | 431 ± 33 | 315 ± 33 | 400 ± 24 | 347 ± 24 |
| 4a | 364 ± 21 | 373 ± 9 | 339 ± 16 | 368 ± 15 | 355 ± 16 | 357 ± 16 | 360 ± 19 | nd[1] |
| control | 458 ± 39 | 412 ± 33 | 386 ± 47 | 383 ± 14 | 386 ± 43 | 414 ± 35 | 409 ± 27 | 378 ± 34 |

*Peripheral blood platelet levels as determined by complete blood count analysis are reported as the mean platelet level (×1000) ± standard error.
[1]nd, not done

TABLE 25

Percent hematocrit in macaques immunized with plasmid DNA vaccines with and without electroporation.

| Group ID | Week | | | | | | | |
|---|---|---|---|---|---|---|---|---|
| | −2 | 0 | 2 | 4 | 6 | 8 | 10 | 16 |
| 2d | 38.3 ± 0.9 | 38.5 ± 0.5 | 37.8 ± 0.6 | 38.6 ± 0.4 | 38.4 ± 0.4 | 38.6 ± 0.5 | 38.9 ± 0.4 | 40.2 ± 0.5 |
| 3a | 39.9 ± 1.0 | 37.7 ± 0.8 | 38.4 ± 1.1 | 38.3 ± 0.9 | 38.0 ± 0.8 | 39.7 ± 1.1 | 38.3 ± 1.1 | 40.7 ± 0.7 |
| 3c | 38.9 ± 0.8 | 37.8 ± 0.8 | 38.7 ± 0.5 | 38.8 ± 1.1 | 38.4 ± 1.1 | 39.3 ± 0.9 | 39.7 ± 0.9 | 40.6 ± 0.8 |
| 3cE | 39.1 ± 0.9 | 40.6 ± 0.5 | 39.7 ± 0.6 | 39.6 ± 0.9 | 40.9 ± 0.5 | 39.0 ± 0.6 | 40.0 ± 0.3 | 39.9 ± 0.5 |
| 4a | 41.3 ± 0.8 | 38.8 ± 0.6 | 40.8 ± 0.5 | 39.6 ± 0.4 | 40.1 ± 0.6 | 39.8 ± 0.6 | 37.9 ± 0.5 | nd[1] |
| control | 40.3 ± 1.0 | 38.5 ± 0.6 | 39.3 ± 0.4 | 39.4 ± 0.4 | 39.6 ± 0.5 | 40.3 ± 0.5 | 40.8 ± 0.7 | 41.8 ± 0.7 |

*Percent hematocrit levels as determined by complete blood count analysis are reported as the mean percent hematocrit level ± standard error.
[1]nd, not done

TABLE 26

Total lymphocyte numbers in macaques immunized with plasmid DNA vaccines with and without electroporation.

| Group ID | Week | | | | | | | |
|---|---|---|---|---|---|---|---|---|
| | −2 | 0 | 2 | 4 | 6 | 8 | 10 | 16 |
| 2d | 3444 ± 554 | 4399 ± 521 | 3952 ± 578 | 4038 ± 462 | 3646 ± 677 | 4631 ± 574 | 3600 ± 581 | 3018 ± 422 |
| 3a | 2955 ± 613 | 2901 ± 452 | 2706 ± 405 | 2910 ± 434 | 2804 ± 459 | 3631 ± 714 | 3186 ± 775 | 3814 ± 736 |
| 3c | 3213 ± 448 | 3097 ± 369 | 3192 ± 407 | 3343 ± 559 | 3417 ± 699 | 4268 ± 667 | 3098 ± 678 | 3925 ± 805 |
| 3cE | 3157 ± 331 | 3737 ± 718 | 4441 ± 608 | 2737 ± 383 | 4835 ± 822 | 5286 ± 987 | 4927 ± 575 | 4385 ± 612 |
| 4a | 4850 ± 348 | 3763 ± 381 | 4268 ± 339 | 3471 ± 149 | 4544 ± 363 | 3494 ± 248 | 3408 ± 248 | nd[1] |
| control | 2638 ± 230 | 3685 ± 784 | 3280 ± 349 | 3037 ± 334 | 3828 ± 456 | 4392 ± 465 | 3451 ± 358 | 3470 ± 220 |

*Peripheral blood total lymphocyte numbers as determined by complete blood count analysis are reported as the mean total lymphocyte number ± standard error.
[1]nd, not done

TABLE 27

Total CD3+ T-lymphocyte numbers in macaques immunized with plasmid DNA vaccines with and without electroporation.

| Group ID | Week −2 | 0 | 2 | 4 | 6 | 8 | 10 | 16 |
|---|---|---|---|---|---|---|---|---|
| 2d | 1778 ± 356 | 2469 ± 265 | 2167 ± 306 | 2299 ± 257 | 2051 ± 356 | 2917 ± 313 | 2261 ± 318 | 1852 ± 218 |
| 3a | 1697 ± 291 | 1796 ± 269 | 1681 ± 255 | 1910 ± 327 | 1822 ± 322 | 2536 ± 450 | 2344 ± 619 | 2772 ± 523 |
| 3c | 1862 ± 215 | 1815 ± 175 | 1862 ± 187 | 1949 ± 279 | 2080 ± 341 | 2679 ± 313 | 2019 ± 385 | 2458 ± 426 |
| 3cE | 1716 ± 223 | 1926 ± 421 | 2718 ± 427 | 1417 ± 241 | 3139 ± 560 | 3437 ± 680 | 3229 ± 360 | 2928 ± 457 |
| 4a | 2848 ± 240 | 2141 ± 263 | 2481 ± 265 | 1881 ± 95 | 2851 ± 328 | 2153 ± 212 | 2141 ± 224 | nd[1] |
| control | 1455 ± 85 | 2188 ± 484 | 1883 ± 218 | 1749 ± 258 | 2334 ± 382 | 2789 ± 334 | 2352 ± 341 | 2291 ± 197 |

*Peripheral blood

TABLE 28

Total CD3+CD4+ Th-lymphocyte numbers in macaques immunized with plasmid DNA vaccines with and without electroporation.

| Group ID | Week −2 | 0 | 2 | 4 | 6 | 8 | 10 | 16 |
|---|---|---|---|---|---|---|---|---|
| 2d | 1117 ± 226 | 1463 ± 197 | 1348 ± 219 | 1371 ± 190 | 1317 ± 225 | 1770 ± 208 | 1435 ± 225 | 1457 ± 266 |
| 3a | 934 ± 143 | 1007 ± 158 | 986 ± 156 | 1084 ± 191 | 1078 ± 198 | 1425 ± 242 | 1291 ± 322 | 1535 ± 287 |
| 3c | 1132 ± 167 | 1108 ± 130 | 1178 ± 129 | 1195 ± 176 | 1283 ± 209 | 1598 ± 208 | 1229 ± 224 | 1480 ± 256 |
| 3cE | 1034 ± 155 | 1115 ± 194 | 1622 ± 267 | 827 ± 124 | 1752 ± 271 | 1917 ± 347 | 1673 ± 165 | 1628 ± 165 |
| 4a | 1774 ± 220 | 1362 ± 202 | 1528 ± 202 | 1171 ± 91 | 1743 ± 247 | 1363 ± 163 | 1360 ± 174 | nd[1] |
| control | 877 ± 79 | 1292 ± 259 | 1162 ± 117 | 1109 ± 155 | 1430 ± 239 | 1659 ± 226 | 1437 ± 178 | 1353 ± 139 |

*Peripheral blood total CD3+CD4+ Th-lymphocyte numbers as determined by complete blood count analysis are reported as the mean total CD3+CD4+ Th-lymphocyte number ± standard error.
[1]nd, not done

TABLE 29

Total CD3+CD8+ T-lymphocyte numbers in macaques immunized with plasmid DNA vaccines with and without electroporation.

| Group ID | Week −2 | 0 | 2 | 4 | 6 | 8 | 10 | 16 |
|---|---|---|---|---|---|---|---|---|
| 2d | 627 ± 141 | 1008 ± 105 | 807 ± 96 | 908 ± 87 | 729 ± 147 | 1137 ± 131 | 811 ± 103 | 678 ± 92 |
| 3a | 729 ± 159 | 778 ± 118 | 691 ± 94 | 823 ± 139 | 729 ± 120 | 1111 ± 224 | 1041 ± 285 | 1254 ± 251 |
| 3c | 663 ± 61 | 661 ± 69 | 635 ± 61 | 709 ± 102 | 744 ± 122 | 1023 ± 111 | 712 ± 151 | 884 ± 149 |
| 3cE | 626 ± 78 | 774 ± 229 | 1067 ± 169 | 542 ± 114 | 1409 ± 334 | 1431 ± 348 | 1528 ± 206 | 1270 ± 294 |
| 4a | 1005 ± 47 | 721 ± 70 | 901 ± 74 | 628 ± 53 | 994 ± 95 | 699 ± 64 | 718 ± 58 | nd[1] |
| control | 540 ± 92 | 876 ± 252 | 695 ± 151 | 625 ± 141 | 870 ± 172 | 1104 ± 184 | 872 ± 215 | 880 ± 131 |

*Peripheral blood total CD3+CD8+ T-lymphocyte numbers as determined by complete blood count analysis are reported as the mean total CD3+CD8+ T-lymphocyte number ± standard error.
[1]nd, not done

TABLE 30

Total CD20+ lymphocyte numbers in macaques immunized with multi-plasmid DNA vaccines with and without electroporation.

| Group ID | Week −2 | 0 | 2 | 4 | 6 | 8 | 10 | 16 |
|---|---|---|---|---|---|---|---|---|
| 2d | 1468 ± 309 | 1287 ± 347 | 1369 ± 403 | 1131 ± 328 | 1337 ± 391 | 1300 ± 331 | 993 ± 301 | 918 ± 275 |
| 3a | 1071 ± 296 | 857 ± 204 | 859 ± 218 | 767 ± 175 | 782 ± 195 | 799 ± 229 | 575 ± 115 | 746 ± 189 |
| 3c | 1143 ± 269 | 994 ± 205 | 1155 ± 264 | 1089 ± 283 | 1083 ± 340 | 1322 ± 380 | 902 ± 295 | 1175 ± 356 |
| 3cE | 1081 ± 140 | 968 ± 139 | 1221 ± 156 | 923 ± 125 | 1147 ± 201 | 1080 ± 173 | 1006 ± 138 | 966 ± 118 |
| 4a | 1332 ± 186 | 1127 ± 162 | 1247 ± 113 | 1255 ± 148 | 1051 ± 104 | 938 ± 100 | 987 ± 91 | nd[1] |
| Control | 984 ± 161 | 1134 ± 296 | 1171 ± 169 | 1027 ± 221 | 1206 ± 221 | 1223 ± 204 | 912 ± 144 | 945 ± 164 |

*Peripheral blood total CD20+ lymphocyte numbers as determined by complete blood count analysis are reported as the mean total CD20+ lymphocyte number ± standard error.
[1]nd, not done Multi-plasmid immunization with the plasmids and immunogenic compositions described in Table 7 also did not produce any adverse effects on the platelet counts (Table 24), percent hematocrit (Table 25), total lymphocyte numbers (Table 26), total CD3+ T-lymphocyte numbers (Table 27), total CD3+CD4+ Th-lymphocyte numbers (Table 28), total CD3+CD8+ T-lymphocyte numbers (Table 29), and total CD20+ T-lymphocyte numbers (Table 30), in animals used in this study. Again, in these analyses a positive effect on total lymphocyte numbers (Table 26), total CD3+ T-lymphocyte numbers (Table 27), total CD3+CD4+ Th-lymphocyte numbers (Table 28), total CD3+CD8+ T-lymphocyte numbers (Table 29), was detected when electroporation was used in conjunction with the bupivacaine formulated immunogenic composition to immunize group 3cE. In this group, the number of lymphocytes in each of these categories was significantly elevated at times during the course of the study.

The body weights of animals used in the study were monitored on a weekly basis. Body weights (kg) were reported as the mean body weight±standard error. See Table 31.

TABLE 31

Body weight (kg) of macaques immunized with multi-plasmid DNA vaccines with and without electroporation.

| Group ID | Week | | | | | | | |
|---|---|---|---|---|---|---|---|---|
| | −2 | 0 | 2 | 4 | 6 | 8 | 10 | 16 |
| 2d | 3.74 ± 0.27 | 3.63 ± 0.27 | 3.84 ± 0.29 | 3.93 ± 0.28 | 3.98 ± 0.29 | 4.16 ± 0.29 | 4.00 ± 0.28 | 4.05 ± 0.28 |
| 3a | 3.63 ± 0.19 | 3.56 ± 0.19 | 3.74 ± 0.22 | 3.75 ± 0.22 | 3.83 ± 0.25 | 3.98 ± 0.23 | 3.85 ± 0.25 | 3.96 ± 0.25 |
| 3c | 3.70 ± 0.23 | 3.65 ± 0.20 | 3.87 ± 0.24 | 3.97 ± 0.25 | 4.16 ± 0.25 | 4.26 ± 0.29 | 4.14 ± 0.26 | 4.28 ± 0.30 |
| 3cE | 3.67 ± 0.23 | 3.91 ± 0.23 | 4.03 ± 0.28 | 3.99 ± 0.26 | 4.04 ± 0.28 | 4.12 ± 0.25 | 4.06 ± 0.27 | 4.14 ± 0.30 |
| 4a | 3.67 ± 0.19 | 3.72 ± 0.21 | 3.83 ± 0.22 | 3.77 ± 0.19 | 3.85 ± 0.18 | 3.71 ± 0.18 | 3.72 ± 0.14 | nd[1] |
| control | 3.61 ± 0.23 | 3.66 ± 0.20 | 3.91 ± 0.18 | 4.03 ± 0.19 | 4.15 ± 0.18 | 4.24 ± 0.19 | 4.21 ± 0.20 | 4.29 ± 0.21 |

*Body weights (kg) are reported as the mean body weight ± standard error.
[1]nd, not done Finally, this analysis indicates that multi-plasmid immunization with the plasmids and immunogenic compositions described in Table 7 also did not produce any adverse effects on the body weights (Table 31) of animals used in this study.

Example 13

Murine Immunization Studies Using Immunogenic Compositions Comprising Four Plasmids Each Having a Single Transcriptional Unit Previous examples suggested that in situations where the total immune response must be maximized then it may be advantageous to use an immunogenic composition based on a combination of plasmids having a single transcriptional unit expressing a single antigen per plasmid. In this example, murine immunization studies were performed to compare immunogenic functionality of immunogenic compositions based on four plasmids with immunogenic compositions based on three plasmids. More particularly, the immunogenic functionality of an immunogenic composition based on four individual plasmids directing the expression of six HIV-1 genes including gag, pol, env, and only one fusion of nef-tat-vif genes was compared to immunogenic compositions based on three individual plasmids directing the expression of six HIV-1 genes including env, a fusion of gag-pol genes and a second fusion of nef-tat-vif genes. Immunogenic functionality was evaluated as relative ability of various three and four plasmid DNA-based immunogenic compositions to elicit multi-antigen-specific cell-mediated immune responses in Balb/c mice. The HIV genes and sequences were described in Example 1. The three plasmid immunogenic compositions from groups 3a and 3c were the same as described in Examples 8 and 9. See Tables 1 and 32.

Immunogenic Compositions and Immunization

Plasmid DNA expression vectors encoding HIVenv gp160, gag p55, pol (or a gag-pol fusion), or a nef-tat-vif fusion protein were used as the experimental immunogenic compositions, and the empty expression vector backbone was used as a control immunogenic composition vector. See Table 32 below for study design. HIV gene expression by the various expression vectors was confirmed by Western blot after transient transfection of human rhabdosarcoma (RD) cells. See Examples 4-7.

Group 3a has three plasmids with a single transcriptional unit plasmid each, but where two of the antigens are fusion proteins (gag-pol and nef-tat-vif). Group 3c also has three plasmids but where two of the plasmids have a single transcriptional unit and the third plasmid has two complete transcriptional units. See Table 32. Only one of the antigens is expressed as a fusion protein (nef-tat-vif). Group 4a has four plasmids with a single transcriptional unit plasmid each, but where only one of the antigens was a fusion protein (nef-tat-vif).

The adjuvant used for these studies was also delivered via a DNA plasmid. In this example, all animals were co-injected with 25 μg of plasmid no. 212 encoding murine IL-12 p35 and p40 genes and expressing murine Il-12. See Table 1.

Balb/c mice were immunized intramuscularly with 100 total μg doses of DNA as outlined in Table 32. In all cases, immunogenic compositions were formulated with 0.25% bupivacaine and injected into the quadricep muscles in a 100 μl volume. Ten days after the second immunization, animals were sacrificed and the serum and spleens were isolated for immune assays. Spleens were used to measure antigen-specific IFN-gamma secreting cells using ELISPOT assays as described below.

Animals

For these studies, 4-6 week old female Balb/c mice were used. Mice were maintained in accordance with the Guide for the Care and Use of Laboratory Animals (National Research Council, National Academic Press, Washington, D.C., 1996). In addition, procedures for the use and care of the mice were approved by Wyeth Research's Institutional Animal Care and Use Committee.

TABLE 32

Murine Study Design - Two Immunizations

| [1]Group No. | Plasmid No. | Plasmid description | Total DNA (ug) | No. mice | Immunization Schedule (week) |
|---|---|---|---|---|---|
| 3a | 111 | HCMV-gag/pol | 33 | 8 | 0 - 3 |
|  | 104 | HCMV-ntv | 33 |  |  |
|  | 101 | HCMV-env | 33 |  |  |
| 3c | 102 | HCMV-gag | 33 | 8 | 0 - 3 |
|  | 103 | HCMV-pol | 33 |  |  |
|  | 202 | HCMV-ntv, SCMV-env | 33 |  |  |
| 4a | 101 | HCMV-env | 25 | 8 | 0 - 3 |
|  | 102 | HCMV-gag | 25 |  |  |
|  | 103 | HCMV-pol | 25 |  |  |
|  | 104 | HCMV-ntv | 25 |  |  |
| 5 | 001 | Vector control | 100 | 4 | 0 - 3 |

[1]Groups 3a and 3c utilize the same immunogenic compositions as in Table 3.

The data shown in Table 33 indicates that increasing the number of antigen expressing plasmids from 3 to 4 in the immunogenic composition did not produce any dramatic increase in immune response to HIV proteins. See Table 33.

TABLE 33

Murine Immune Responses Following Two Immunizations

| Group ID | gag-specific response* | pol-specific response | env-specific response | ntv#-specific response | Total HIV-specific response |
|---|---|---|---|---|---|
| Control | 3 | 0 | 9 | 1 | 13 |
| 3a | 163 | 247 | 1564 | 116 | 2090 |
| 3c | 436 | 1155 | 671 | 83 | 2345 |
| 4a | 294 | 662 | 1150 | 123 | 2229 |

*antigen-specific IFN-gamma ELISPOT responses are reported as the spot forming cells (#SFC/$10^6$ splenocytes) excreting interferon gamma per $10^6$ splenocytes.
ntv, nef-tat-vif fusion protein All documents cited herein are incorporated by reference. Various modifications and minor alterations in the method and components are believed to be clear to those of skill in the art.

What is claimed is:

1. An immunogenic composition for inducing an immune response to human immunodeficiency virus (HIV) in a mammal, said immunogenic composition comprising:
   (a) a first DNA plasmid comprising a single transcriptional unit consisting of a nucleotide sequence that encodes an HIV gag-pol fusion polypeptide operably linked to a human cytomegalovirus (HCMV) immediate early promoter and a Bovine growth hormone polyadenylation (BGH poly A) signal;
   (b) a second DNA plasmid comprising (i) a first transcriptional unit consisting of a nucleotide sequence that encodes an HIV nef-tat-vif fusion polypeptide operably linked to a HCMV immediate early promoter and a Simian virus 40 polyadenylation (SV40 poly A) signal; (ii) a second transcriptional unit consisting of a nucleotide sequence that encodes an HIV envelope polypeptide operably linked to a simian cytomegalovirus (SCMV) promoter and a BGH polyadenylation signal; and wherein the direction of transcription for said first transcriptional unit is in the opposite direction from the direction of transcription of said second transcriptional unit; or wherein the direction of transcription for said first transcriptional unit is in the same direction from the direction of transcription of said second transcriptional unit and said first and second transcriptional units are separated by a spacer region of at least one kilobase pairs;
   (c) an adjuvant and at least one of a pharmaceutically acceptable diluent, carrier or transfection facilitating agent.

2. The immunogenic composition of claim 1, wherein said transfection facilitating agent is bupivacaine.

3. The immunogenic composition of claim 1, wherein said HIV nef-tat-vif fusion polypeptide is a nef, tat, and vif (NTV) fusion protein expressed from a fusion of the nef, tat, and vif (ntv) genes of HIV.

* * * * *